(12) United States Patent
Polchin et al.

(10) Patent No.: US 12,090,004 B2
(45) Date of Patent: Sep. 17, 2024

(54) REGISTRATION DEGRADATION CORRECTION FOR SURGICAL NAVIGATION PROCEDURES

(71) Applicant: Digital Surgery Systems, Inc., Goleta, CA (US)

(72) Inventors: George C. Polchin, Goleta, CA (US); Stephen C. Minne, Goleta, CA (US)

(73) Assignee: Digital Surgery Systems, Inc., Goleta, CA (US)

( * ) Notice: Subject to any disclaimer, the term of this patent is extended or adjusted under 35 U.S.C. 154(b) by 0 days.

(21) Appl. No.: 18/271,808

(22) PCT Filed: Jan. 11, 2022

(86) PCT No.: PCT/US2022/011992
§ 371 (c)(1),
(2) Date: Jul. 11, 2023

(87) PCT Pub. No.: WO2022/150767
PCT Pub. Date: Jul. 14, 2022

(65) Prior Publication Data
US 2023/0390021 A1    Dec. 7, 2023

Related U.S. Application Data

(60) Provisional application No. 63/135,819, filed on Jan. 11, 2021.

(51) Int. Cl.
*A61B 90/00* (2016.01)
*A61B 34/20* (2016.01)
(Continued)

(52) U.S. Cl.
CPC ............. *A61B 90/39* (2016.02); *A61B 34/20* (2016.02); *A61B 34/30* (2016.02); *G06T 7/337* (2017.01);
(Continued)

(58) Field of Classification Search
CPC ......... A61B 90/39; A61B 34/20; A61B 34/30; A61B 2034/2065; A61B 2090/395;
(Continued)

(56) References Cited

U.S. PATENT DOCUMENTS 5,486,291 A * 1/1996 Todd .................... C02F 3/06
                                                    210/617
2007/0055290 A1   3/2007 Lober
(Continued)

FOREIGN PATENT DOCUMENTS

WO   2020041941 A   3/2020

OTHER PUBLICATIONS

Orthalign Inc. HipAlign® Surgical Technique Manual Total Hip Arthroplasty Posterior Approach. Nov. 30, 2017 (Nov. 30, 2017. [retrieved on Mar. 11, 2022]. Retrieved from the Interent: <URL: https://amplitude-ortho.com.au/wp-content/uploads/2020/07/orthalign-hip-surgical-technique-390 142.pdf> pp. 1-21.

*Primary Examiner* — Aaron F Roane
(74) *Attorney, Agent, or Firm* — K&L Gates LLP; Dennis A. Majewski

(57) ABSTRACT

New and innovative systems and methods for registration degradation correction for surgical procedures are disclosed. An example system includes a surgical marking pen including a first trackable target and a registration plate including a second trackable target. The system also includes a navigation camera and a processor configured to perform a pen registration that determines a transformation between a tip of the surgical marking pen and the first trackable target when the tip of the surgical marking pen is placed on the registration plate. The pen registration enables the processor to record virtual marks at locations of the pen tip that correspond to physical marks drawn by the pen. Locations of the virtual marks are later compared to images of the physical marks to correct any registration degradation by (Continued)

moving a surgical camera or robotic arm connected to the surgical camera.

22 Claims, 21 Drawing Sheets

(51) Int. Cl.
*A61B 34/30* (2016.01)
*G06T 7/33* (2017.01)
*G06T 7/80* (2017.01)

(52) U.S. Cl.
CPC ........ *G06T 7/85* (2017.01); *A61B 2034/2065* (2016.02); *A61B 2090/395* (2016.02); *G06T 2207/10012* (2013.01); *G06T 2207/10081* (2013.01); *G06T 2207/10092* (2013.01); *G06T 2207/30004* (2013.01); *G06T 2207/30204* (2013.01); *G06T 2207/30244* (2013.01)

(58) Field of Classification Search
CPC ............ G06T 7/85; G06T 7/337; G06T 2207/10012; G06T 2207/10081; G06T 2207/10092; G06T 2207/30004; G06T 2207/30204; G06T 2207/30244
USPC .......................................................... 606/1
See application file for complete search history.

(56) References Cited

U.S. PATENT DOCUMENTS

| 2016/0135762 A1 | 5/2016 | Mihailescu et al. |
| 2017/0116729 A1 | 4/2017 | Stolka et al. |
| 2018/0132941 A1 | 5/2018 | Haider et al. |
| 2020/0197107 A1 | 6/2020 | Ryan et al. |

* cited by examiner

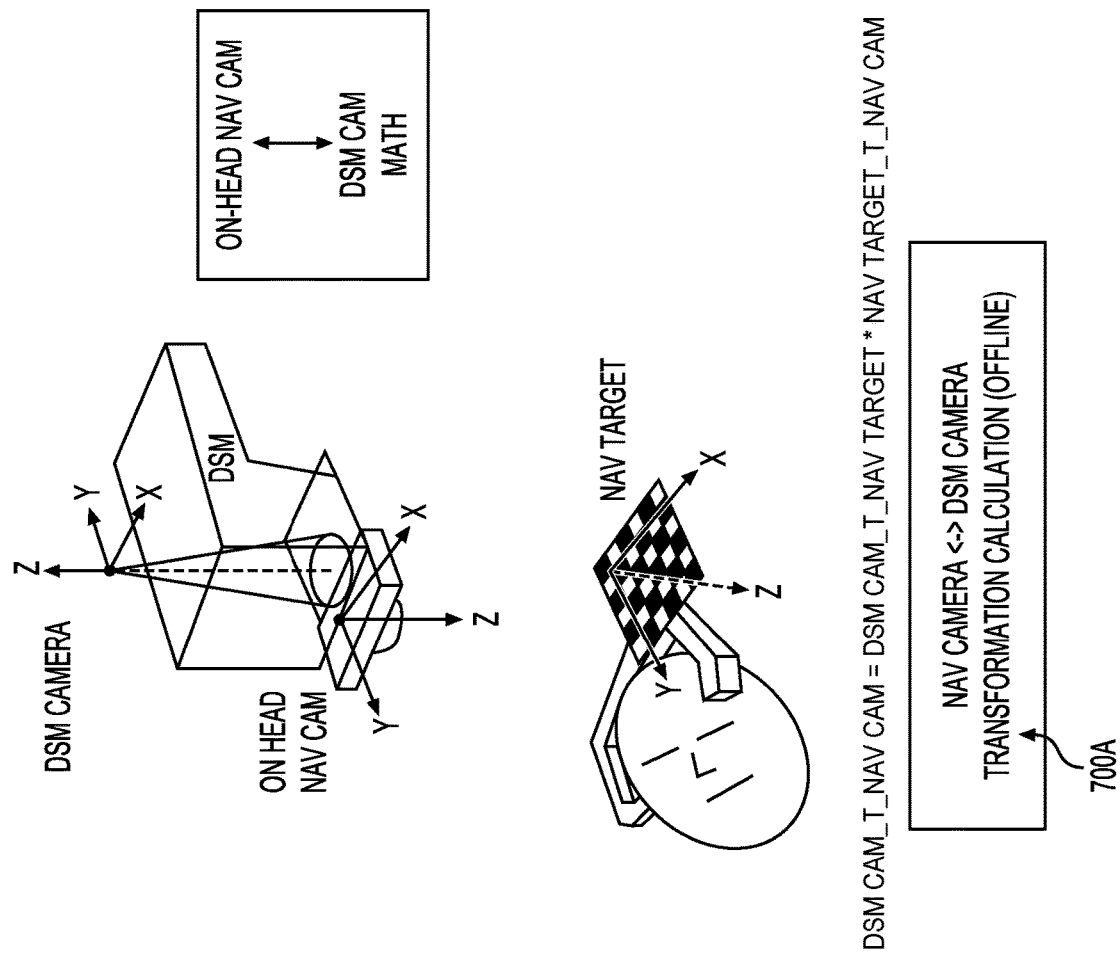

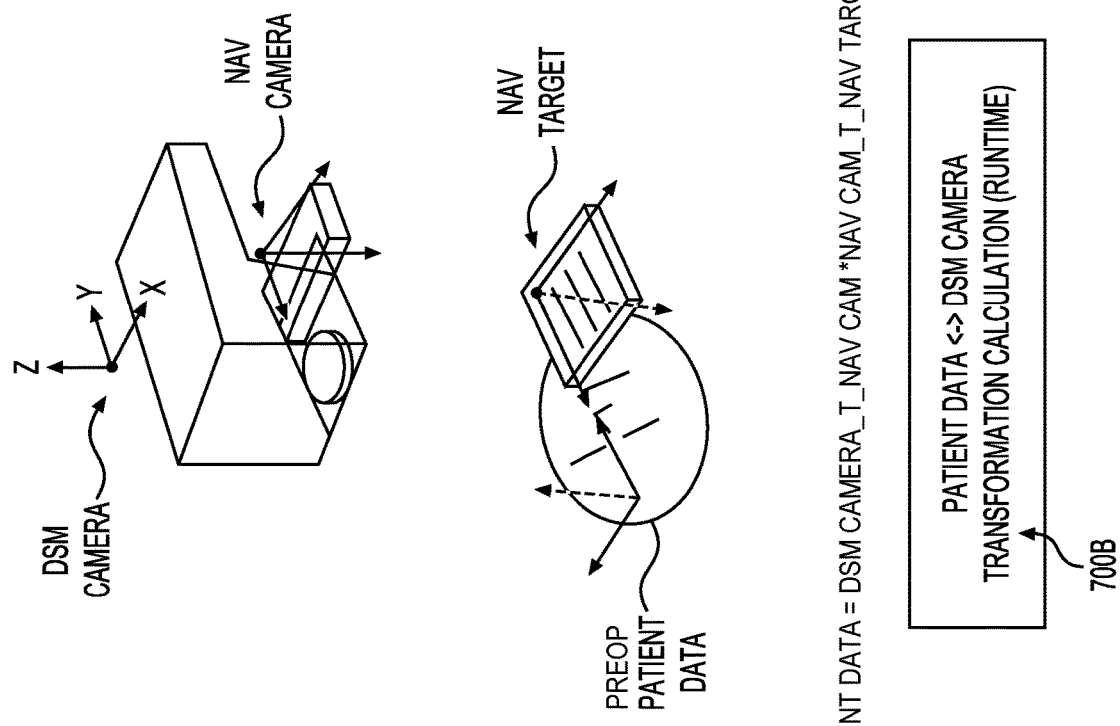

REGISTRATION DEGRADATION CORRECTION FOR SURGICAL NAVIGATION PROCEDURES

PRIORITY CLAIM

The present application is a national phase entry of PCT Patent Application No. PCT/US2022/011992, filed on Jan. 11, 2022, which claims priority to and the benefit of U.S. Provisional Patent Application No. 63/135,819, filed on Jan. 11, 2021, the entirety of which is herein incorporated by reference.

TECHNICAL FIELD

Certain aspects of the present disclosure generally relate to surgical systems, and specifically relate to systems and methods for patient registration correction for surgical navigation procedures.

BACKGROUND

Computer assisted surgery is becoming increasingly popular as applications are developed that enable computer-based systems to be extensions of a surgeon's eyes and/or hands. A first step for performing a computer assisted surgery is to obtain a three-dimensional ("3D") dataset that reproduces with great accuracy the geometry of the normal and pathological tissues in a region of a patient that is to be operated on by a surgeon. This is mainly obtained by using CT or MRI scans of that region. The role of patient registration is to obtain a close-to-ideal reference reproducibility of the dataset to correlate the position (offset) of the gathered dataset with the patient's position during the surgical procedure. Patient registration eliminates the necessity of maintaining the same strict position of the patient during both preoperative scanning and surgery. Patient registration also creates the necessary reference information to enable a surgical robot to act accurately on a patient, even if the patient has (been) moved during the procedure. The patient registration procedure is crucial in computer assisted surgery to insure the reproducibility of the preoperative registration and the clinical situation during surgery. A problem in current surgical navigation is patient registration degradation, which can occur due to various circumstances. For instance, after normal registration, a patient anatomy may move relative to a patient reference frame and/or the patient reference frame may move relative to a securing device or physical frame (also referred to as a "clamp") that holds or is secured to the patient anatomy. Such movement can happen at any point during a surgical procedure.

In various instances, a surgical navigation system is set up using a known routine. First, patient anatomy is secured in a securing device, such as a Mayfield clamp. A navigation target is then secured to the securing device. The reference frame of this target is known as the patient reference frame. Such a term refers to the target itself since mathematically the reference frame of the securing device is defined by and identical to the reference frame of the target. A navigation target is next secured to a navigation tool, such as a probe, as one of the options for use in patient registration. A navigation target is then secured to a digital surgical microscope or camera. A calibration procedure is then performed to determine the optical parameters of the digital surgical microscope or camera to include the extrinsic and the intrinsic parameters of the digital surgical microscope or camera at all optical settings to be used during the surgical procedure. The extrinsic parameters include the pose of the optical axis relative to the navigation target. The intrinsic parameters of the digital surgical microscope or camera include a focal length, a principal point, and optionally distortion correction parameters.

The navigation camera is positioned to view the patient reference frame navigation target and the microscope/camera navigation target. It is understood that any other navigation targets to be used during the procedure (such as those attached to tools) must be brought into the field of view of the navigation camera during use. An information processor module of the system communicates with the navigation camera to receive the pose information of each target in some space designated by the navigation camera, which is typically the space of the navigation camera. Oftentimes, registration errors between the navigation targets and patient reference frame can occur due to shifts in the patient and/or camera system. A need accordingly exists for a surgical navigation system that provides for automatic registration correction.

SUMMARY

The present disclosure provides a surgical marking pen, system, and method that enables the recording of a patient registration in the form or real, physical marks or other such fiducials directly on the patient anatomy. The system and method disclosed herein correlate the physical marks to virtual marks that are added to patient volume data or surgical templates. In some embodiments, the surgical marking pen is configured to designate locations of the virtual marks without placing physical marks are not placed on a patient. Alternatively, the surgical marking pen may be omitted. In these alternative embodiments, physical patient features (e.g., natural patient marks), such as bone structure, scars, beauty marks, and other readily distinguishable bodily structure, are used in place of the physical marks. The system and method are configured in these alternative embodiments to create virtual marks that align with the natural patient marks to provide for automatic registration correction of the patient volume data.

As disclosed herein, the surgical marking pen is configured to help enable correction of misalignment (patient degradation) due to patient draping, which is a major source of patient registration error. The provided surgical marking pen may also help enable correction of misalignment due to patient reference frame target movement. In one example, the provided surgical marking pen may help enable correction of misalignment due to microscope reference frame target movement. The provided surgical marking pen may further help enable pediatric or other "soft clamp" or non-clamping methods. For instance, marks made by the pen disclosed herein may provide the guideposts necessary to judge, and improve where necessary, the integrity of the registration over the course of the case.

The systems and methods disclosed herein are configured to "lock in" a current state of a patient registration at any point in a procedure and return to it based solely on the appearance of the patient anatomy. When such a "lock-in" is performed, as provided by the present disclosure, shortly after the best-practice patient registration method of the surgical navigation system is performed, a surgeon is able to return to this best-practice patient registration at will for the next segment of the procedure. As patient anatomy changes, further lock-ins are performed, using the remainder of the prior known-best lock-in as a basis, enabling the known-best patient registration to be maintained with significantly lower degradation than typical known systems or methods.

The example system and method performs a patient registration using best practices of the known surgical navigation system. Such a "best practice" patient registration enables the system to determine the pose of patient anatomy (and hence the pose of patient volume scan data taken at or before this time) relative to the patient reference frame. Prior camera calibration and optical axis pose determination relative to the microscope-mounted navigation target enable the drawing and registered overlay of a representation of patient volume data, where the patient data is generated via one or more of several means such as pre-operative CT scan or MRI scan, or peri-operative such scans. The "registered" part of such a registered overlay means that features in the overlay corresponding to features in the live view are aligned onscreen to within some error. The camera calibration enables such an overlay to be registered in three dimensions, and thus enables "X-ray vision" into the patient at the same time and in the same place as the live patient anatomy.

In a surgical procedure, a navigated digital surgical microscope (e.g., a digital surgical microscope (DSM) head mounted on a robotic arm) is used to provide images of a live view of patient anatomy. The disclosed system registers patient data (e.g., patient volume scan data f) to the live images. The system then overlays the registered patient data on the live surgical view to provide computed assisted surgery. The present disclosure uses the DSM's capabilities to provide visual means of performing a return to the best-practice registration at will. The present disclosure also enables increased confidence in applications such as pediatric surgery, where traditional clamping is challenging or dangerous to the patient. The present disclosure is also adapted to enable low-cost surgical navigation, for example, for developing countries.

The example system and method disclosed herein may use pose information to provide registration correction. The pose information (also called transformation matrices or transformations) for two targets are represented, for example, as navCamera_T_markerTarget and navCamera_T_regPlateTarget, where such a label is read "backwards" to indicate a transformation from one space to another. For example "navCamera_T_markerTarget" is read as "the transformation of marker target space to navigation camera space" or "marker target to navigation camera." These transformations may include 4×4 homogeneous transformation matrices, which comprise a "rotation part" and a "translation part." The rotational part describes the orientation transformation between the two spaces and the translation part describes the position transformation.

In light of the disclosure herein and without limiting the disclosure in any way, in a first aspect of the present disclosure, which may be combined with any other aspect listed herein unless specified otherwise, a system includes a surgical marking pen including a first trackable target. The surgical marking pen is configured to generate a physical mark on a patient. The system also includes a marking pen registration plate including a second trackable target and an indicator specifying a location to place a tip of the surgical marking pen and a navigation camera. The first and second trackable targets are posed at least some of the time such that they are visible to the navigation camera. The system further includes a memory storing machine-readable instructions and a processor in communication with the memory. Execution of the machine-readable instructions causes the processor to perform an initial patient registration that registers a patient volume space of virtual positional data points to physical positional points of at least a portion of a patient, perform a pen registration that determines a transformation between a tip of the surgical marking pen and the first trackable target by determining relative poses between the first trackable target and the second trackable target when the tip of the surgical marking pen is placed on the indicator and the first and second trackable targets are viewable by the camera, record a virtual mark in the patient volume space in response to an activation action performed by the surgical marking pen using the pen registration, the virtual mark being a virtual positional data point that corresponds to the physical positional point of a physical mark generated on the patient by the tip of the surgical marking pen, and cause the patient volume space of the virtual positional data points and the recorded virtual mark to be displayed in an overlaid manner over live image data recorded by a surgical camera on one or more displays.

In accordance with a second aspect of the present disclosure, which may be used in combination with any other aspect listed herein unless stated otherwise, the activation action is one of a press and swivel action, an electronic communication activation mechanism, an electro-optic communications activation mechanism, voice activation, or a footswitch or other hardware-based method.

In accordance with a third aspect of the present disclosure, which may be used in combination with any other aspect listed herein unless stated otherwise, the activation action includes maintaining a positioning of the surgical marking pen relative to a patient for a predetermined amount of time.

In accordance with a fourth aspect of the present disclosure, which may be used in combination with any other aspect listed herein unless stated otherwise, the patient volume space includes patient volume scan data from magnetic resonance imaging ("MRI") images, diffusion tensor imaging ("DTI") images, or computed tomography ("CT") images or a surgical template.

In accordance with a fifth aspect of the present disclosure, which may be used in combination with any other aspect listed herein unless stated otherwise, execution of the machine-readable instructions further causes the processor to display recommended locations for virtual marks.

In accordance with a sixth aspect of the present disclosure, which may be used in combination with any other aspect listed herein unless stated otherwise, the recommended locations include three or more points provides in an asymmetric shape.

In accordance with a seventh aspect of the present disclosure, which may be used in combination with any other aspect listed herein unless stated otherwise, the virtual mark includes at least one of a dot, a line, a symbol, or a character.

In accordance with an eighth aspect of the present disclosure, which may be used in combination with any other aspect listed herein unless stated otherwise, execution of the machine-readable instructions further causes the processor to sample in time portions of the at least one line, symbol, or character as distinct points or one or more equations describing a line segment formed by joining at least some of the distinct points.

In accordance with a ninth aspect of the present disclosure, which may be used in combination with any other aspect listed herein unless stated otherwise, the indicator of the marking pen registration plate includes at least one of a fiducial containing a feature able to accept the tip of the surgical marking pen or a two-dimensional crosshair graphical indication.

In accordance with a tenth aspect of the present disclosure, which may be used in combination with any other aspect listed herein unless stated otherwise, the system further includes the surgical camera as a stereoscopic or visualization camera.

In accordance with an eleventh aspect of the present disclosure, which may be used in combination with any other aspect listed herein unless stated otherwise, execution of the machine-readable instructions further causes the processor to obtain the virtual positional data points that are related to the physical positional points of at least the portion of the patient by recording one or more images of physical positional points of at least the portion of the patient at different poses.

In accordance with a twelfth aspect of the present disclosure, which may be used in combination with any other aspect listed herein unless stated otherwise, execution of the machine-readable instructions further causes the processor to record the virtual mark before draping of the patient.

In accordance with a thirteenth aspect of the present disclosure, which may be used in combination with any other aspect listed herein unless stated otherwise, execution of the machine-readable instructions further causes the processor to compare locations of the virtual mark to the physical mark generated on the patient as shown in the live image data, determine when a distance between the location of the virtual mark and the location of the physical mark exceeds a threshold, and cause a misalignment alert to be displayed on the single display.

In accordance with a fourteenth aspect of the present disclosure, which may be used in combination with any other aspect listed herein unless stated otherwise, execution of the machine-readable instructions further causes the processor to enter a correction phase when a request is received from an operator or the distance between the location of the virtual mark and the location of the physical mark exceeds the threshold, record or determine a first pose of the surgical camera and a robotic arm supporting the surgical camera, cause at least one of the surgical camera or the robotic arm to move such that the virtual mark is aligned with the physical mark, record or determine a second pose of the surgical camera and the robotic arm, and calculate a registration correction transformation as a pose delta between the second pose and the first pose of the surgical camera and the robotic arm.

In accordance with a fifteenth aspect of the present disclosure, which may be used in combination with any other aspect listed herein unless stated otherwise, execution of the machine-readable instructions further causes the processor to (i) receive an input from an operator to move the at least one of the surgical camera or the robotic arm by a specified distance or degree of rotation, and (ii) cause the at least one of the surgical camera or the robotic arm to move by the specified distance while keeping the virtual mark stationary with respect to a camera space of the surgical camera.

In accordance with a sixteenth aspect of the present disclosure, which may be used in combination with any other aspect listed herein unless stated otherwise, (i) and (ii) are repeated until the at least one of the surgical camera or the robotic arm is moved until the virtual mark is aligned with the physical mark, subsequent poses of the surgical camera and the robotic arm are recorded or determined as (i) and (ii) are repeated, and a final registration correction transformation is calculated as the pose delta between the first pose and a final pose of the subsequent poses.

In accordance with a seventeenth aspect of the present disclosure, which may be used in combination with any other aspect listed herein unless stated otherwise, the patient volume space of the virtual positional data points and the recorded virtual mark are held fixed relative to the surgical camera when the at least one of the surgical camera or the robotic arm is moved to align the virtual mark with the physical mark.

In accordance with an eighteenth aspect of the present disclosure, which may be used in combination with any other aspect listed herein unless stated otherwise, execution of the machine-readable instructions further causes the processor to enter a correction phase when a request is received from an operator or the distance between the location of the virtual mark and the location of the physical mark exceeds the threshold, and cause the patient volume space of the virtual positional data points and the recorded virtual mark to move within the live image data recorded by the surgical camera such that the virtual mark becomes aligned with the physical mark, wherein the surgical camera and a robotic arm supporting the surgical camera are held in a fixed pose during movement of the patient volume space of the virtual positional data points and the recorded virtual mark.

In accordance with a nineteenth aspect of the present disclosure, which may be used in combination with any other aspect listed herein unless stated otherwise, the surgical camera is connected to a robotic arm, and execution of the machine-readable instructions further causes the processor to at a time the virtual mark is created, associatively store with the virtual mark a waypoint including at least one of a robot pose of the robotic arm in the form of joint angles or camera optical properties including at least one of zoom, focus, orientation, or coupler settings, and cause at least one of the robotic arm or the surgical camera to return to the waypoint to enable an operator to begin a process of correcting the misalignment between the location of the virtual mark and the location of the physical mark.

In accordance with a twentieth aspect of the present disclosure, which may be used in combination with any other aspect listed herein unless stated otherwise, the surgical camera is connected to a robotic arm, and execution of the machine-readable instructions further causes the processor to iteratively move the robotic arm and use the live image data to determine a new distance between the location of the virtual mark and the location of the physical mark until the location of the virtual mark is aligned with the location of the physical mark.

In accordance with a twenty-first aspect of the present disclosure, which may be used in combination with any other aspect listed herein unless stated otherwise, a system includes a surgical camera configured to record images of a patient, a navigation camera, a memory storing machine-readable instructions, and a processor in communication with the memory. Execution of the machine-readable instructions causes the processor to perform an initial patient registration that registers a patient volume space of virtual positional data points to physical positional points of at least a portion of the patient, identify or receive an indication of an identification of a natural patient mark using recorded images of the patient, record a virtual mark in the patient volume space in response to a received activation action based on the identification of the natural patient mark, the virtual mark being a virtual positional data point that corresponds to a physical positional point of the natural patient mark, and cause the patient volume space of virtual positional data points and the recorded virtual mark to be displayed in an overlaid manner over the recorded images on a single display.

In accordance with a twenty-second aspect of the present disclosure, which may be used in combination with any other aspect listed herein unless stated otherwise, the natural patient mark includes at least one of skin features such as moles or freckles, a "fingerprint" type feature such as hair follicle pattern or a skin pore pattern, a feature of the surgery such a bone ridge in a craniometry, or at least one three-dimensional feature of the patient's anatomy as extracted using at least one of a stereoscopic surgical camera or cameras providing multiple views of the patient's anatomy.

In accordance with a twenty-third aspect of the present disclosure, which may be used in combination with any other aspect listed herein unless stated otherwise, the activation action includes recording or storing an image or a stereoscopic image using the surgical camera to identify or specify the natural patient mark.

In accordance with a twenty-fourth aspect of the present disclosure, which may be used in combination with any other aspect listed herein unless stated otherwise, a system includes a surgical marking pen including a tip and a trackable target, the surgical marking pen configured to generate a physical mark on a patient, and a navigation camera, wherein the trackable target and the tip of the surgical marking pen are posed at least some of the time such that they are visible to the camera. The system also includes a memory storing machine-readable instructions, and a processor in communication with the memory. Execution of the machine-readable instructions causes the processor to perform an initial patient registration that generates a patient volume space of virtual positional data points that corresponds to physical positional points of at least a portion of a patient, receive or determine a pose transformation between the trackable target and the surgical pen tip, record a virtual mark in the patient volume space in response to an activation action performed by the surgical marking pen using the pose transformation, the virtual mark being a virtual positional data point that corresponds to the physical positional point of a physical mark generated on the patient by the tip of the surgical marking pen, and cause the patient volume space of virtual positional data points and the recorded virtual mark to be displayed in an overlaid manner over live image data recorded by a surgical camera on a single display.

In accordance with a twenty-fifth aspect of the present disclosure, which may be used in combination with any other aspect listed herein unless stated otherwise, a system includes a navigation camera, surgical visualization camera, a memory storing machine-readable instructions, and a processor in communication with the memory. Execution of the machine-readable instructions causes the processor to perform an initial patient registration using the navigation camera that generates a patient volume space of virtual positional data points that corresponds to physical positional points of at least a portion of a patient, perform calibration of the surgical visualization camera to determine a location of crosshairs or other indicator in a space of the navigation camera and within the patient volume space, use a display of the surgical visualization camera or a separate projection device to display the crosshairs or other indicator on a portion of the patient, adjust a location of the crosshairs or other indicator based on received input from an operator, record a virtual mark in the patient volume space in response to an activation action at the adjusted location of the crosshairs or other indicator, the virtual mark being a virtual positional data point that corresponds to the physical positional point of a physical mark generated on the patient a marking pen, and cause the patient volume space of virtual positional data points and the recorded virtual mark to be displayed in an overlaid manner over live image data recorded by a surgical camera on a single display.

In a twenty-sixth aspect of the present disclosure, any of the structure, functionality, and alternatives disclosed in connection with any one or more of FIGS. 1A to 14 may be combined with any other structure, functionality, and alternatives disclosed in connection with any other one or more of FIGS. 1A to 14.

In light of the present disclosure and the above aspects, it is therefore an advantage of the present disclosure to provide an adaptive system that creates virtual marks aligned with a patient data space for camera navigation that are aligned with physical marks placed on a patient.

It is another advantage of the present disclosure to use virtual marks in conjunction with physical marks shown in images from a surgical camera to determine a shift in registration or misalignment and automatically correct the misalignment.

It is yet another advantage of the present disclosure to use natural patient features as physical marks for alignment with virtual marks for detecting and correcting patient space misalignment.

Additional features and advantages are described in, and will be apparent from, the following Detailed Description and the Figures. The features and advantages described herein are not all-inclusive and, in particular, many additional features and advantages will be apparent to one of ordinary skill in the art in view of the figures and description. Also, any particular embodiment does not have to have all of the advantages listed herein and it is expressly contemplated to claim individual advantageous embodiments separately. Moreover, it should be noted that the language used in the specification has been selected principally for readability and instructional purposes, and not to limit the scope of the inventive subject matter.

BRIEF DESCRIPTION OF THE FIGURES

FIG. 7A is a schematic model of a relative pose between a digital surgical microscope camera and a navigation camera, according to an example embodiment of the present disclosure.

FIG. 7B is a schematic model of a relative pose between a navigation target in a scene on a patient, according to an example embodiment of the present disclosure.

DETAILED DESCRIPTION

Figure 1A:
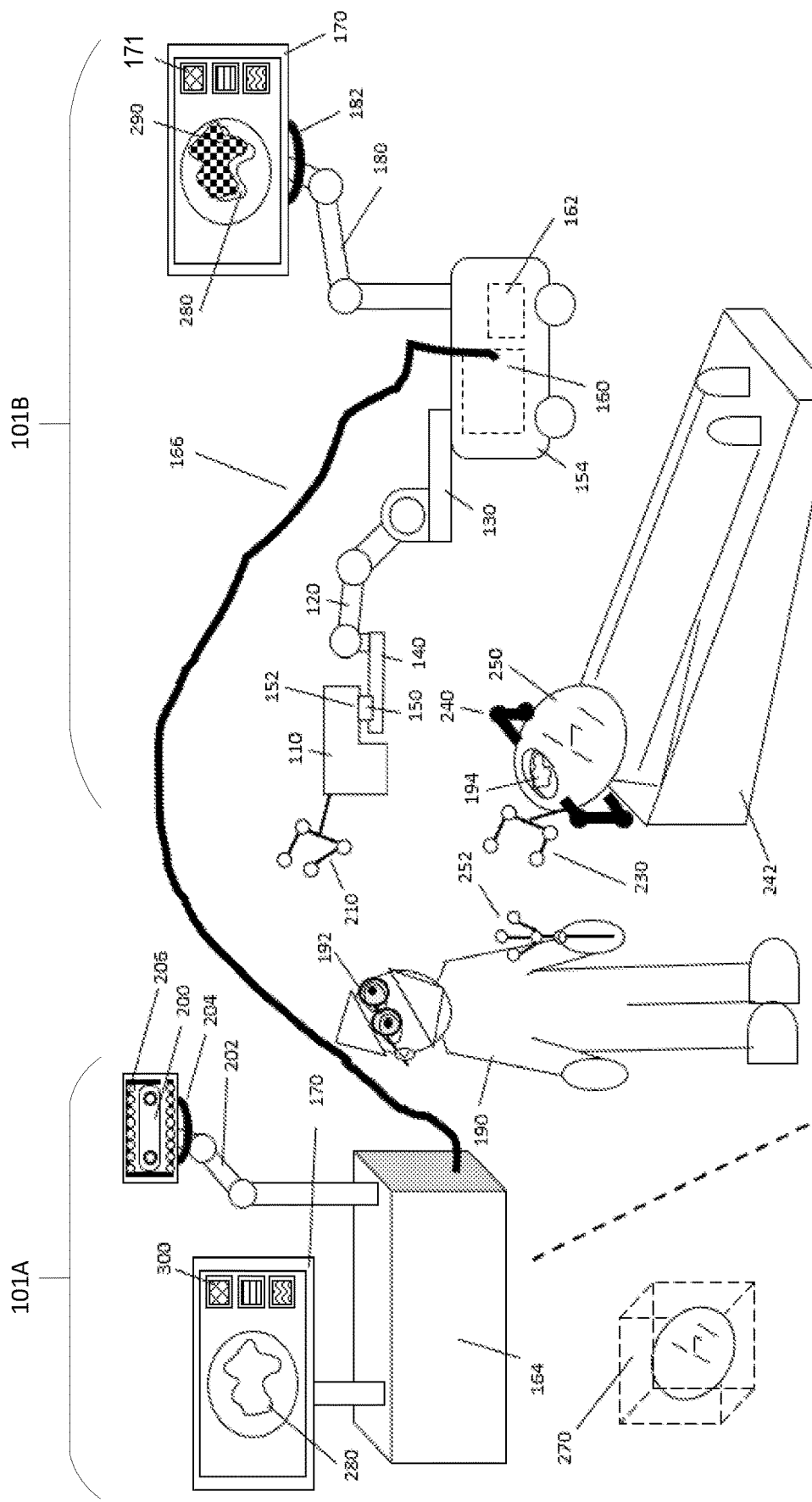
FIG. 1A is a diagram showing separate and distinct navigation and visualization systems, according to an example embodiment of the present disclosure.

The present disclosure provides a surgical marking pen, system (integrated surgical navigation and visualization system), and method that enable the recording of a patient registration in the form or real, physical marks or other such fiducials directly on the patient anatomy, which are correlated to virtual marks that are added to patient volume (scan) data or pre-operative surgical templates. The provided surgical marking pen may help enable correction of misalignment (patient degradation) due to patient draping, which is a major source of patient registration error. The provided surgical marking pen may also help enable correction of misalignment due to patient reference frame target movement. In one example, the provided surgical marking pen may help enable correction of misalignment due to microscope reference frame target movement. The provided surgical marking pen may further help enable pediatric or other "soft clamp" or non-clamping methods. For instance, marks made may provide the guideposts necessary to judge, and improve where necessary, the integrity of the registration over the course of the case.

In some instances, the physical pen marks of the marking pen may be replaced with "natural patient marks". In such embodiments, the marking pen may be omitted or used for identifying which "virtual marks" of a patient should be used. In these examples, the natural patient marks are manually or automatically identified features on a digital visualization of the patient. Natural patient marks could include skin features such as moles, or freckles, a "fingerprint" type feature such as hair follicle pattern or a skin pore pattern, or a feature of the surgery such a bone ridge in a craniometry, etc. Natural patient marks may also include three-dimensional patient anatomic features, as reconstructed from multiple views, a depth camera, and/or via a stereoscopic camera. In these examples, the natural patient marks may include skin, bone, muscle, or tissue structure. Again, these features could be manually identified with user input, or could be automatically identified by feature recognition algorithms (similar to how key points are identified in facial recognition or fingerprint identification systems). Whether the marks are placed with a physical pen, or whether they are naturally occurring features that were manually or automatically indicated, the reregistration process is configured to operate in the same manner.

In some aspects, the provided surgical marking pen is brought used after patient registration, as will be described in further detail below. The provided surgical marking pen may be used with a suitable surgical navigation system, such as, for example, the surgical navigation system disclosed in U.S. Pat. No. 10,299,880, which is incorporated herein by reference. In an alternative example, the navigation camera of the surgical navigation system may be built into the microscope head. In some examples, the provided surgical marking pen operates without a traditional navigation system.

Figure 9:
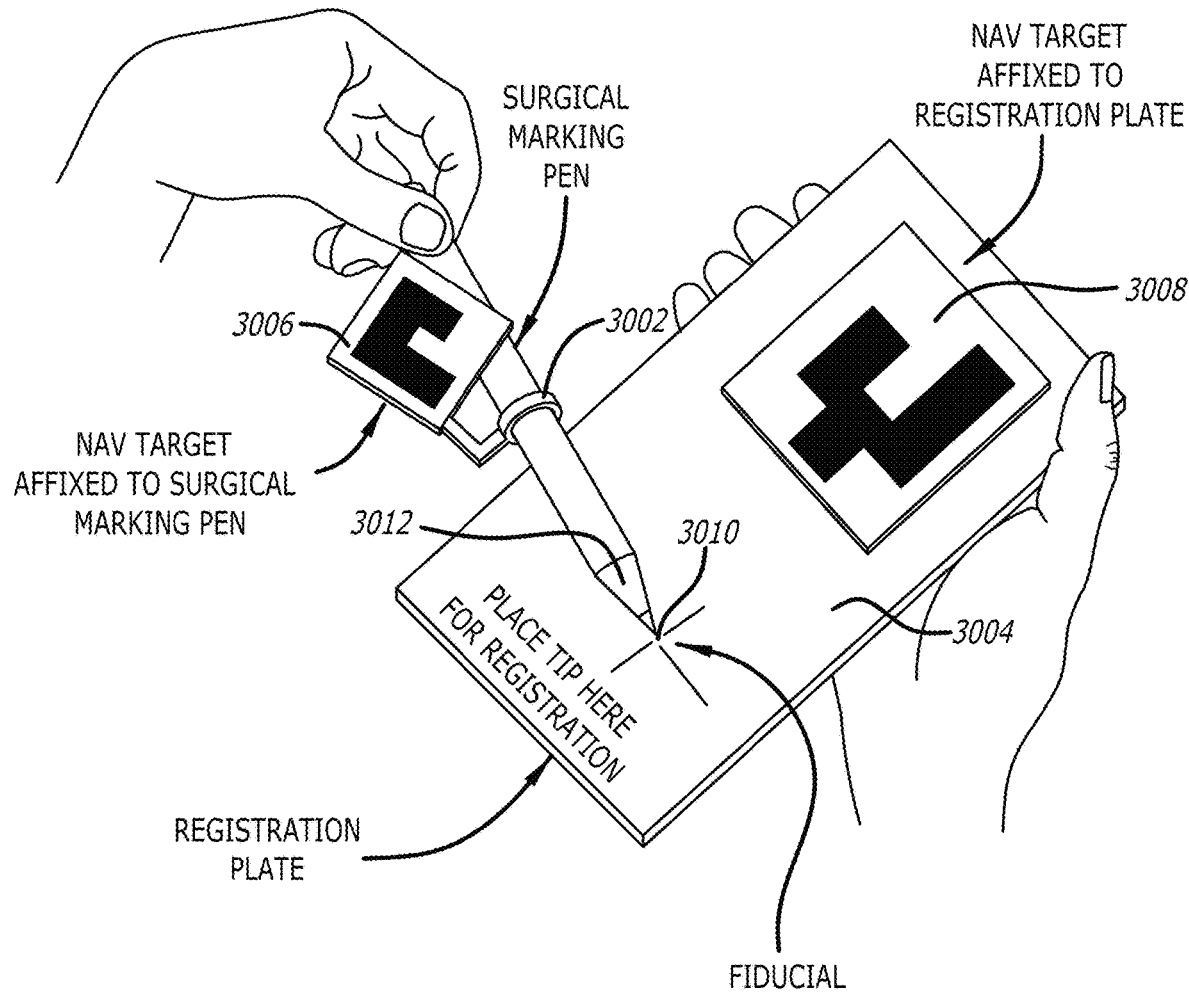
FIG. 9 is a diagram of a surgical marking pen and a marking pen registration plate that may be used with the surgical navigation and visualization system described in conjunction with FIGS. 1A to 8, according to an example embodiment of the present disclosure.

In at least some aspects, a tip of the provided surgical marking pen may be located relative to a marking pen-mounted target. In some examples, the provided surgical marking pen includes a navigation target such as the Medtronic Sure Trak™ affixed to an existing surgical marking pen such as the Viscot Industries EZ Removable Ink Mini Skin Marker Green Regular Tip Non-Sterile™ pen or the Viscot Industries Value Regular Tip Marker™ pen. In such examples, the location (and optionally orientation) of the pen tip relative to the navigation target affixed is found using a marking pen registration plate, as shown in FIG. 9, in conjunction with a computation algorithm implemented in the system's information processor module.

As described herein, the surgical marking pen is used in conjunction with an integrated surgical navigation and visualization system, which include a single and/or centralized computer system. For example, the visualization and the surgical navigation software modules may be resident within, and execute inside, the same computer, thereby reducing communication latency and connectivity risk. This arrangement may eliminate the need to position multiple pieces of equipment in an operating room which might have limited space. The tighter footprint and elimination of remote and/or separate localizer modules may ease line-of-sight problems.

The integrated surgical navigation and visualization system may help provide navigation information overlaying the live surgical view in stereoscopic view at the same plane of focus for all views. This arrangement may alleviate the problem of the surgeons having to refocus their eyes as they look from live surgical site to overlay. Furthermore, the integrated surgical navigation and visualization system may eliminate interference of navigation infrared (IR) light source with fluorescence light source(s). Microscope fluorescence and navigation light may typically use same or similar light wavelengths, limiting the usability and efficacy of the fluorescence.

Furthermore, the integrated surgical navigation and visualization system use drawn user-planned virtual incision and/or other approach patterns and/or paths in conjunction with the virtual marks that are added to surgical templates and/or patient volume scan data. For example, the integrated surgical navigation and visualization system enables an operator to draw user-planned virtual craniotomy plans as a pre-surgical template. The integrated surgical navigation and visualization system disclosed herein stores the drawn virtual craniotomy plans in conjunction with virtual marks. The integrated surgical navigation and visualization system compares the virtual marks to the drawn physical marks or natural patient marks to determine if there is misalignment between the patient anatomy shown in the live view and the virtual marks. If there is misalignment, the integrated surgical navigation and visualization system re-registers the virtual marks and virtual craniotomy plans with the patient anatomy shown in the view. In another example, the integrated surgical navigation and visualization system may enable an operator to draw user-planned trajectory plans, which may persist optionally under control of the user throughout the time of the surgical approach. Such guidance may also be updateable, e.g., to correct any errors as the procedure progresses using the automatic registration methods disclosed herein.

I. Surgical Environment

Figure 1B:
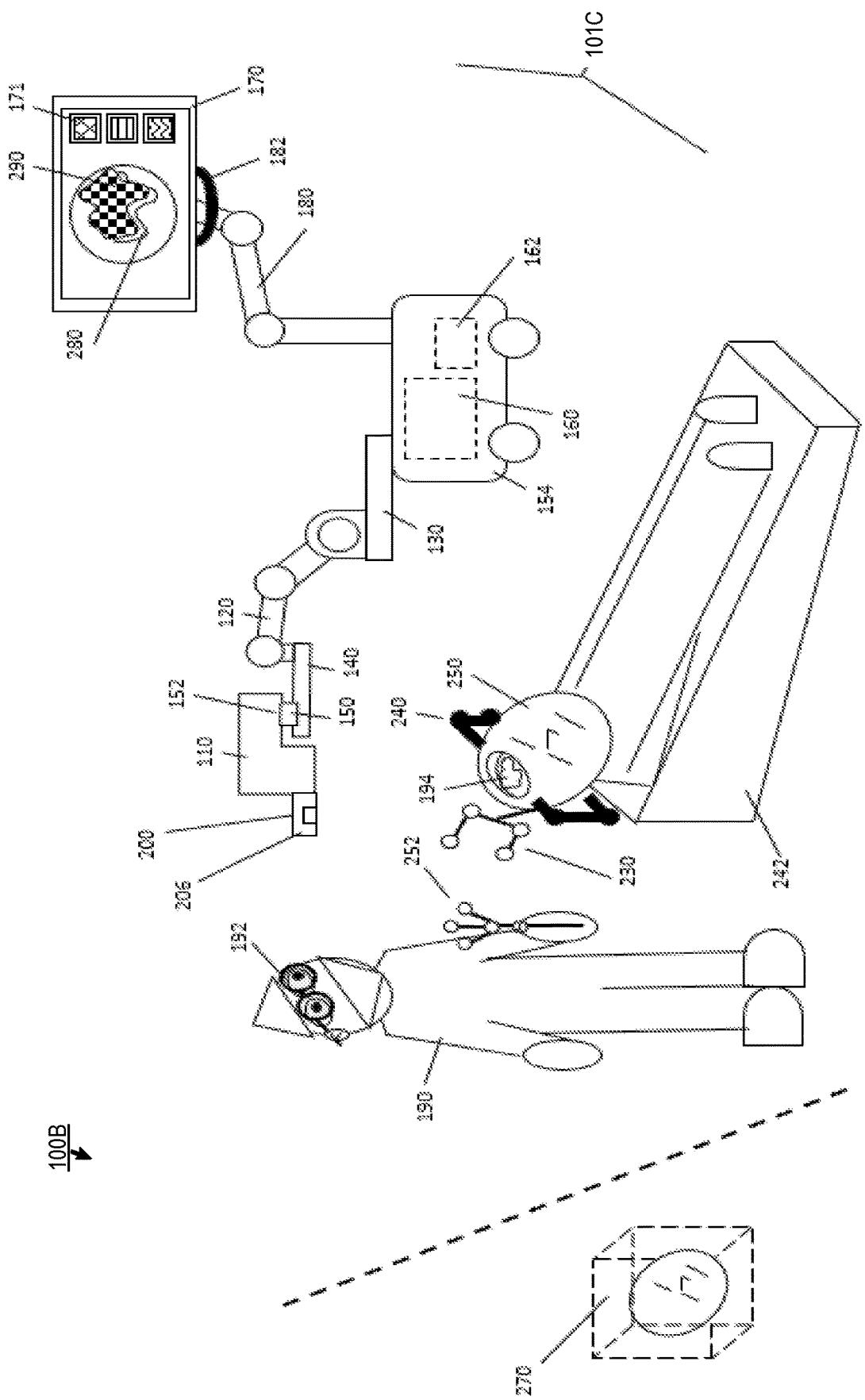
FIG. 1B is a diagram showing an example surgical environment of the integrated surgical navigation and visualization system with auto-navigation, according to an example embodiment of the present disclosure.

FIG. 1A is a diagram showing separate and distinct navigation and visualization systems, e.g., as used in some surgical environments 100A. In contrast, FIG. 1B is a diagram showing an example surgical environment 100B of the integrated surgical navigation and visualization system, according to an example embodiment of the present disclosure. As shown in FIGS. 1A and 1B, the example surgical environment 100B of the present disclosure includes the integrated surgical navigation and visualization system 101C, whereas the environment 100A typically includes a surgical navigation system 101A separate and distinct from the surgical visualization system 101B. In some aspects, the separated surgical navigation system 101A and the surgical visualization system 101B may be communicatively connected via cable 166, providing limited options for augmented reality during surgery. The integrated surgical navigation and visualization system 101C of FIG. 1B and/or the surgical visualization system 101B of FIG. 1A may include a digital surgical microscope (DSM) head 110 mounted on a robotic arm 120. To enhance robotic arm reach, the robotic arm 120 may be mounted on an extension platform ("diving board") 130. To extend the range of orientations in which the integrated surgical navigation and visualization system can be used, the DSM head 110 can be mounted on a "universal" coupler 140, which may provide one or more additional degrees of freedom beyond the end of the robotic arm.

In some embodiments of the present disclosure, a force-torque sensor 150 may be incorporated into the robotic arm-DSM head combination (e.g., of the integrated surgical navigation and visualization system 101C). The force-torque sensor 150 may allow users to pose the DSM head at will using physical actions (e.g., as legacy microscopes). For example, the user can physically grab some part or parts of the DSM head or handles attached or otherwise coupled to the robotic arm, and can direct the head toward the desired pose. The force-torque sensor 150 can detect the physical input. A software control module can convert the force-torque sensor's output into an intended change in pose. The same or an additional control module can convert such user intent into a set of robot pose changes that can be streamed to the robot to effect the changes.

The integrated surgical navigation and visualization system 101 and/or the surgical visualization system 101B may further include a cart 154. The cart 154 can provide a support structure for the robotic arm and diving board. Furthermore, the cart 154 may include an embedded processing unit (EPU) 160 and power management unit with uninterruptible power supply (PMU/UPS) 162. The EPU 160 includes a processor that is in communication with a memory that stores machine-readable instructions. Execution of the machine-readable instructions by the processor causes the EPU 160 to perform the operations described herein.

The EPU 160 can communicate with the DSM head, sending commands and receiving command responses and image and status data. The PMU/UPS 162 can manage power for the system 101. The uninterruptible power supply (UPS) 162 can provide the user with the option to unplug the cart for a short time to reposition if needed. The PMU/UPS 162 can also provide the surgeon with an option to have a short time to transition to backup equipment should the hospital power fail.

Imagery can be captured by the digital surgical microscope's optics and image sensor electronics (not shown), sent to the EPU, processed and sent to the three-dimensional (3D) stereoscopic display 170. The 3D stereoscopic display 170 may be mounted on an articulated display mounting arm 180, and its pose may be controlled by display pose adjustment handle 182 e.g., to allow the user to pose the display for optimal viewing quality and comfort.

The surgeon 190 may wear 3D glasses 192 to view the 3D stereoscopic display. The 3D glasses 192 may provide the surgeon to view a 3D stereoscopic view of surgical site 194. Zoom and focus optics in the digital surgical microscope can be controlled by the user, and can provide 3D stereoscopic focused views of the surgical site over a range of working distances (e.g., 200 millimeters (mm)-450 mm) and magnifications (e.g., 3×-11×). In some embodiments the 3D glasses are passive wherein the polarizing film on each respective lens of the glasses left and right are respective conjugates to polarizing film applied to every other line on the display (e.g. the left glasses lens passes the even-numbered lines of the display and block the odd-numbered lines, and vice-versa). In some embodiments, the 3D glasses are active shutter types synchronized to the display such that the left eye passes e.g. every other time-sequential frame shown on the display and blocks the remainder and the right eye performs the complement. In some embodiments, the 3D display may be "glasses-free" and may provide 3D display to the user without need for 3D glasses.

As used herein, "working distance" and "focus" may be used interchangeably. Furthermore, the user interface of the integrated system 101C may refer to working distance as the variable parameter. When a change is made to the desired working distance, the optics move such that the focus distance changes. Thus, the distance between the microscope and the focus surface may change, and that distance can be generally considered to be the working distance.

The integrated surgical navigation and visualization system 101C and/or the surgical navigation system 101A may include a navigation camera ("navigation localizer" or "localizer") 200. For example, in the surgical navigation system 101A shown in FIG. 1A, the navigation localizer 200 may be mounted on the articulated localizer mounting arm 202. The navigation localizer 200 may be user-poseable by localizer pose adjustment handle 204.

A navigation-trackable patient reference target 230 can be mounted rigidly to a patient clamp (e.g. a "Mayfield" clamp) 240. The patient clamp 240 may be mounted near surgical bed 242 where the patient 250 resides. The patient clamp 240 may avoid areas of the patient's anatomy to move in relation to the patient reference array.

The digital surgical microscope may be rendered to be compatible with (e.g., by being rendered trackable by) the localizer with the addition of the DSM navigation target (e.g., "shellmet," as derived from "shell" and "helmet.") 210. Various styles of navigation targets can be used with the system such as the retro-reflective spheres shown schematically in the Figure or image-based corner targets described elsewhere in this document.

The localizer may detect the pose in some reference frame of compatible devices (i.e. trackable devices, navigation targets) in its viewing space. The localizer may supply this information to the EPU responsive to requests for such information in a quasi-real-time fashion (e.g., 15 times per second in a "polling" method) or at a constant rate even without requires (a "broadcast" method). Typically, the reference frame in which the poses are reported may be that of the localizer. In some implementations, however, precalculations may be performed in order to report the poses from a different reference frame.

Relevant rigid patient anatomy such as the skull may be mounted to or accessible via, clamp 240. Systems and methods described herein may guide the user through a patient anatomy registration procedure, as part of the preparation workflow. This registration procedure can determine the pose of the patient data 270 relative to the navigation target affixed rigidly either directly or indirectly to the relevant patient anatomy.

In some aspects, the integrated surgical navigation and visualization system 101 may comprise a navigation system integrated into the DSM head 102, which may be mounted on robotic arm 120. The cart 154 may support the robotic arm 120 as well as a boom-mounted 3D stereoscopic display (e.g., 3D stereoscopic display 170) and a mast-mounted touchscreen 171 for user input. Additional displays can also be connected optionally.

The integrated surgical navigation and visualization system 101 may provide 6 degree of freedom (6DoF) position and orientation information of the head relative to some reference or target viewable by the navigation device in the scene. The digital surgical microscope may provide stereoscopic visualization over a range of magnifications (typically 1×-9×) and a range of working distances (typically 200 mm-450 mm.)

An objective of surgical navigation may include guiding the surgeon around the patient's anatomy during a surgical procedure so that the surgeon can complete the procedure in the most effective, least damaging way. The patient's anatomy has typically been scanned in a device such as a computed tomography (CT) machine or a magnetic resonance imaging (MRI) machine, and the results may be stored in a format such as a stack of image "slices" of the anatomy from which the 3D anatomy can be reconstructed and explored. The above described objective can thus achieved by providing a view or views of various levels of relative position and orientation information between the patient data and various objects such as a navigation probe and/or the digital surgical microscope's optical axis.

II. Levels of Navigation Complexity

There may be various levels of complexity for surgical navigation, each with increased costs and benefits. Each level of complexity may involve increased complexity in camera calibration while each proving more navigation information (or more readily used such information.)

A simple form of navigation may be to provide in such a view the location in the patient data of a single point such as the tip of a navigation probe. The next level of complexity may involve showing a vector in the data, where the vector may represent the line along which the axis of the navigation probe lies. The next level of complexity may include showing the correct orientation of the probe about that vector.

At higher levels of complexity, surgical navigation may be integrated with visualization. For example, the next level of complexity may be to provide vector with orientation for a digital surgical microscope, with the probe vector becoming the optical axis of the microscope. The probe tip may become a focal point of the microscope, and the orientation information may pertain to the "up" direction of the onscreen display of the microscope (e.g. the vertical dimension of the microscope display.) At this level of complexity, a view of a given two-dimensional "slice" of the patient 3D data largely similar to the onscreen live view of the digital surgical microscope is possible.

A higher level of complexity for navigation achieved in various embodiments described herein is to overlay a rendering of such a two-dimensional "slice" of the patient scan data over the live microscope image, and have visible features of the rendering align to their corresponding features in the live view to some level of accuracy and to enable movement of the "slice" along the optical axis, for purposes of "x-ray vision" to view structures beneath the current physical surface of the patient's anatomy. An even higher level of complexity for navigation also achieved in various embodiments described herein is to provide a three-dimensional rendering (albeit to the two-dimensional display) of the patient scan data over the live view, and have corresponding features align.

III. Determining the Relative Pose of an Object and the Patient Anatomy

Each level of complexity of surgical navigation may involve a determination of relative position and/or orientation of one object relative to another. In one embodiment, the highest level of surgical navigation complexity described herein may comprise all the described levels of complexity. Therefore, for ease of explanation, the highest level is described (e.g., via FIG. 1C).

Figure 1C:
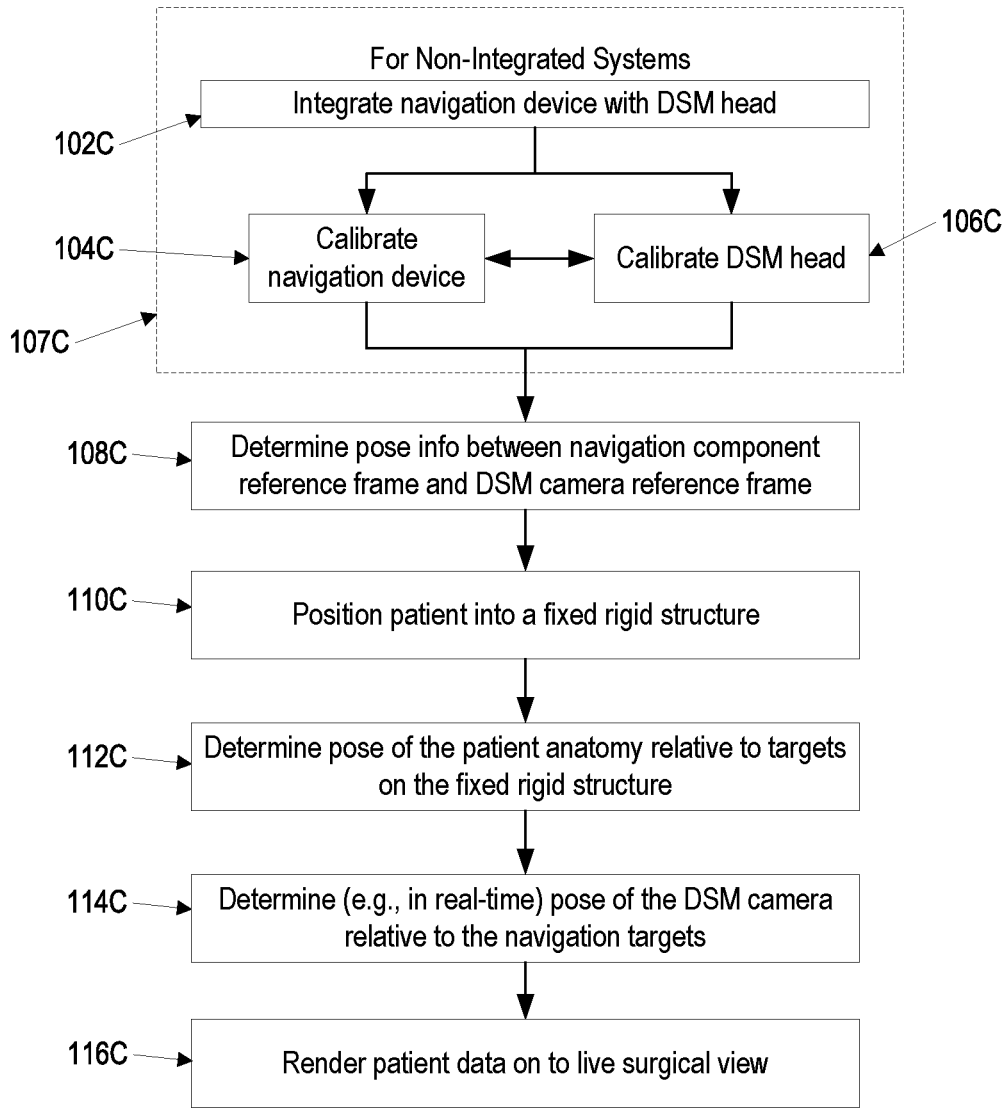
FIG. 1C is a flow diagram showing an example process for determining the relative pose of an object and the patient anatomy (e.g., in an integrated surgical navigation and visualization system), according to an example embodiment of the present disclosure.
Figure 1D:
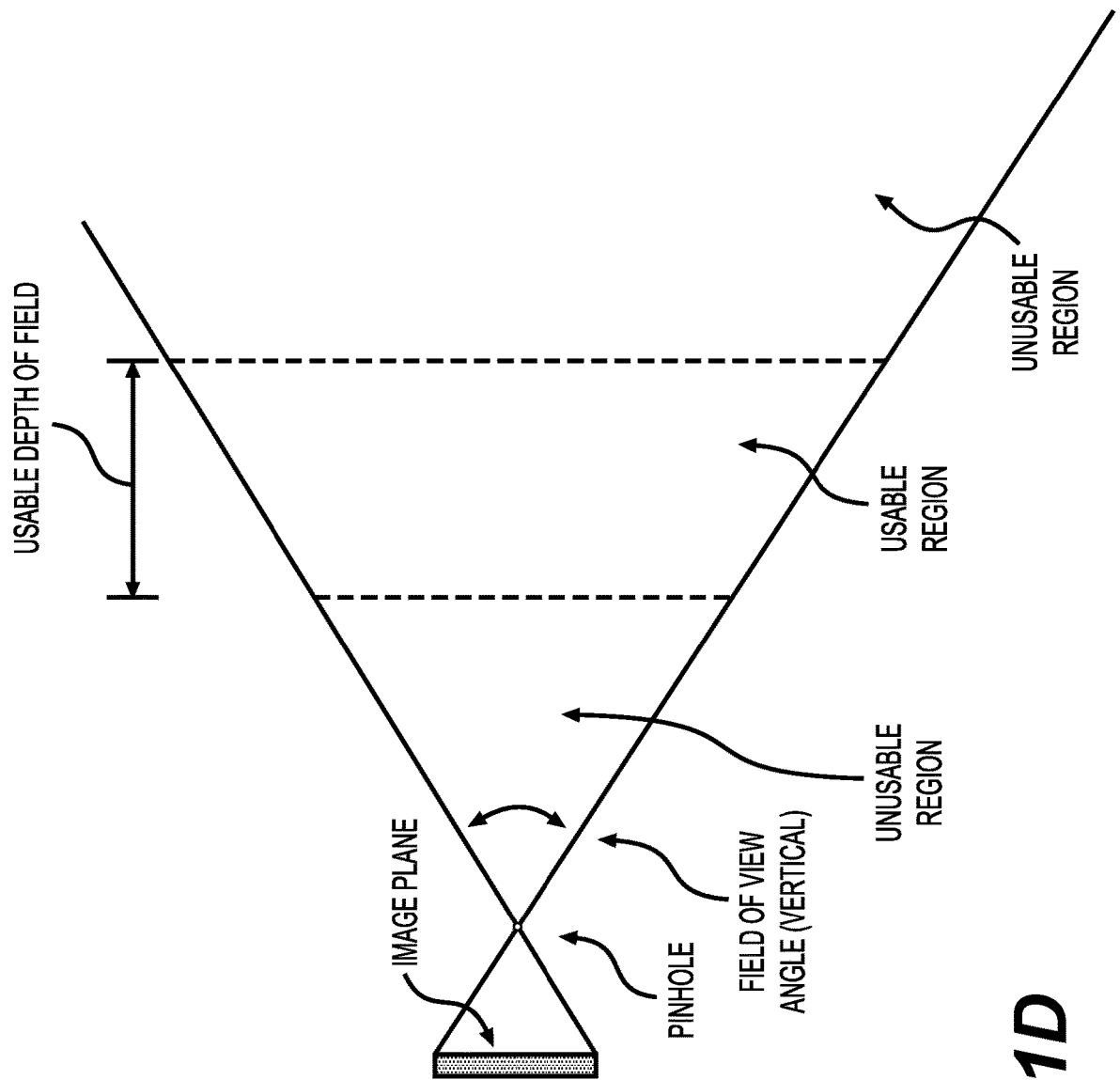
FIG. 1D is a diagram showing an example pinhole camera vertical field of view angle, according to a non-limiting embodiment of the present disclosure.

FIG. 1C is a flow diagram showing an example process 100C for determining the relative pose of an object and the patient anatomy (e.g., in an integrated surgical navigation and visualization system (e.g., a high level of complexity)), according to an example embodiment of the present disclosure. In one embodiment, process 100C may begin with integrating a navigation device into the digital surgical microscope head (102C). Furthermore, the navigation device and the digital surgical microscope camera(s) may each or collectively be calibrated (steps 104C and 106C, respectively). However, as systems that already integrate surgical navigation and visualization are described herein, steps 102C through 106C may be optional (e.g., as shown by marker 107C. For integrated surgical navigation and visualization systems, process 100C may begin at a subsequent step shown in FIG. 1C.

For example, process 100C may begin with the navigation component of the integrated surgical navigation and visualization system determining the relative position and orientation information (also known as "pose" information) between the navigation component reference frame and the reference frame of the digital surgical microscope camera(s) (step 108C). This step may be optionally combined with calibration steps previously described.

The patient may be positioned into a fixed rigid structure such as a clamp (step 110C). The targets on the clamp may be provided with poses, such that the targets may be detectable in real-time or near real-time by the integrated surgical navigation and visualization system and associated methods.

The pose of the patient anatomy in the preoperative, perioperative and/or intraoperative (typically 3d) patient data scan relative to the target(s') reference frame(s) on the fixed rigid structure (e.g., clamp) may be determined (step 112C). By including a calibration target fixed rigidly to the patient clamp, this step may be optionally combined with the determination of relative pose between the navigation device reference frame and the reference frame of the digital surgical microscope camera(s). Also or alternatively, step 112C may be combined with the calibration of the digital surgical microscope camera(s). The calibration target may be used as a navigation target.

At step 114C, the pose of the DSM camera relative to the navigation targets may be determined (e.g., in real time or near-real-time). For example, the navigation component of the integrated surgical navigation and visualization system may be used to view the targets on the clamp in real-time or near real-time to provide the latest pose of the digital surgical microscope camera(s) relative to the navigation targets. Thus, using data collected in the previous steps, the pose of the digital surgical microscope camera(s) relative to the patient data may be calculated.

At step 116C, the patient data for use by the surgeon may be rendered with the varying levels of surgical navigation complexity described previously either alongside or overlaid onto the live surgical view.

IV. Navigation Device

The navigation device may provide 6 degree of freedom (6DoF) position and orientation information of the head relative to some reference or target viewable by the navigation device in the scene. The navigation device may be realized using a standard imaging device such as a USB webcam. This monoscopic camera may be used to view the scene and provide the scene image in digital form to a main information processor module which uses standard image processing techniques to detect all of the navigation targets present in the scene. Further standard image processing techniques may be used to calculate the 6 DoF position and orientation information of the given navigation target relative to the camera reference frame.

The resolution of the camera(s) used in the navigation device may affects accuracy. For example, a higher resolution camera can provide higher resolution position and orientation measurements for a given measurement space compared to a lower resolution camera. The measurement space may be measured at a higher spatial frequency. For example, a camera using an image sensor with 1920 pixels in the horizontal direction measuring a space that is 1.92 meters (1920 mm) wide will sample that space at 1920 pixels/1920 mm=1 pixel per mm. A camera with sensor having 3840 pixels in the horizontal direction will sample that space at 3840 pixels/1920 mm=2 pixels per mm. When optics are designed correctly to match the sensor pixel size, this space-sampling resolution increases directly proportionally with the resolution of the sensor used in the camera.

Sub-pixel resolution techniques such as used in OpenCV::cornerSubPix( ) can dramatically improve this resolution for a lower resolution camera and known (or algorithm-friendly) target patterns but can also be used for the higher resolution camera, thereby retaining the advantage of the higher resolution camera.

The field of view of the navigation camera as used here means the angular span viewable by the camera in both the horizontal and vertical directions. The usable region within that three-dimensional region relates to the depth of field of the camera optics in which items are enough in focus to be usable; we might use the term "depth of field" for this definition of usable region, which may differ slightly from traditional imaging because the target detection computer vision algorithms can often use images successfully that are blurrier than might be considered usable by a human viewer.

The field of view may need to be large enough to accommodate all uses of the device; the navigation targets may be required to be in view at all times. Additionally, workflow requirements dictate that the system support use of tools that are typically used without the microscope viewing them, such as a navigation probe. Such a probe is used after patient registration to the navigation system, before the patient is opened, to determine the optimal surgical approach. Some systems require the use of the probe to perform the registration step. The navigation system of the present application offers an improvement over using a probe for registration.

The prevailing and most straightforward method of modeling an optical system for camera calibration is the pinhole model in which the camera is modeled as a simple pinhole camera. However this does not fully match a real system because a pinhole camera has an infinite depth of field. That is, every object in the scene is always in focus regardless of its distance from the camera. In a real camera there is a usable region in the field of view in which objects are sufficiently in focus; objects outside of that range are too blurry for use.

FIG. 1C is a diagram showing an example pinhole camera vertical field of view angle, according to anon-limiting embodiment of the present disclosure. As shown in FIG. 1C, the vertical field of view angle includes usable region relating to the depth of field.

A trade space is constructed to determine the optimal values of field of view, depth of field, and camera resolution for the application. Each affects the usability of the system and the measurement accuracy of target position and orientation, and camera resolution directly affects the cost of goods and computational load.

To increase robustness of the system, a light source such as pulsed LEDs is optionally added to the navigation camera device. The lighting faces the scene and is only seen by the navigation camera when it reflects off of items in the scene, particularly the navigation targets. Optical filtering is optionally added in front of the camera lens (and optionally in front of the LEDs) which filters are matched to the wavelengths of the lighting used such that light outside the desired spectrum is rejected.

Additionally, the lighting is optionally pulsed in a pattern synchronized to the navigation camera sensor such that the camera can reject spurious background lighting. For example the LEDs are turned OFF for the exposure time of the even frames of the navigation camera (frame 0, frame 2, frame 4 etc.) and turned OFF for the odd frames (frame 1, frame 3 and so on), then then an OFF frame is subtracted from its nearest ON frame (for example the ON frame that arrived just prior) . . . this "background suppression via light synchronization method" suppresses background lighting and shows largely only the reflections of the LED light source.

This method suffers from the problem of reflection of the LED light source from objects other than the navigation targets. However, with image processing to detect the a priori known target patterns from the resultant navigation cam images, this method still works sufficiently.

Further robustness is achieved by optionally using targets that fluoresce in one region of the electromagnetic spectrum upon stimulation by energy from a different region of the spectrum: The light source and any required optics and optical filters for the light source are designed to generate and project to the scene the stimulation region of the spectrum; the targets are designed to absorb this stimulation and emit the emission region of the spectrum; and the optical filter in front of the camera is designed to pass just the emission region of the spectrum. When used with the "background suppression via light synchronization method" described above, the resultant navigation camera image contains largely only images of the navigation targets; reflections of the navigation LED light stimulation from objects other than the navigation targets are suppressed considerably.

V. System Pipeline

Figure 2:
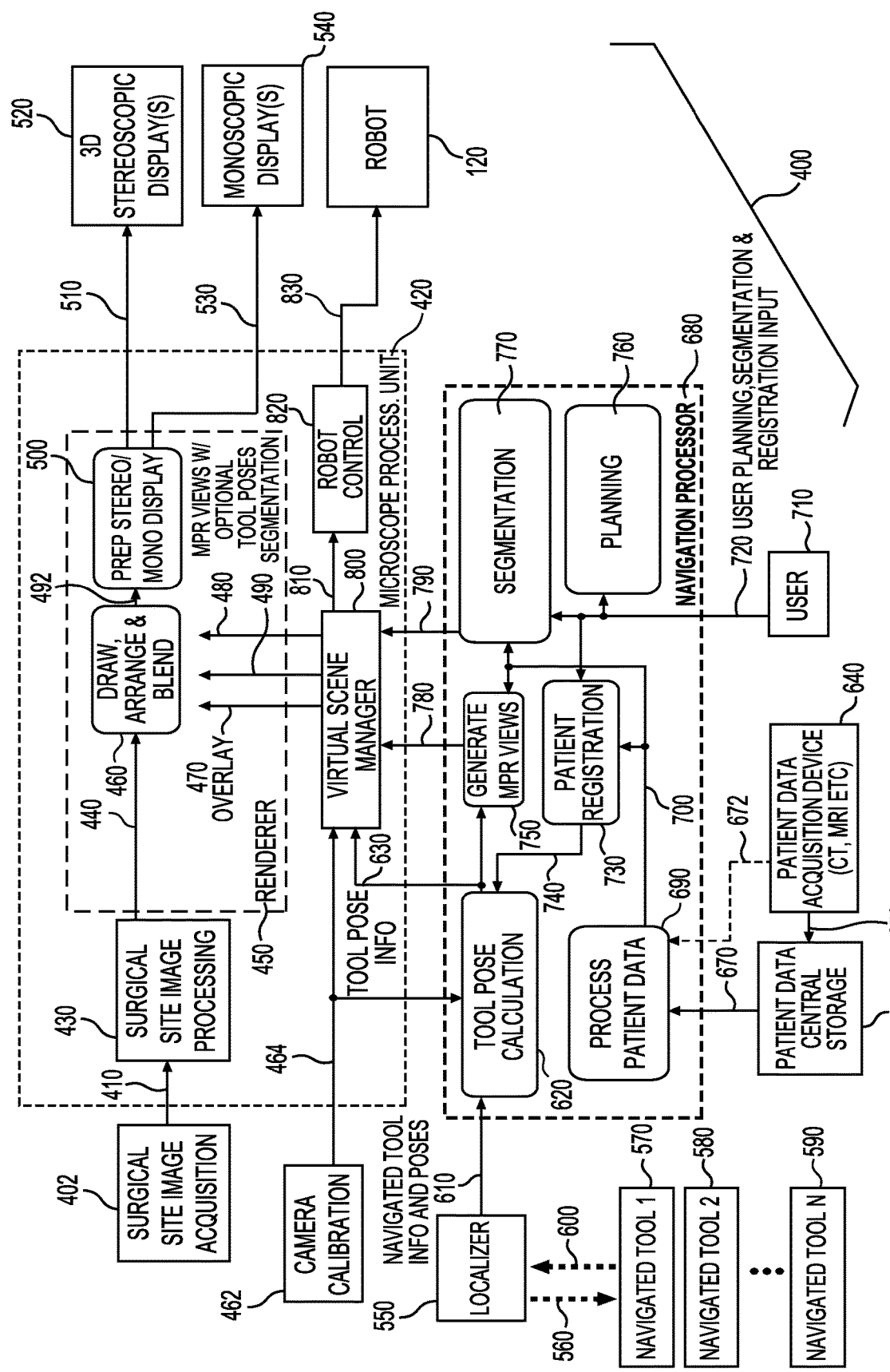
FIG. 2 is a flow diagram showing an example pipeline for the integrated surgical navigation and visualization system, according to an example embodiment of the present disclosure.

FIG. 2 is a flow diagram showing an example pipeline 400 for the integrated surgical navigation and visualization system, according to an example embodiment of the present disclosure. Furthermore, pipeline 400 describes one or more examples of how surgical visualization and navigation information is generated, captured, processed and displayed in the integrated surgical navigation and visualization system 101. It is understood that while the processes associated with pipeline 400 are shown as near-linear, one or more processes can happen concurrently and/or in a different order than is presented here.

Pipeline 400 may begin with image acquisition of a surgical site (block 402) (e.g., as part of an image data stream). The surgical site image acquisition may occur at or be performed by a surgical site image acquisition module. An example image acquisition module of a fully featured stereoscopic digital surgical microscope, including light source(s), zoom and focus optics, image sensors and all supporting electronics, software, firmware and hardware, is further described in U.S. Pat. Nos. 10,299,880 and 10,334,225, the entireties of which are hereby incorporated by reference herein. This image acquisition module may generate surgical site image data stream 410, which may be communicated to microscope processing unit 420 and the associated surgical site image processing module 430. Images may be captured and processed at a frame rate high enough to be perceived as video by the user, for example, frames per second (fps.). Thus, images may be considered to be "image data stream." It is to be understood that, where a two-camera stereoscopic digital surgical microscope is described, the concept may be extendible to an N-camera digital surgical microscope where N is 2 or greater.

The surgical site image processor may process the image data 410 received from the surgical site image acquisition module, and may produce processed image data stream 440.

The processed image data stream 440 may be sent to the renderer module 450, and more specifically to the draw, arrange & blend module 460. The renderer module 450 may also receive camera calibration information 464, which may be generated in an offline process. Methods and systems for producing camera calibration information are further described in U.S. Pat. Nos. 9,552,660 and 10,019,819, the entireties of which are hereby incorporated by reference herein. Camera calibration information may be generated for each "eye" of the stereoscopic digital surgical microscope. The camera calibration may provide the renderer module with the option to set up its virtual cameras such that, along with proper navigation data to be described, rendered overlay objects appear in similar perspective, size (magnification) and pose as objects captured by the surgical site image acquisition module. For example, the rendered overlay of a portion of a patient's skull and skin may appear in a similar perspective and pose as a live view of the same portion through the digital surgical microscope.

Such combination may continue in the draw, arrange & blend module 460, where surgical site processed image data stream 440 may be combined with patient data overlay 470, multiplanar reconstruction (MPR) views with optional tool poses 480, and segmentation information 490 into a raw stereoscopic rendered image stream 492. The raw stereoscopic rendered image stream 492 may be sent to the stereoscopic/monoscopic display preparation module 500. The stereoscopic/monoscopic display preparation module 500 may transform the raw stereoscopic rendered image stream 492, as necessary, into the final stereoscopic display output data stream 510 required by the stereoscopic display(s) 520. Different stereoscopic displays may require different final stereoscopic data formats, which the display preparation module may provide. Also or alternatively, there may be one or more monoscopic displays 540. The various data formats 530 associated with the monoscopic displays 540 may also be provided via configuration by the display preparation module.

The preceding few paragraphs discuss the acquisition of a live surgical site image stream, its processing and combination with navigation module output and the display thereof. The navigation module output is formed as follows.

The localizer 550 may comprise a sensing device having a certain scene visible to its field of view. The scene may depend on the design of the device and pose of the device. In some embodiments, the localizer 550 may send a communicative query 560 to one or more navigated tools. The navigated tools, which might be present in the scene, may include, for example, a first navigated tool 570, a second navigated tool 580, and/or up to a certain number of such tools 590. Such a communicative query in some embodiments may involve directing infrared light either at a constant level or in a known pulse rate and/or sequence toward the scene. In some other embodiments, the query may be of a passive nature, such as relying on ambient visible light to illuminate a high-contrast pattern formed on the navigated target(s). Control of this infrared light (e.g., by switching on and off, or by selecting a specific wavelength) may help avoid illumination interference with the digital surgical microscope fluorescence capabilities.

The communicative query may be sent back as a response 600 from each respective navigated tool. The response may be received by the localizer, and may be sent as tool information and pose information 610 for each navigated tool. The localizer may run these query and/or responses as send/receive cycles at real-time or near real-time rates such as 15 Hertz (Hz) to 30 Hz. The pose information for each tool may be determined in a common space for all tools. For example, a coordinate reference frame origin and orientation relative to a rigid feature of the localizer may be the common space that is used. The tool and pose information 630 may be received by tool pose calculation module 620.

In an offline process, a patient data acquisition device (CT, MRI, etc.) 640 may be used to scan the relevant anatomy of patient 250 to generate acquired patient data 650. The acquired patient data may be optionally stored in a patient data central storage 660. The patient data may be sent (e.g., from the central storage 670) to the navigation processor 680. Alternatively, the patient data may be sent to said processor as patient data 672 directly from acquisition device 640.

It is understood that the physical location of each navigation processor, the microscope processing unit and all other main components may vary with implementation. Generally, the microscope processing unit 420 and the navigation processor 680 may reside in the embedded processing unit 160, but this is not a requirement. For example, the navigation processor might be physically located inside the same housing as the navigation camera, remote from the cart which might house the embedded processing unit.

The patient data processing module 690 may process the patient data into format(s) needed by various modules in the rest of the system as processed patient data 700.

Figure 4:
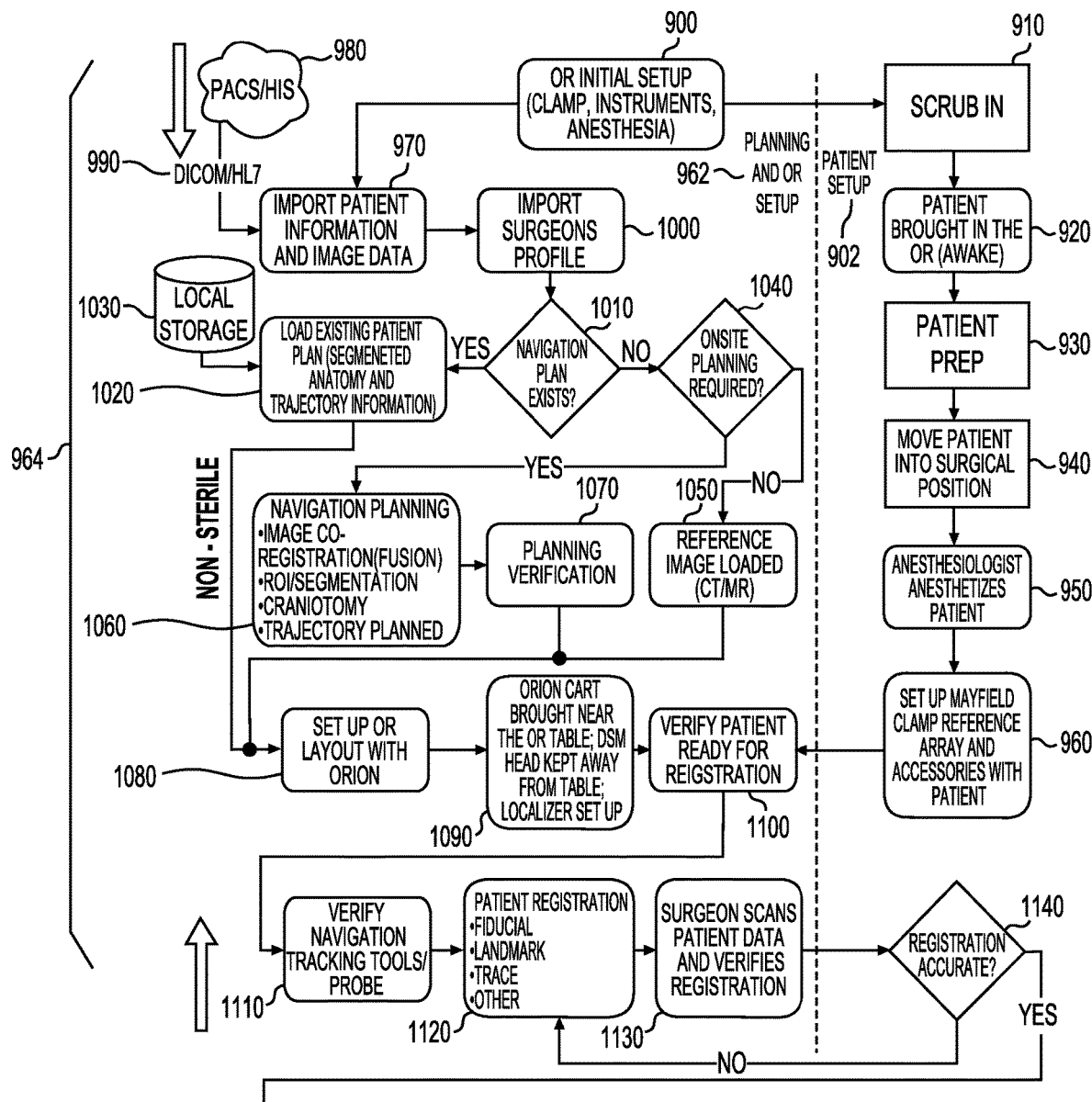
FIG. 4 is a flow diagram showing an example workflow performed for the integrated surgical navigation and visualization system, according to an example embodiment of the present disclosure.
Figure 4:
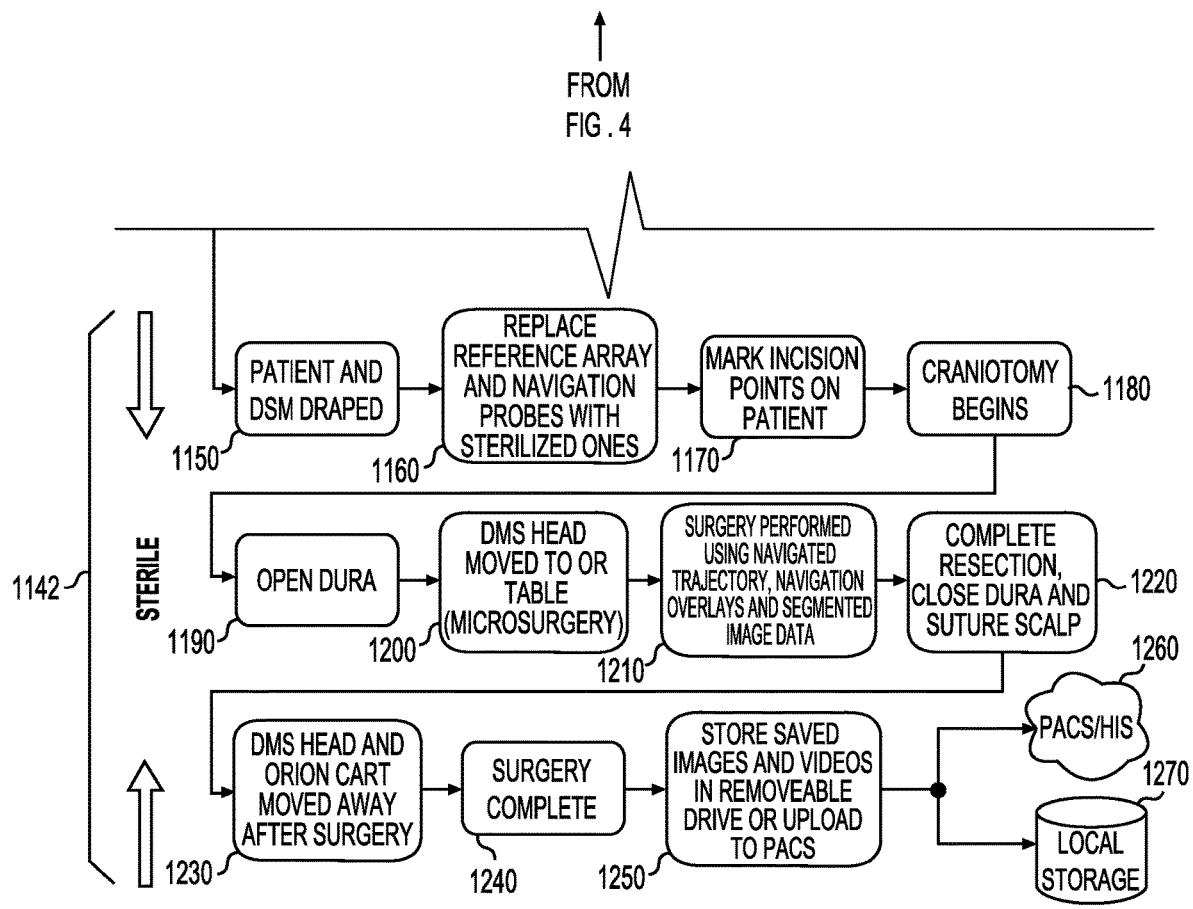

The relative timing of processes associated with this pipeline is further described in relation to FIG. 4. As will be described below, the user 710 may direct the software via user planning, segmentation and registration input 720 to perform those respective workflow steps. The patient registration module 730 may direct the user and accept user input to generate patient registration information 740. The registration information 740 may describe the pose relation between the processed patient data 700 and the patient reference navigation target 230.

Use of the processed patient data 700 may continue as the multiplanar reconstruction view generator 750 generates multiplanar views 780. The multiplanar views 780 may assist the user in the use of the planning module 760 to generate opening, approach and objective patterns and trajectories (as standard features in surgical navigation systems). In some embodiments, a 3D view generator may further assist the user in such endeavors, e.g., by generating a 3D representation of the patient data. The view of the 3D representation can be adjusted based on a desired pose and/or scale.

The multiplanar views 780 and/or any 3D representation of the patient data may assist the user in use of the segmentation module 770 to generate segmented geometry 790. For example, if the patient pathology is a tumor located in some certain location of the patient's brain, the segmentation module 770 provides the user the option to isolate the tumor in the patient data such that the segmented geometry represents the tumor in size, shape and pose.

One or more of the camera calibration information 464, tool pose information 630, multiplanar reconstruction views 780, 3D representation of the patient data, and segmented geometry 790 may be provided to the virtual scene manager 800. The virtual scene manager 800 may generate representations of the patient data overlay 470, multiplanar reconstruction views with optional tool poses 480, and segmentation information 490 usable by the draw, arrange & blend module 460 in various ways, as configured by the user.

For example, the overlay may be displayed at a distance along the optical axis of the digital surgical microscope, with an on/off option available. Also or alternatively, said distance along the optical axis is may be controllable by the user, allowing an "X-ray vision" of patient data beneath some portion of the patient anatomy.

In existing conventional systems, where the overlay is injected into traditional optical microscopes, the focal plane of the overlay display is distinctly one single plane whereas the view of the scene is an analog collection of many focal distances. In such conventional systems, users are often forced to refocus their eyes when switching between viewing the live surgical site and viewing the overlay. Further the perceived location of that one single overlay display plane is often located significantly away from the general surgical site scene, for example a few centimeters above the site. However, systems and methods described herein may allow the overlay information to be presented on the same display focal plane as the stereoscopic view of the live surgical site.

While there may be a single display focal plane of the stereoscopic view of the live surgical site (e.g., the plane of the stereoscopic display), the user may still perceive a full or perceptually full analog collection of many focal distances owing to the wonders of the human visual system.

Further to the example, one or more (or all) of the three multiplanar reconstruction views plus a 3D representation may optionally be displayed at the side of the main display screen, thereby integrating, in one display, the live surgical view along with the navigation information. This integration is yet another benefit over existing multi-device systems, which often force the user to look back and forth between the visualization system and the navigation system, mentally carrying a large informational load between the systems.

VI. System Preparation

Figure 3:
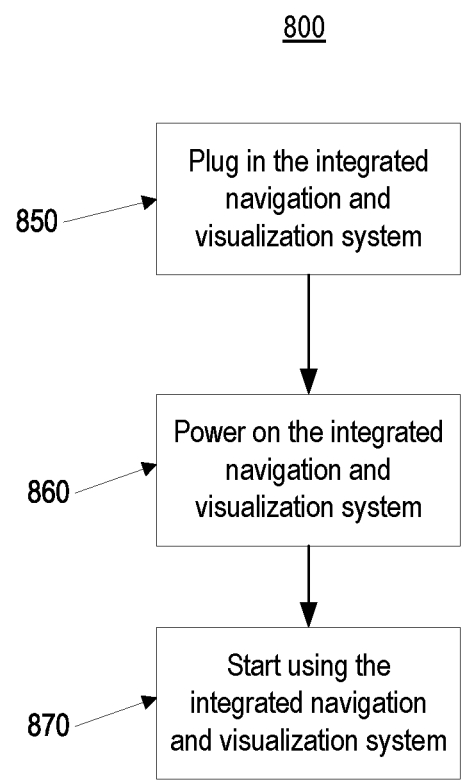
FIG. 3 is a flow diagram showing an example process for starting up the integrated navigation and visualization system, according to an example embodiment of the present disclosure.

FIG. 3 is a flow diagram showing an example process 300 for starting up the integrated navigation and visualization system, according to an example embodiment of the present disclosure. For example, the user of the integrated navigation and visualization system may be trained to follow system preparation steps as shown in process 300. At step 850, the user may plug the integrated navigation and visualization system into the hospital main power (e.g., by plugging into a wall socket). At step 860, the user may power the system on (e.g., by turning the "on" switch). At step 870 the user may begin using the system. Workflow steps after turning on the system are further described below, in relation to FIG. 4.

The relative ease of starting up the integrated navigation and visualization system, as illustrated in FIG. 3, confers a major advantage of the integrated surgical navigation and visualization system over conventional multi-component systems for navigation and visualization, as the integrated surgical navigation and visualization system eliminates or obviates the need to perform various setup steps or startup processes. For example, as shown in FIG. 3, a single power plug may be required to be connected to hospital mains, whereas conventional multi-component systems may typically require at least two such connections. Furthermore, physical connections need not be made by the user between the navigation system and the visualization system. In contrast, conventional, multi-component systems may typically require some form of connectivity between the separate navigation system and visualization system. Furthermore, workflow synchronization need not be made between the navigation system and the visualization system. In contrast, conventional, multi-component systems may require some form of such workflow synchronization.

VII. System Workflow

FIG. 4 is a flow diagram showing an example workflow performed for the integrated surgical navigation and visualization system, according to an example embodiment of the present disclosure. A software application on the integrated surgical navigation and visualization system may perform software portions of the pipeline and may provide a workflow for the user to follow. Various portions of the workflow may be implemented in a workflow command and control module while other portions may be performed outside of the software and outside of the system. Such portions may be presented in order to provide a full picture of system usage.

For clarity, workflow command and control module is not shown in the data acquisition, processing and display pipeline 400. The implemented workflow is described herein. It is understood that while this workflow is described in a near-linear fashion, some processes can happen concurrently and/or in a different order than is presented here.

The workflow may begin with a set up of the operating room ("operating room setup") 900, where equipment, tools and accessories may be brought into the operating room. Such equipment, tools, and accessories may include, but are not limited to, the integrated surgical navigation and visualization system, patient clamp(s), navigation tools, surgical instruments, and anesthesia equipment. A group of workflow steps considered as the patient setup workflow steps 902 may be undertaken by operating room staff. These steps may begin with a scrub in 910, where staff who enter the sterile field perform their pre-cleaning and entry into sterile clothing. Additionally some preliminary patient scrub may be performed at this time.

At step 920, the patient may be brought into operating room awake. Afterwards, step 930 may include patient preparation 930, which may involve include hair removal near the surgical site and further sterilization of the nearby area. At step 940, the patient may be moved into a surgical position and at step 950, the anesthesiologist may anesthetize the patient.

Portions of the navigation setup associated with the patient may be performed in step 960. In some aspects, the relevant anatomy of the patient may be fixed rigidly relative to the navigation reference target. In neurosurgery, for example, the patient's skull may be fixed rigidly into a Mayfield clamp and the navigation reference target fixed rigidly to the clamp. Accessories, such as a navigated probe, may be made available at this time, for example, by removing them from their sterilization kit and placing them on a sterile table to be available for the surgeon.

The workflow may progress to a set of steps referred to herein as planning and operating room setup 962. Of the steps associated with planning and operating room setup 962, a steps 964 may typically occur in the non-sterile realm of the operating room, e.g., with equipment that is not required to be sterilized.

The user may proceed to use the software application on the integrated surgical navigation and visualization system to import patient information and patient image data at step 970 from patient data central storage. In some aspects, the patient data central storage may comprise one or more of a picture archiving and communication system (PACS), a hospital information system (HIS), or a radiology information system (RIS), collectively referred to as PACS/HIS/RIS 980. The patient information and patient image data may be provided over a communications interface such as hospital ethernet as formatted patient data 990. The patient information and/or patient image data may be formatted using one or more options (e.g., Digital Imaging Communication in Medicine (DICOM), Health Level (HL7), etc.).

At step 1000, the surgeon profile may be imported. Alternatively, a surgeon profile may be created, e.g., if none exists. At decision step 1010, if a navigation plan exists, then at step 1020 the user may load existing patient plan (segmented anatomy and trajectory information) from local storage 1030. However, if no navigation plan exists, the user may determine whether onsite planning is required at decision step 1040. If a navigation plan does not exist and/or if no onsite planning is otherwise required, then a reference image may be loaded at step 1050. If navigation planning is required or desired, then at step 1060 navigation planning may be performed. Additional steps for navigation planning may include, for example, image modality co-registration or fusion (e.g., for registering MRI to CT), region of interest (ROI) specification, segmentation of one or more regions, craniotomy (in the case of cranial neurosurgery) or other approach specification, and trajectory planning. At step 1070 the navigation planning may be verified, e.g., by the lead surgeon.

At step 1080, the operating room layout may be determined. The operating room layout may involve a positioning and/or an orientation of the integrated surgical and navigation visualization system, and how various pieces of operating room equipment are to be posed at various phases during the procedure.

At step 1090, the integrated surgical navigation and visualization system may be brought near an operating room table where the patient resides. The digital surgical microscope head may be kept away from sterile field for now. The localizer may be posed such that it can "see" (e.g., receive within its field of view), the relevant navigated tools needed during the current workflow steps. For example, during registration, the localizer may need to see the navigated hand probe and the navigated patient reference target.

At step 1100, the user may verify that the patient is ready for registration. At step 1110, the user may verify that the localizer is tracking the tools needed for registration. In some embodiments, these tools may include the navigated hand probe and the tracking may involve locating the navigated patient reference target. In other embodiments, the tracking may involve locating the navigated target(s) on the digital surgical microscope and the navigated patient reference target.

At step 1120, a patient registration may be performed. Various forms of registration may be available in the surgical navigation visualization system. A chosen registration may be a function of several variables, including but not limited to a type of procedure, patient position, and/or a patient condition. Forms of patient registration available may include, for example, fiducial matching, landmark matching, and trace.

In fiducial matching, fiducials may be added to the patient (e.g. by affixing) before the volume scan (e.g., via CT or MRI) is performed. The fiducials may be kept on the patient. The locations of the live physical fiducials may then be matched with those in the volume scan. The specification of the locations of the fiducials on the live patient may be performed using the tip of the navigated probe in some embodiments, and the focal point of the digital surgical microscope in other embodiments.

In landmark matching, physical landmarks on the live patient (e.g., the corners of the eyes) can be matched to corresponding landmarks in the volume scan data. Similar to fiducial location, the specification of the locations of the landmarks on the live patient may be performed using the tip of the navigated probe in some embodiments, and the focal point of the digital surgical microscope in other embodiments.

In trace, the user may be instructed by the software to use the navigated probe to trace over a uniquely shaped portion of the user anatomy (e.g., the saddle of the bridge of the nose including some of the area under the eyes). Also or alternatively, the focal point of the digital surgical microscope may be used in conjunction with robot moves about the region, with an autofocus mechanism providing a means of staying on the surface of the patient's anatomy.

Other forms of patient registration may include touchless registration using a laser, and touchless registration using photogrammetry/stereogrammetry.

At step 1130, the surgeon may review patient data and may verify the registration. If the registration is not accurate enough (e.g., does not satisfy a similarity threshold), decision step 1140 provides a logic for returning to step 1120 to repeat the registration step(s). If or after the registration is sufficiently accurate (e.g., satisfies a similarity threshold), workflow proceeds to steps 1142, which occur in most instances in the sterile realm of the operating room.

To prepare the patient and the digital surgical microscope for use in the sterile field, step 1150 includes covering the patient and the digital surgical microscope in one or more sterile drapes. Appropriate openings may be aligned as needed for the digital surgical microscope. For example a lens window may be aligned to the optics main entrance to the digital surgical microscope. The area of the patient where surgical entry is to occur may be exposed through the patient drape. The patient's skin may be sterilized with an antiseptic solution.

The earlier patient registration previously described in step 1120 may have occurred in a non-sterile field with an undraped patient and clamp as well as possibly a non-sterile navigated probe. Since the clamp was undraped and non-sterile, the patient reference navigated target may considered non-sterile. Thus, at step 1160, this target and/or the navigated probe (e.g., if used) may be replaced with sterile equivalents.

Referring to the workflow of FIG. 4, in relation to steps after 1160, the main portion of the surgery may begin. At step 1170, using the planning, incision points and/or paths may be marked or otherwise indicated on the patient. An advantage of the integrated surgical navigation and visualization system is that these incision points and/or paths can be drawn virtually as overlays over the live view as an alternative to physically marking the patient. This is quite useful since such points and/or paths may persist throughout the approach whereas physical marks are immediately removed since they are on the outermost layer of the skin which is the first to be peeled back or otherwise moved out of position (and out of visibility) during an approach.

The opening and approach may commence at step 1180 with patient incision. Some of the steps in this workflow may be specific to cranial neurosurgery but may apply to many common surgeries. At step 1180, the craniotomy begins. Another advantage of the integrated surgical navigation and visualization system may include the ability to plan the craniotomy shape in advance and draw it virtually as an overlay over the live image such that the surgeon merely needs to "cut by numbers" and follow the path with the cutting tool as drawn onscreen. This overlay persists optionally under control of the user during the whole time of the approach.

At step 1190 (e.g., as part of cranial neurosurgery) the dura may be opened. At step 1200, the digital surgical microscope head may be moved to where surgical site on patient resides. In some aspects, this step can occur earlier in the workflow shown in FIG. 4, e.g., to provide the virtual overlays for the skin incision and craniotomy steps.

At step 1210, the bulk of the surgery may be performed. More advantages of the integrated surgical system become apparent. For example, the planned trajectory may be drawn on the multiplanar reconstruction views responsive to user request. The robotic arm can be commanded under the user request to move the optical axis of the digital surgical microscope to align with the pre-planned trajectory. Also or alternatively, such alignment may be used to align the optical axis of the digital surgical microscope quasi-continuously in quasi-real-time to some vector such as the axis of a NICO port of the axis of a spinal dilator tool. Thus, the surgeon may be freed from having to manually position the microscope to keep a useful view down such axes which can change poses throughout the procedure.

Also or alternatively, at step 1210, navigated overlays may be used to allow the surgeons to "know where they are" within the patient anatomy. Furthermore, the navigated overlays may be used to allow the surgeons to have "X-ray vision" by drawing from the patient volume data portions of the patient anatomy, which might remain beneath physical structures on the patient which have not yet been removed.

When segmentation is used for example to specify the 3D shape and pose of a tumor, such a 3D shape may be drawn under user control in the correct perspective, pose, and scale to within some accuracy, and may be blended with the live image stream. This specification may allow the surgeon to identify which parts of not-yet-resected tissue might be "tumor" or "not tumor."

After the main part of the surgery (for example a tumor resection or aneurysm clamp) is complete, the dura maybe closed and the scalp may be sutured in step 1220. The digital surgical microscope head and cart may be moved away at step 1230. The surgery may be complete at step 1240.

At step 1250, images and/or video recorded during surgery may be stored (e.g., locally, at picture archiving and communication system (PACS) 1260, at a local storage for images and/or video recorded during surgery 1270).

VII. Camera Calibration

In order to determine position and orientation information (also known as "pose" information) of a target in a navigation camera's field of view, the navigation camera may need to be calibrated. To provide accurate rendering of an object over the live field of view, the digital surgical microscope camera(s) may be calibrated.

For a monoscopic camera, the target's geometric information may also be known; a stereoscopic camera can perform absolute measurements without further input. The calibration process for monoscopic and stereoscopic cameras may, at their core, be at least nearly identical, with the stereoscopic camera requiring an additional few extra steps.

At least one high-level procedure for calibration may involve: acquiring images; solving for camera parameters; and, optionally, solving for a 3D model of the object(s) in the scene.

By adding a special calibration target in the image for each the calibration of the navigation camera and of the digital surgical microscope camera(s), the scale of the scene may be determined and two camera spaces may be tied together in a way that increases accuracy.

a. Acquire Images

In one embodiment, calibration may begin with taking a multitude (i.e., N) of snapshots (for example N=50), each with a slightly different pose of some object in the scene.

The pose variation may be achieved by controlling the robot to move the digital surgical microscope head about the object to N different poses and taking a snapshot at each pose.

The snapshots (e.g., images) may be each labelled with a timestamp having a resolution fine enough to make unique the filename of each snapshot. Such identifying information can optionally be embedded in the metadata of each image.

The requirements for the object in the scene which is imaged as described above, may vary with the type of camera calibration approach used.

b. Solve for Camera Parameters

Solving for camera parameters may involve one or more approaches, such as: photogrammetry; and the traditional calibration object method.

In at least one embodiment, photogrammetry may be used to solve for camera parameters. For photogrammetry, the object can be any object that retains its shape (what we will call being "rigid") over the course of the image acquisition, and has a minimal number of algorithm-friendly "features" dispersed over the surface of the object that the algorithm can detect in a minimal number of images. However, scale of the scene cannot necessarily be determined from a random object. A scale may need to be set either manually or in an automated way by inserting a scale object in the scene.

The snapshot poses can be overlapping such that a minimal number of features can be found in more than one image, and each image can have a minimal number of such features (but not necessarily the same features across all images.) Features may be detected in each image using any of several feature detection models, such as SIFT (scale invariant feature transform). The features detected as such can each be characterized using a feature "descriptor", which allows that same feature to be detected in multiple images and the algorithm to know that it is the same feature.

The pixel position of each such feature in the associate image can be recorded along with the feature descriptor. This pixel position may be used in camera calibration to assist in the determination of how features in the scene get projected via the camera structure to the sensor plane which converts the viewed scene into the images thus acquired.

With the assumption of the object being "rigid" over the image acquisition time, the algorithm is thus supplied with views from multiple poses of a given set of non-moving features. This may be repeated for different sets of features (typically a continually varying such set) over the set of acquired images. This information may be used to solve for the parameters in a camera model. The above described steps for acquiring images and solving for camera parameters may be referred to herein as "camera calibration" for simplicity.

Figure 5A:
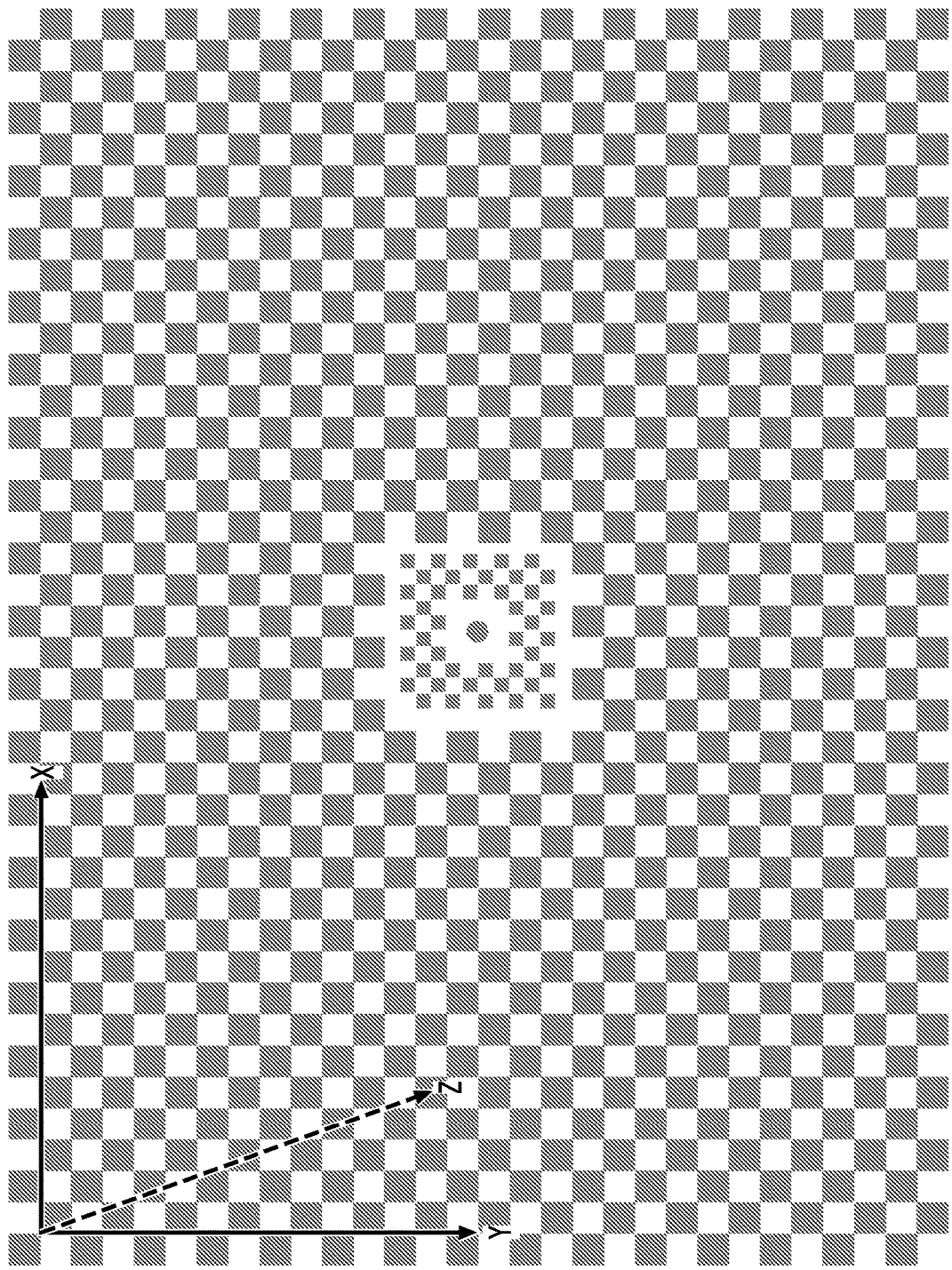
FIG. 5A is a diagram illustrating an example calibration reference frame setting the origin and axes, according to an example embodiment of the present disclosure.

A 3D model of the scene thus captured can also be calculated. Due to the ability to use any object (versus a calibration object of known structure), the scale of the world scene is not known at this point in the camera calibration using photogrammetry. Scale is set by including an object of known dimensions in at least some of the images captured during acquisition. The object can then be found manually or automatically in the 3D model and the corresponding model points The origin and axes of the calibration reference frame are set in a similar manner, for example, by including a planar object with linear orthogonal features that are used to define the X and Y axes; the Z axis is defined implicitly using the vector cross product of the X and Y axes, in a right-handed coordinate system by convention as shown in the image. An example calibration reference frame setting the origin and axes is provided in FIG. 5A.

Traditional Calibration Object Method

When a calibration object of known structure is used and the features constructing that structure can be detected by the processing algorithm, no overlapping of images may be necessary among the acquired images, and the traditional calibration object method such as OpenCV::calibrateCamera can be used. The remainder of the processing may be quite similar to that of photogrammetry.

Figure 5B:
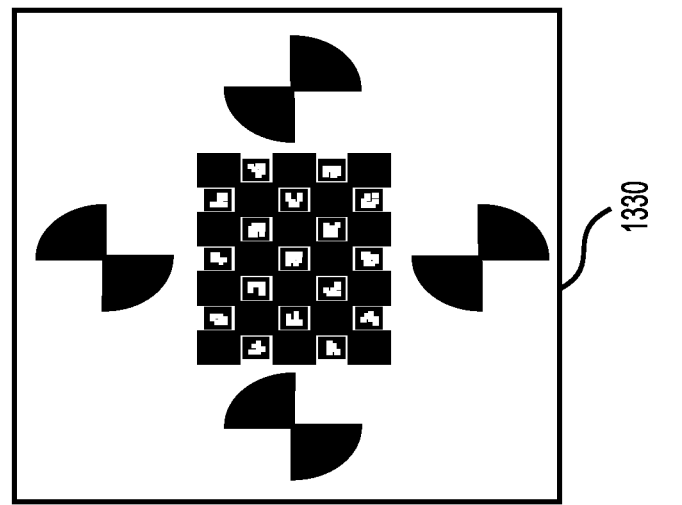
FIG. 5B is a diagram illustrating a calibration object applicable to the integrated surgical navigation and visualization system, according to an example embodiment of the present disclosure.
Figure 5B:
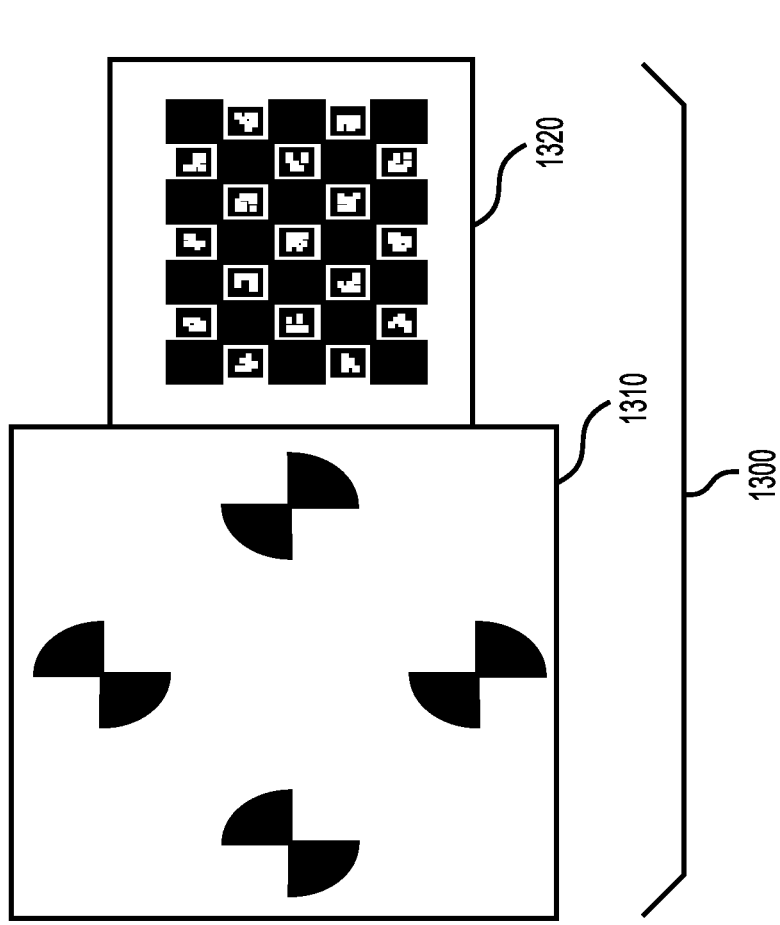

FIG. 5B is a diagram illustrating a calibration object applicable to the integrated surgical navigation and visualization system, according to an example embodiment of the present disclosure.

Using standard camera calibration methods, such as OpenCV cv::calibrateCamera, the following intrinsic camera parameters may be determined for each of the two camera eyes of the stereoscopic digital surgical microscope: principal point (cx, cy); and focal distance (fx, fy).

The cv::calibrateCamera process may be realized by taking snapshot images of a calibration target at multiple poses of the respective camera eye relative to the target which target contains computer-vision-detectable sub-objects. The sub-objects in some implementations may be unique relative to each other and thus the location of each individual sub-object relative to the whole calibration target may be known.

In some aspects, cv::calibrateCamera may use a simultaneous solving process to determine the intrinsic camera parameters as well as the extrinsic camera parameter at each pose of the camera. Said extrinsic parameters are composed of a three-dimensional translation and a three-dimensional rotation of the respective camera eye relative to a predetermined reference frame of the calibration target:

Tx, Ty, Tz (e.g., translations from the origin along each axis of the calibration reference frame); and Rx, Ry, Rz (e.g., rotations about each axis of the calibration reference frame)

The extrinsic parameters may be unique to each unique pose of the respective camera eye relative to the calibration target reference frame for each such of the multiple poses used to generate snapshot images for use in the calibration process. In contrast, the intrinsic parameters may be constrained to remain constant over all such images.

The concepts may be extensible to N-camera digital surgical microscope where N is 2 or greater.

A navigated calibration object 1300 may be created comprising a navigation target 1310 trackable by the navigation camera 200 as well as computer-vision-detectable sub-objects 1320 arranged in the reference frame of the navigation target in known positions and rotations (i.e. in known poses.)

A navigation target 210 trackable by the navigation camera may be affixed rigidly to some physical frame common to the cameras' respective optical systems. In some embodiments, one or more additional such targets may be placed variously about the frame such that the localizer (i.e. the navigation camera) can "see" at least one target at any time over a large range of poses of the digital surgical microscope head relative to the localizer.

The navigated calibration object may be placed within view of the stereoscopic digital surgical microscope.

The stereoscopic digital surgical microscope can be set to a given zoom and focus distance. Furthermore, the stereoscopic digital surgical microscope can be made to move through N poses relative to the navigated calibration object, keeping the navigated calibration object in the field of view, and recording an image for each camera eye at each pose.

Disparity in a stereoscopic digital surgical microscope may be defined for a given onscreen point or region as the number of pixels of separation between the left and right camera eyes for a given point, region or feature of the scene at the onscreen point. For example, the center of the screen may be chosen as the point at which disparity is measured, and the onscreen center of the left camera eye may be viewing a scene feature such as the bottom left corner of an irregularly shaped triangle.

It may be determined (e.g., via user input or automatically via computer vision pattern matching such as OpenCV cv::matchTemplate( )) that the same feature appears 5 pixels to the right of the onscreen center of the right camera eye. The disparity in this case may be "+5 pixels." The determination of which direction about the central axis of the screen is positive versus negative sign may be arbitrary and pre-determined.

The stereoscopic digital surgical microscope can be calibrated such that, across the whole operating range of zoom and working distance, the disparity at the center of the screen for each camera eye is at or near zero pixels when the system is in "generally good focus." In some embodiments, other points on the screen may be used and/or other values of disparity.

During image acquisition at the N poses used in calibration, the view of the navigated calibration object may be optionally kept in generally good focus via robotic movement until an "in-focus" metric is optimized such as minimized disparity. The robotic movement can be controlled via a feedback loop. The feedback loop may continually monitor the measured parameter disparity and may use a measurement to drive the robot arm such that the stereoscopic digital surgical microscope moves closer to or farther from the navigated calibration object along an estimated optical axis of the microscope, thereby adjusting the measured disparity.

The navigation camera 200 (also referred to as "localizer") may continually image the navigated targets (also referred to as "tools") in its view. The navigation processor 680 may subsequently calculate the pose in some reference frame of each such tool, and may report said tool pose info to the embedded processing unit. The reference frame used may be referred to as the "localizer reference frame" and may be typically posed somewhere convenient and sensible on the localizer camera such as at the midpoint of the line joining the camera's two eyes when a stereoscopic localizer camera is used. For example, one axis of the reference frame may be aligned with said line, another axis may point orthogonally outward from the front face of the localizer camera, and a third axis may be oriented to satisfy a right-handed Cartesian coordinate system.

At each pose of the robot (and hence of the stereoscopic digital surgical microscope) where a calibration snapshot image is recorded, the tool pose info for each the navigated calibration object and the navigated target(s) on the digital surgical microscope can also recorded and indexed to the calibration snapshot image for later use.

These poses may be represented as homogeneous transformation matrices, and may be able to transform one reference frame into another. The naming of such matrices may be chosen to allow "chaining" of multiple matrices, where the final result of the multiplication of a succession of matrices may result in the transformation of the rightmost-listed reference frame into the leftmost-listed reference frame, and the inner names may need to match. This naming and representation allows for rapid on-sight verification, e.g., to ensure that the math is correct.

The transformation from space "B" to space "A" can be written "backwards" as A_T_B and pronounced, "the transformation from space B to space A is A_T_B: B to A."

This naming may allow easy "chaining" of transformations by lining up the "inner" pairs of space names. The final transformation may be the "outer" pair of space names.

Example

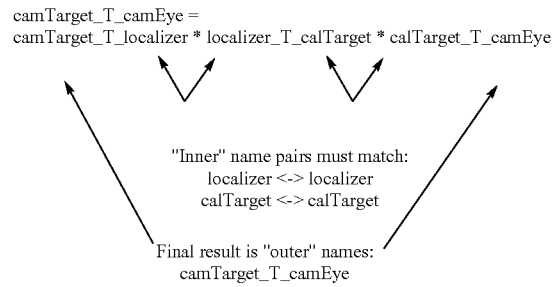

The inverse of a matrix A_T_B can be written as B_T_A. For example:

$$calPattern\_T\_calRefFrame = calRefFrame\_T\_calPattern.inverse(\ ) \quad (1.1)$$

In camera calibration, the camera may be modeled as a pinhole with a reference frame, the origin of which may be the pinhole. The camera can be placed such that the scene appears on one side of the pinhole and the sensor appears on the other side of the pinhole. For mathematical simplification, the sensor may be moved conceptually to the same side as the scene. The pinhole can be variously referred to as the "eye point", the "camera eye", or the "center of projection."

The pose of the navigated calibration object in the localizer reference frame can be denoted as: localizer_T_calTarget (2.1)

When multiple targets are used on the digital surgical microscope (e.g., to improve visibility over the range of possible camera poses), the poses of the multiple navigated targets on the digital surgical microscope can be reported in the same way as when a single navigated target is used. For example, a single representative pose in the localizer reference frame can be reported as: localizer_T_camTarget (2.2)

This reporting may not necessarily just be a notation convenience. When multiple navigated targets are used on the digital surgical microscope, one target can be chosen as the primary target and the locations of the others can be determined relative to that primary target. Thus, the navigation processor may calculate and report a single such tool pose in the tool pose information stream.

Each snapshot used in the camera calibration process may provide the pose of the camera eye relative to some pre-determined reference frame of the calibration object, which typically is part of some calibration pattern used in the calibration object. Thus, the pose (i.e. the extrinsic parameters) of the camera eye can be determined relative to that calibration pattern, and may be denoted as:

calPattern_T_camEye (2.3), where "camEye" denotes the location and orientation (i.e. the "pose") of the reference frame of the center of projection and coordinate system of an idealized pinhole camera model of the entire optical system for a given single camera of the dual-camera stereoscopic digital surgical microscope.

For simplicity, the calibration object reference frame may be taken to be coincident with the reference frame of the navigated target mounted to the calibration object. The pose of the calibration pattern relative to the (reference frame of the) navigated target mounted to the calibration object can thus be denoted as:

$$\text{calTarget\_T\_calPattern} \quad (2.4)$$

In some embodiments, this is made to identity by making the reference frame of the calibration pattern be coincident with the reference frame of the navigation target mounted on the calibration object as in 1330.

For a given single calibration image with the associated respective camera eye poses relative to the calibration pattern, the pose of a given camera eye relative to the single representative navigated target on the digital surgical microscope may be calculated as previously described (e.g., inverse notation, matrix "chaining" method, etc.):

$$\text{camTarget\_T\_camEye=camTarget\_T\_localizer*localizer\_T\_calTarget*calTarget\_T\_calPattern*calPattern\_T\_camEye} \quad \text{Eq 3:}$$

Since there may be N such calibration images and associated respective camera eye poses, there can be N occurrences of camTarget_T_camEye calculated. To reduce the effects of measurement noise and systemic error, the N occurrences of camTarget_T_camEye can be averaged to find a final camTarget_T_camEye for each camera eye.

In some embodiments calTarget_T_calPattern can be made by design to be the identity matrix, simplifying the equation.

The Tx, Ty, Tz translations are each averaged in a linear manner.

Averaging rotations Rx, Ry, Rz can be performed, for example, by converting the angular set to quaternions, checking that none are polar opposites and solving using, for example, a Markely-type method.

After the above steps are complete, system calibration may be deemed as complete.

In a typically offline process, the patient can be scanned volumetrically resulting in a three-dimensional sampling of the relevant patient anatomy in some reference frame (e.g., a reference frame of the scanning device).

The navigated target mounted to the patient clamp may also referred to as the "patient reference target." The patient reference target plays a similar role during runtime use of the system as the navigated target mounted to the calibration object did during the calibration process.

A patient registration process can be performed, resulting in knowledge of the pose of the relevant patient anatomy relative to the patient reference target and denoted as:

$$\text{patientTarget\_T\_patientData} \quad (2.5)$$

Finding where the camera eyes are looking in the patient data

The combination of the information described above may be used to determine where each of the respective camera eyes of the stereoscopic digital surgical microscope are looking in the patient data during runtime use of the system. In modern computer graphics systems, the inverse of this construct can be calculated. Thus, the pose of the patient data in each of the respective camera eyes of the stereoscopic digital surgical microscope is determined as:

$$\text{camEye\_T\_patientData=camEye\_T\_camTarget*camTarget\_T\_localizer*localizer\_T\_patientTarget*patientTarget\_T\_patientData} \quad \text{Eq 4:}$$

The above described equation may be the "model-view" portion of setting up the computer graphics renderer; the equation describes how the model (e.g., the patient data) is to be viewed.

A projection matrix of the computer graphics system may be used to describe how points in the scene are projected onto the display screen. The camera calibration process may be similar to determining how points in the scene are projected onto the camera's image sensor. The camera intrinsics resulting from camera calibration may be used directly in creating the projection matrix.

In some computer graphics systems (e.g., OpenGL), the final projection process can also include a mapping to an interim space (e.g., the normalized device coordinate space). This can be achieved by taking the projection matrix just described and pre-multiplying by another matrix. The result can also be referred to as a projection matrix, and may offer the opportunity to directly manipulate the field of view as is described next. For simplicity, the result may be referred to as the combined projection matrix.

In association with the image sensor width and height ratio, the camera intrinsic parameters known as "focal length" may describe the angle of view of the camera and may be used directly in the projection matrix.

An optional explicit field of view calibration improves on this and may be used in some embodiments. The optional explicit field of view calibration may require an additional focus distance calibration as will be described herein.

A calibrated measurement tool such as a ruler with gradations may be placed in the scene such that its image may align with, and therefore measure, a relevant dimension of the screen (e.g., the horizontal width of the screen).

The camera may be set to some zoom and working distance setting. The ruler may be brought into focus by moving the camera head mechanically. The screen width (e.g., the horizontal field of view at the focal surface) may be read directly from the ruler.

The process may be repeated over multiple optical settings (e.g., six zooms and six working distances spanning each respective range for a total of thirty-six measurements). The results may fit to respective curves in a parameterization process as described herein, thus providing an accurate measure of the (in this example) horizontal field of view over the whole zoom and working distance range.

To assist in automating this process, a pattern may be used as the measurement tool. The pattern can be detected and measured by computer vision processes. For example, a flat plate can be adorned with a mostly symmetric checkerboard image. The dimensions of each feature of the checkerboard image may be known by design and/or measurement. Some asymmetry or other feature may be added to assist the computer vision processes as well as robot control such that the plate can be kept centered nominally in the camera view.

Multiple patterns of varying sizes may be optionally used to provide accurate calibration over a wide zoom range.

Traditional camera calibration can also provide a measure of the optical distortion of the system at the optical parameter settings at which the calibration process was performed. A set of distortion coefficients can be found and can be used in some embodiments to correct such optical distortion. In some embodiments, such distortion correction can be used to improve the field of view calibration method. Furthermore, in some embodiments, such distortion correction can be used to improve the accuracy of the overlay (e.g., how it matches the live view.)

In embodiments where an explicit field of view calibration process may be used to improve on the field of view determination for the projection matrix of the computer graphics renderer, the distance to the focal surface of each camera eye of the stereoscopic digital surgical microscope may be required to be calculated. The determination of this distance for each camera eye will be discussed herein, in relation to FIG. 7C.

Figure 6:
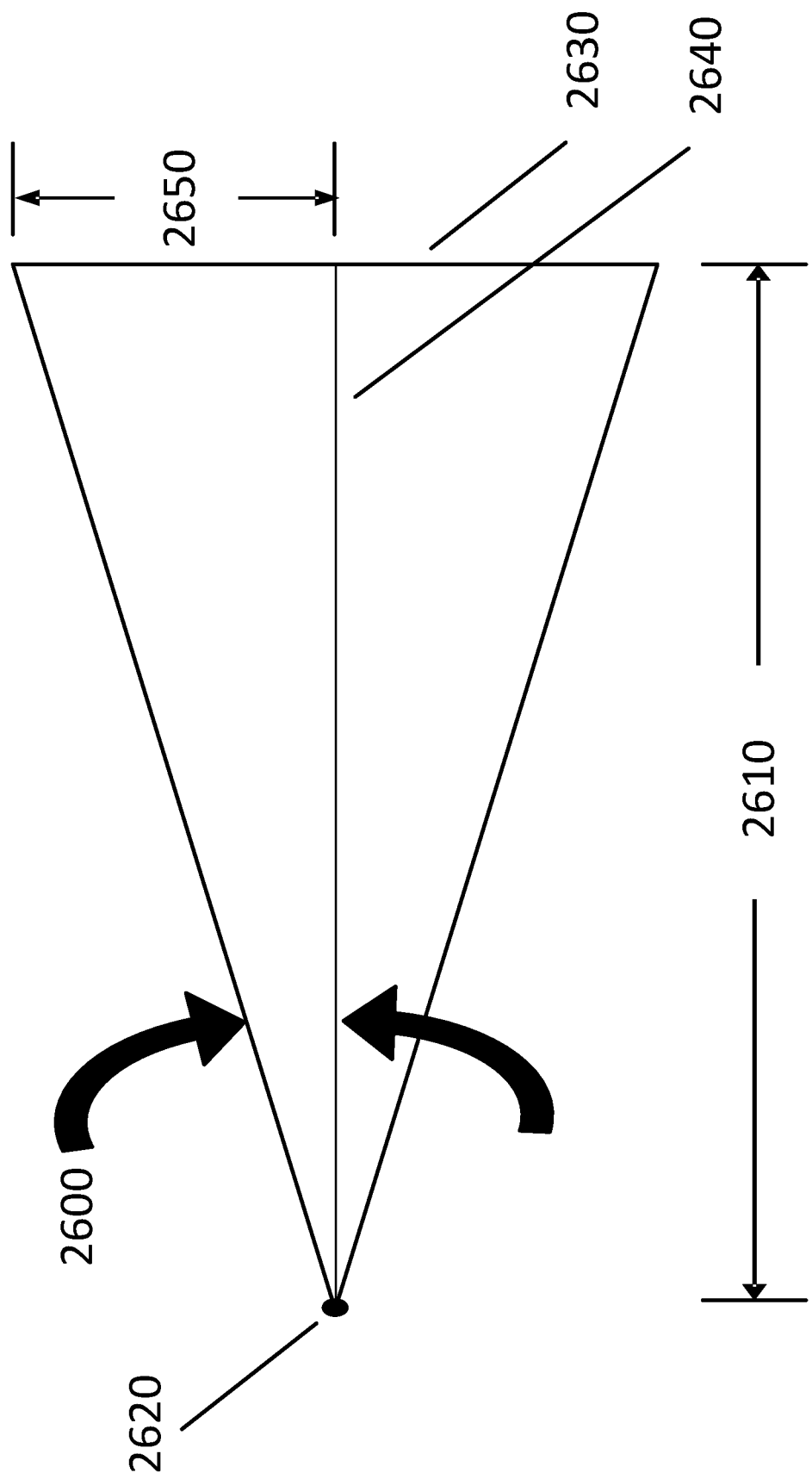
FIG. 6 is a diagram showing an angle of view applicable to the integrated surgical navigation and visualization system, according to an example embodiment of the present disclosure.

FIG. 6 is a diagram showing an angle of view applicable to the integrated surgical navigation and visualization system, according to an example embodiment of the present disclosure. With the focus distance, the angle of view can be calculated. This angle may be needed to calculate terms in the projection matrix and can be found by trigonometry, as shown in FIG. 6:

For example, the half angle 2600 can be found by measuring the focus distance 2610 from the camera center of projection (also referred to as the camera "eye point") 2620 to the focus surface 2630 along the optical axis 2640. The additional field of view calibration can provide a measure of the field of view (for example the horizontal width) at the focus surface. The half of such distance is shown as marker 2650. The tangent of half angle 2600 is distance 2650 divided by distance 2640. The inverse tangent function can then be used to calculate the "half field of view angle." The half field of view angle can be used to calculate directly certain matrix elements of the combined projection matrix as:

Matrix element (0,0)=1.0/tan(halfHorizontalFieldOfViewAngle), and

Matrix element (1,1)=1.0/tan(halfVerticalFieldOfViewAngle), where it should be noted that the horizontal and vertical field of view are related by the width and height ratio of the sensor (or equivalently of the images used in camera calibration.)

The previously described camEye_T_patientData in combination with the projection matrix utilizing camera intrinsics information determined earlier provide a faithful rendering of a duplicate representation from the (typically volumetric) patient data of any part of the relevant patient anatomy of the live patient that is within the field of view and depth of focus of the digital surgical microscope. Further, this rendering is effective in each respective eye of the digital surgical microscope, thereby enabling stereoscopic rendering of such a representation.

The rendering may be registered to the live patient view on the stereoscopic digital surgical microscope in the correct position, orientation and scale to within some tolerance of each. Further, the perspective of the render in three dimensions also matches the live view to within some tolerance.

These features along with appropriate user interface controls enable the user to "look inside" the patient even without making any incision. These features similarly allow the user to "look ahead" of where they currently are if for example they have made incisions and are performing a surgical approach to a pathology en route to providing therapy for said pathology.

Further, these features allow each of these capabilities to be viewed by the user in stereoscopic, which may greatly enhance spatial awareness and is more intuitive.

Further, these features allow the utilization of (typically volumetric) patient data on the same display as the live surgical site view, thereby reducing cognitive load of having to remember complex three-dimensional views when transitioning between the navigation device and the surgical visualization device. The presently described integrated surgical navigation and visualization system incorporates both devices, integrating them into a greater whole.

IX. Finding the Digital Surgical Microscope Camera Reference Frame

During camera calibration, the digital surgical microscope camera reference frame may be defined with its origin at the "pinhole" of the pinhole camera model. This location may also be referred to as the "center of projection" of the camera. Knowing the pose of the reference frame of the digital surgical microscope camera(s) optical center(s) relative to the reference frame of the navigation device may be significant in being able to solve for the pose of the digital surgical microscope relative to the patient data, which is the main objective of surgical navigation.

When such a pose is known to a good degree of accuracy and the camera optical parameters are modeled sufficiently well, the highest level of surgical navigation described herein can be provided. Systems and methods described herein disclose that highest level of surgical navigation.

One of the essential functions provided by the navigation is to answer the questions, "Where am I, where am I going, what is nearby?" This may be equivalent to determining the pose of the digital surgical microscope camera(s) relative to the patient data (while also knowing the camera intrinsic parameters.) This section focuses on determining the extrinsic relation between the camera and the patient data, that is, the pose between the two.

The mathematics required to calculate the pose between the digital surgical microscope (DSM) camera(s) and the patient data use 4×4 homogeneous transformation matrices to calculate the relative pose between a given pair reference frames and, for the overall system, through a chain of such reference frames. In this document, the terms "transformation", "transformation matrix", "4×4 homogeneous transformation matrix", "matrix", "pose" and "relative position and orientation" are used interchangeably.

The terminology used here for such 4×4 homogeneous transformation matrices is: A 4×4 homogeneous transformation matrix that takes points in reference frame A and transforms them to reference frame B is written as B_T_A and is read "backwards" such that it is pronounced "A to B."

For example the matrix dsmCam_T_patientData is read "backwards" as "patient data to DSM camera" (when the abbreviations are said in full) and thus a point in patient data space can be pre-multiplied by this matrix to give the location of the same point in DSM camera space:

P|DSM=dsmCam_T_patientData*P|PATIENT DATA

It should also be noted that a 4×4 homogeneous transformation matrix from reference frame A to reference frame B is the matrix inverse of the transformation from reference frame B to reference frame A, and vice versa. Thus:

dsmCam_T_patientData=patientData_T_dsmCam.inverse( ) and patientData_T_dsmCam=dsmCam_T_patientData.inverse( )

To transform from one reference frame to another it is possible to transform through intermediate reference frames, similar to there being multiple different routes between two physical locations. This is written for example as follows:

dsmCam_T_navCam=dsmCam_T_navTarget*navTarget_T_navCam which says, "The transformation from the navCamreference frame to the dsmCam reference frame (left-hand side of the equation) equals the transformation from the navCam reference frame to the navTarget reference frame premultiplied by the transformation from the navTargetreference frame to the dsmCamreference frame.

Note how the inner names (navTarget) match up on the right-hand side of the equation, and the outermost names (dsmCamand navCam) are the final result on the left hand side, in the order they appear on the right-hand side. That's key and that's why we write the transformation name "backwards."

Writing them that way makes it so much easier to write and read the equation and know that it's what we need. The chain can be extended indefinitely as long as the inner names match up, such as in:

F_T_A=F_T_E*E_T_D*D_T_C*C_T_B*B_T_A

To determine the relative pose between the digital surgical microscope camera(s) and the patient data, the on-head navigation camera method may involve:

(1) An (optionally offline) determination of the relative pose between the digital surgical microscope camera(s) and the navigation camera. This is referred to here as "camera registration." An example schematic model and calculation of the relative pose between the digital surgical microscope camera and the navigation camera is shown in FIG. 7A. While FIG. 7A shows the navigation camera on the DSM head, it should be appreciated that the navigation camera can be located anywhere for sensing the navigation target.

(2) A peri-operative determination of the relative pose between the patient data and the navigation target. This may be referred to herein as "patient registration" for simplicity.

(3) A runtime determination of the relative pose between a navigation target in the scene affixed rigidly to the patient (typically via bony structures directly or indirectly). An example schematic model and calculation of the relative pose between the navigation target in the scene on the patient is shown in FIG. 7B As shown in FIG. 7A, the calculation of the relative pose between the digital surgical microscope camera and the navigation camera may involve offline step 700A, indicated as Navigation camera <-> DSM camera transformation calculation (offline). Step 700A is the camera registration step and determines the relative pose between the digital surgical microscope camera(s) and the navigation camera. Step 700A of Navigation camera <-> DSM camera transformation calculation (offline) may be calculated as:

dsmCam_T_navCam=dsmCam_T_navTarget*navTarget_T_navCam, where dsmCam_T_navCam is the camera registration result describing the location of the reference frame of the digital surgical microscope camera(s) relative to the reference frame of the navigation camera; dsmCam_T_navTarget is the pose of the digital surgical microscope camera(s) relative to the navigation target and is determined during camera registration via camera calibration and/or photogrammetry; and navTarget_T_navCam is the pose of the navigation target as seen by the navigation camera and is solved per frame using an algorithm such as OpenCV::findChessboardCorners to find critical features of the navigation target in every frame (or a subset of frames, depending on available compute capability) in concert with OpenCV::solvePnP to take those image locations and along with the navigation camera calibration information determine the pose information of the navigation target.

As shown in FIG. 7B, the calculation of the relative pose between the navigation target in the scene on the patient may involve step 700B, indicated as "Patient data <-> DSM camera transformation calculation (runtime)." Step 700B refers to the calculation of the relative pose between the digital surgical microscope camera(s) and the patient data and may be a final single matrix result needed to render a representation of the patient data from the same orientation and position that the digital surgical microscope camera(s) are relative to the live patient. This enables augmented reality for surgery.

For the stereoscopic digital surgical microscope camera, a further minor transformation is found and used in the equation to account for camera eye separation. To render optionally other regions of the patient data (for example a slice deeper than we are currently looking), an additional simple transformation, such as a translation along the Z axis, is found and used in the equation.

Thus, step 700B, "Patient data <-> DSM camera transformation calculation (runtime)," may be performed via the following transformations:

dsmCam_T_patientData=dsmCam_T_navCam*navCam_T_navTarget*navTarget_T_patientData where dsmCam_T_patientDatais the final single matrix needed to render the patient data as just described; dsmCam_T_navCamis the "navigation camera to DSM camera" transformation and is found via the camera registration step described elsewhere in this document; navCam_T_navTargetis the pose of the navigation target as seen by the navigation camera as described elsewhere in this document; and navTarget_T_patientData is the transformation output describing the patient anatomy pose relative to the navigation target and is determined during the patient registration step described elsewhere in this document.

X. Accuracy Improvement a. Improving Accuracy by Reducing the Number of Devices in the System The navigation device may be integrated into the microscope head and thus can move rigidly with the head. Therefore no target may be needed to determine the movement of the head. This may reduce the number of devices in the navigation calculation path and thus improves accuracy by removing the inaccuracies introduced by those extra devices.

For example FIG. 1A, which shows an example surgical navigation system is based on three devices: an optical microscope with an infrared target ("antlers"), a remote localizer, and a patient reference frame (3 devices). In contrast, FIG. 1B, which shown an auto-navigating, integrated surgical navigation and visualization system comprises only two devices, a digital surgical microscope extended with navigation device, and a patient reference frame.

The math required to calculate the real-time pose of the digital surgical microscope camera(s) relative to the patient data shows why there is an accuracy improvement over the legacy solution application: There is one fewer term in the matrix multiplication. This means that the inaccuracy presented by the physical or virtual mechanism that that term describes, is removed. This decreases inaccuracy which is to say it increases accuracy or alternatively it improves accuracy.

b. Improving Accuracy by Greatly Reducing Time Between Calibration and Procedure Additionally the methods discussed in the present disclosure to calibrate the navigation camera, calibrate the digital surgical microscope camera(s), and calculate dsmCam_T_navCam can be performed at the time of the procedure, thereby eliminating inaccuracy that can creep in over the time elapsed preceding the procedure since the latest in-service calibration of a previous navigation device.

It should be noted however that the autonavigating, integrated surgical navigation and visualization system also allows such calibrations and calculation at in-service time if desired, instead of at the time of procedure. This saves some computation time during system setup at the time of the procedure.

c. Patient Registration

The registration step performs the calculation of patientRefFrm_T_patientData. The patient preop data is ingested and managed, the patient is prepared and the cal/navigation targets applied and scanned for surface data which is then aligned to the preop data.

d. Patient Scan Data i. Data Ingestion and Reconstruction

The data from the patient scan(s) are ingested into the system and in the case of 3D data placed in a data format convenient for 2D rendering as well as 3D (volumetric) rendering of the data.

ii. Surface Extraction from 3D Scan Data

A surface generally corresponding to the patient's skin is extracted from the 3D scan data. This surface is used to align to the similar surface extracted from the live patient data.

iii. Registration of Different Modalities

Different modalities such as CT and MRI are used for generating patient scan data. The registration described thus far aligns the data from the live patient scan and the data from one modality scan (typically CT.) To use an additional modality, that modality may need to also be registered to the live patient data. The registration step includes optionally use of a modality alignment module which aligns other modalities either directly to the live patient data or by registering to the already-aligned modality.

e. Patient Preparation

Patient positioning and clamping (which can be described as "fixing in place") proceeds as in current surgical navigation, typically after the patient is anesthetized. The patient is positioned appropriately for the procedure and the relevant anatomy fixed in place as much as possible. Then cal/navigation target(s) are affixed to the patient anatomy, typically to bony structures via a clamp attached to such structures (such as in the case of cranial surgery, to the clamp such as a Mayfield clamp that holds the patient's skull in place or as in the case of spine surgery to a patient's vertebra).

f. Peri-Operative Scan of Live Patient Data

After patient preparation, the digital surgical microscope camera(s) and navigation camera(s) are used to gather live patient data to enable patient registration and navigation.

g. Image Acquisition

The surface of the live patient is captured by moving the robot about the patient in many poses taking a snapshot at each pose while keeping the relevant part of the patient's anatomy in the field of view of the digital surgical microscope camera(s) for each snapshot. Keeping the patient's anatomy in the field of view is achieved via one of the following means, or a combination of some or all of them:

Manual "driving" the robot around the acquisition space by an operator around during image acquisition
  Using the software to instruct an operator to position and orient the microscope approximately in a known starting configuration relative to the patient (and appropriate for the patient position and procedure), and then controlling the robot via the software to move through pre-defined paths that are prescribed previously to capture the relevant anatomy of a very large percentage of patients over a spherical range
  Calculating a center point of a sphere and moving the microscope head about that sphere while keeping the focal point of the microscope coincident with the center of the sphere to within some tolerance (e.g. the tolerance of "lock-to-target")
  Using deep learning to extract patient anatomy features from images captured during acquisition and controlling the robot position and orientation to achieve sufficient coverage h. Calibration Target(s)

One or more calibration targets are mounted rigidly to the patient anatomy typically indirectly by mounting on a clamp for example. This calibration target may need to appear in at least a small number of the snapshots. Calibration targets are optionally used as navigation targets as well.

i. Photogrammetry

The images captured during patient registration image acquisition are sent to a photogrammetry module which performs the following, typically in this or a similar order, but some steps can be performed in a different order or in parallel with other steps:

Feature detection in each image using a feature description mechanism such as SIFT
  Correlation of features in images taken from "nearby" poses of the microscope head relative to the patient during image acquisition. This is a relatively sparse set of points compared to the number of pixels in an image.
    An alternative solution is to use the calibrated stereoscopic digital surgical microscope camera to extract a surface point per matched stereo pixel pair which is a much more dense dataset; the surface thus extracted per stereo snapshot taken at one pose is later stitched into a single larger whole with surfaces extracted from stereo snapshots taken at other poses.
  Solver-based solution to a camera extrinsic model for each image in the acquisition
  Optionally at this time: Solver-based solution to a single camera intrinsic model unified over all images
    The requirement for this to work well is to keep the digital surgical microscope camera(s) at constant zoom and working distance settings for the entirety of the image acquisition
    This step can be done optionally offline at some time (even days, weeks, months, years) before the procedure
  Scale and reference frame origin and orientation specification.
    Scale is found via readily detected features of known dimension such as two April tags placed a known distance away from each other
    Reference frame origin and orientation is found via the calibration target(s); a directional set of features along two orthogonal lines enable determination of two axes; the third axis is determined using the cross-product of the first two in a right-handed coordinate system (a left-handed coordinate system could be used instead)
    The patient reference frame origin and orientation is specified to be coincident with the reference frame just found
    If a navigation target is used that is different from the cal target, then enough features present in both may be required to be captured by either the digital surgical microscope camera(s) or the navigation camera (if we are re-calibrating the navigation camera at this time) such that the transformation between the two reference frames (cal and navigation target) can be calculated from the photogrammetry result.

Patient anatomy 3D model generation for the relatively sparse set of data represented by the feature extraction step. This is the surface extraction step for the live patient data When the stereoscopic pixel matching approach is used, model generation is significantly more accurate For the sparse model a subsequent step of "densifying" the model mesh is taken Data export to the main application including camera calibration information and patient anatomy 3D model This procedure proceeds in the same manner for each the left and right eyes of the stereoscopic digital surgical microscope with an additional eye separation value added in optionally This procedure is performed at a single zoom and working distance setting for example at a mid-range zoom setting. To function over the full range of zoom and working distance one of two methods are used:

The "brute force" method in which the zoom and working distance space is divided into a finite number of value combinations and a calibration performed at each possible value combination. The digital surgical microscope optics are then constrained to operate at those values only The "calculate and interpolate" method in which a single zoom is selected (for example a mid-range zoom value) and the calibration is repeated for a sampling of working distances over the working distance range. These are interpolated for intermediate working distances. The zoom value is incorporated by changing the field of view (essentially scaling the image) about the principal point of the camera. The amount of scale is determined by a separate calibration step which maps field of view to zoom motor counts.

Note that the navigation camera is also optionally imaging at this time such that it can be re-calibrated and/or the matrix dsmCam_T_navCam can be (re)calculated at this time very close to the procedure instead of days, weeks, months, years in the past, over which time the calibration and/or calculation may have degraded.

j. Using the Probe for Registration

As in current navigation, using a navigated probe to trace the surface of the patient is an optional means for extracting the patient surface for the purpose of registration. The tip of the probe relative to a probe-mounted navigation target is found during a calibration and verification step explained elsewhere, and the tip is tracked during a specific "trace" time and over a predetermined general region of interest on the patient as indicated to the user by the software.

The location of the probe as reported by the navigation module may be sampled at a rate sufficient to sample the surface path at a resolution high enough for surface feature extraction.

k. Aligning the Surfaces

In this step all or some of the captured portion of the surface of the live patient data is matched (also known as registered, or aligned) to all or some of the captured portion of the surface of the patient in preop data. This process results in the transformation patientRefFrm_T_patientData.

The two surfaces do not typically share a common coordinate system, nor is this feasible. Thus the transformation between the two coordinate systems may be determined.

Determining the transformation between the two coordinate systems is achieved by first optionally maneuvering the respective renderings of each dataset to be "close by each other" using a software visualization module. Any transformations used during this operation are recorded and become part of the final transformation.

The next step is to use one of several well-known alignment algorithms and/or techniques such as "iterative closest point" (ICP) which calculates a transformation between the two datasets that is best in some error minimization sense.

The transformation search algorithm is typically constrained to search for just translation and rotation and ignore scale, but due to differences in the calibration of the various devices involved in generating the two datasets, a search over a small range of scale is sometimes useful.

The output is a transformation matrix that describes the pose of the patient data relative to the cal target. If a navigation target is used that is different from the cal target, the pose between the two targets is included in calculating this output.

Thus when the rest of the system is enabled to determine the position and orientation of the digital surgical microscope camera(s) relative to the navigation target(s), and the camera intrinsic parameters are known for its current zoom and working distance, the system is enabled to render a view of the patient data over the live view of the patient. This is augmented reality for surgery.

l. Intraoperative Patient Data Updates

The same process of patient scan data registration to the live patient pose relative to the navigation target(s) is used to register new or updated data such as intraoperative MRI that might be generated during the procedure.

m. Navigation

Following the previously-described setup steps, the system is ready to provide surgical navigation to the user. The auto-navigating digital surgical microscope is placed to enable the navigation device to view the navigation target or targets XX mounted rigidly to the patient anatomy and to enable the digital surgical microscope camera(s) to view the areas of the patient anatomy relevant to the procedure. The navigation device data output is communicated to the main information processor module either in raw or processed form. If raw, then the processing is performed in the main information processor module. The data of interest is the value of the transformation navCam_T_navTarget with real-time or near real-time updates.

With this input as well as input from the digital surgical microscope camera(s) about the current zoom and working distance settings of said camera(s) in addition to the information described previously needed in the runtime math, the system is enabled to provide augmented reality for surgery.

n. Tool Usage

Navigated tools are an important part of the surgeon's toolbox. The navigated probe is the most commonly used such tool, and it consists typically of a dully-pointed metal rod to which is affixed a navigation target that can be detected by the navigation camera. It is used to make quick determinations of "what is where".

A calibration step is used to determine the probe tip location relative to the probe's navigation target; this step often performs the function of a verification step as well: after the first calibration, the system can simply recognize the tool's' target and verify that its tip is where the system thinks it should be to within a tolerance. The microscope is typically not used when the probe is being used, at least not immediately concurrently.

o. Positioning the Microscope for Tool Usage

The navigation camera may need to be able at all times to view the tool's navigation target(s). In the case where the surgeon does not need the microscope during probing, the user selects a preset position for the robotic arm which positions the microscope head out of the surgical field but close enough and in an orientation such that the navigation camera can still view the navigation target(s) on the tool as well as the one(s) affixed to the patient anatomy.

DSM robotic arm and head may move off to the side of the surgical field, tilted such that the navigation camera can still view all the necessary navigation target(s)

p. Calibrating the Tool

Calibrating the tool (sometimes referred to as verifying the tool) is the task of locating the tooltip relative to the tool's navigation target. This is achieved by providing a known location relative to a navigation target (or calibration target) and instructing the user to place the tooltip at that known location. The navigation device is constantly updating the pose of each target it sees in the scene and thus the translational component of the relative pose between the targets represents the tooltip offset from its navigation target.

To facilitate tooltip placement, the "known location" is made to be the bottom of a physical "divot" into which the tooltip can fit and be kept in nominally the same location while allowing the tool to be pivoted about its tip. The software instructs the user to indicate when the user has the tooltip in place in the divot, for example by requiring the manual click of a button.

An improvement to the manual-click method is to continually monitor in the software the translational offset magnitude between the tool navigation target and the target used for verification. If the magnitude stays unchanged within some tolerance for a given amount of time during the verification process, it can be presumed that the user is holding the tip in the "divot." However, the pose of a tool at rest outside the divot also has an unchanging translational magnitude relative to the calibration target.

As a further improvement to this process, the user is instructed to pivot the tool (and thus its navigation target) through some range of angles while keeping the tooltip placed in the "divot"; this causes change of angles in the relative pose while the magnitude of the translation remains relatively unchanged. This is a more robust way of determining whether the user is trying to verify the tool.

The procedure just described provides only translational offset of the tooltip from the tool navigation target. If tool orientation is important to know then a structure is provided which enforces tool navigation target orientation relative to the verification device navigation target.

This data can be stored in the tool definition file for later tool use without the tool calibration step, but as a tool can be deformed through use or handling, the verification step is generally required before the start of each use, for example at the start of a procedure. The user can optionally re-verify the tool at any time during the procedure.

q. Camera as Probe

As the steps in this document describe, the location and orientation of the digital surgical microscope camera(s) are known relative to the patient data. This means that the microscope can optionally be used to provide the same exact function as the navigation probe: to show in the navigation data "where am I looking?"

r. Augmented Reality for Surgery

With surgical navigation enabled as described, the system is ready to provide augmented reality for surgery at all of the levels of surgical navigation complexity mentioned previously. The mechanism for presenting such augmentation varies per procedure, surgeon preference, data availability and quality, and registration results.

s. Patient Data on System Displays

The patient data is displayed based on surgeon preference in various manners:
  Sharing the main visualization display with the live view of the surgical site
  On its own display near the surgeon's field of view
  Overlaid onto the live view of the surgical site, with options for the user to specify on/off and opacity The augmentation shown and the methods used in those data representations include but are not limited to:

i. Tip and Vector in Data

When a "Display tip and vector" option is selected in the software, the tip of each calibrated and verified tool (including the digital surgical microscope camera(s)) in view of the navigation camera is represented in the patient space by a uniquely colored annotation such as a dot. A glossary is optionally included to "connect the dots" as it were to the type of tool.

Alternatively a small text annotation is drawn near the dot and provides relevant information about the tool. The line along which lies the main linear feature of the tool (for example the optical axis of the digital surgical microscope camera(s)) is optionally drawn as well, with one end at the tip.

ii. Tool Orientation

For certain tools, the tool orientation is known relative to the navigation target. This enables drawing in the patient data an annotation incorporating the orientation as well as drawing the data oriented onscreen to how the tool is "seeing" the patient anatomy. For the digital surgical microscope, this orientation is made to correspond with the live view, reducing the complexity required for the surgeon to gain a mental picture answering the question, "where am I?" This reduces the surgeon's mental load during navigation use.

iii. Path Projection

The line along which lies the main linear feature of the tool is optionally extended ahead of the current tooltip to envision the path ahead for the tool. For example when inserting a pedicle screw during spine surgery, the current location of the screwtip is shown as well as its projected path as it is inserted further. This is critical information necessary to ensure that the screw is fully captured by the pedicle and does not break through into, for example the spinal cord column.

iv. Overlay

Since the optical parameters of the digital surgical microscope camera(s) are found during calibration and the pose relative to the patient data is known, an (optionally stereoscopic) 3D rendering of the patient data is rendered optionally over the live view.

Additionally, the parameters used to select the data to be rendered can be controlled to optimize the value to the surgeon. For example, a pre-planned approach corridor can be rendered in (optionally stereoscopic) 3D such that only the currently visible part of the approach plus the next few millimeters are shown. As another example, a 2D slice can be rendered at various levels along the optical axis relative to the focal point such that the surgeon can have a clear look at what is inside the patient.

This adds high value to the auto-navigating, integrated surgical navigation and visualization system described herein; it is essentially "x-ray" vision, enabling the surgeon to see into the patient even where no incision exists or where the surgeon has not yet exposed.

XI. Calibrating the Pose of a Visually Relevant Reference Frame Relative to the Representative Navigated Target on the Digital Surgical Microscope A separate calibration may be performed to determine the pose of a visually relevant reference frame relative to the representative navigated target on the digital surgical microscope. For example, this visually relevant reference frame may be the screen center for each eye of the stereoscopic digital surgical microscope.

The calibration may be performed by setting the microscope optical parameters such that the respective image captured by each camera eye is at or near optimal optical focus at said screen center. The optics may be designed and tuned such that at a given working distance setting the optics are focused on a point in space some distance away from the microscope.

Further, the optics may be designed and tuned such that the screen centers of the eyes of the stereoscopic digital surgical microscope are imaging the same point in space to within some tolerance when "in focus" at a given set of microscope optical parameters.

The point in the scene which is projected to the respective screen centers of each camera eye is referred to as the "focal point" of the microscope. Thus this separate calibration in part determines the location of the focal point of the camera relative to the representative navigated target on the digital surgical microscope.

There may be a focal surface to which can be assigned an origin and coordinate system to define a "focal reference frame." This may redefine a focal point as well as "up" and "right" vectors which may allow the orientation of the camera image(s) onscreen.

While physically the focal surface might not be purely planar (e.g., it may be slightly curved), the focal surface may be taken to be a two-dimensional plane for simplicity and ease of explanation. The origin of the focal reference frame may be taken in some embodiments to be the location in screen center of the calibrated camera and the pose of the focal reference frame is such that it is oriented orthogonally to the optical axis at a given optical setting of the microscope with its X axis pointing along the horizontal direction of the image sensor proceeding positively to the right and its Y axis pointing along the vertical direction of the image sensor proceeding positively downward. In practice, there might be additional "flips" of axis direction and offsets of the origin location to conform with preferred graphics systems, system requirements, user preference and the like.

Thus this separate calibration may determine the pose of the microscope's "focal reference frame" relative to the representative navigated target on the digital surgical microscope.

Since the focal point of the stereoscopic digital surgical microscope may be made to be the same for each of its component single cameras (i.e. each "eye"), and the onscreen axes may be coincident or nearly so, there may not be a need to perform a separate focal reference frame calibration per eye. In such embodiments, there may only be one calibration performed for the stereoscopic digital surgical microscope as a whole.

Figure 7C:
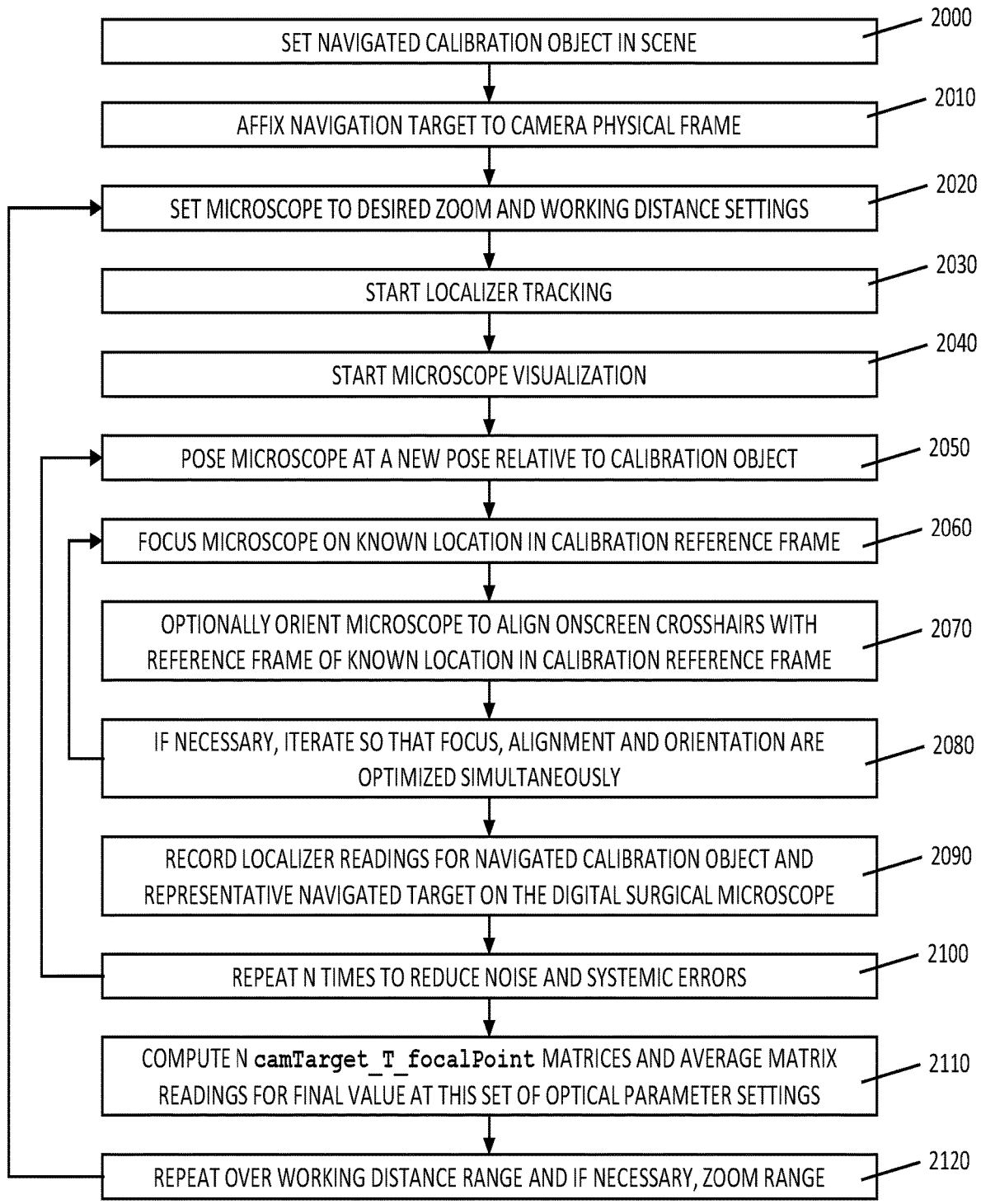
FIG. 7C is a flow diagram showing an example method for a focal reference frame calibration applicable to the integrated surgical navigation and visualization system, according to an example embodiment of the present disclosure.

FIG. 7C is a flow diagram showing an example method for a focal reference frame calibration applicable to the integrated surgical navigation and visualization system, according to an example embodiment of the present disclosure.

At step 2000, a navigated calibration object can be set into the scene. The calibration object may include one or more structures, (e.g., a crosshair) to aid alignment of the visually relevant reference frame of the microscope to the reference frame of the navigated calibration object (e.g., via a crosshair or other alignment aid on the navigated calibration object). Also or alternatively, the onscreen center and axes may be drawn onscreen by the graphics module to aid the operator in aligning the onscreen center to the calibration object alignment structure(s).

At step 2010, the navigation target may be affixed to the camera physical The microscope may be set to a desired zoom magnification and working distance settings at step 2020. The localizer tracking may be started at step 2030. The localizer may detect the presence of, and determine the pose in localizer space of, each trackable navigation target in its viewable scene. In some aspects, those targets may comprise the navigated calibration object and the representative navigated target on the digital surgical microscope.

At step 2040, microscope visualization can be started. At step 2050, the microscope can be posed relative to the navigated calibration target (or vice-versa.)

At 2060, the microscope can be focused on the calibration object alignment structure. For example, this structure may comprise a crosshair. To simplify and reduce error in the matrix calculations, the crosshair may be located at the origin of the calibration object's navigated target, and its X and Y axes may be coincident to those respectively of said target. The crosshair may be two-dimensional; the imagined Z axis may also taken to be coincident to the corresponding axis of the calibration object's navigated target.

At step 2070, the microscope may be optionally oriented to align the onscreen crosshairs with those of the calibration target. This step may be optional, for example, if the focal reference frame provides more information than is needed. In some embodiments, it may be sufficient to determine only the focal point location relative to the representative navigated target on the digital surgical microscope and to not also determine the orientation of the whole focal reference frame relative to said target.

Since changing the orientation of the microscope could change its optimal focus point, an iteration may be performed at step 2080 if appropriate to optimize the focus as well as the relative location (i.e. alignment) and orientation of the onscreen crosshairs to the calibration target crosshairs.

The localizer readings localizer_T_camTarget and localizer_T_calTarget may be recorded at step 2090. As noise reduction and systemic error reduction practices, it may be desirable to repeat, at step 2100, the overall measurement at a number (for example N=25) of different poses of the microscope relative to the navigated calibration target.

At step 2110, the function camTarget_T_focalRefFrame can be solved as:

camTarget_T_focalRefFrame=camTarget_T_localizer*localizer_T_calTarget*calTarget_T_focalRefFrame, where calTarget_T_focalRefFrame in some embodiments is identity by design to simplify and reduce errors in matrix multiplication. The simplified equation thus becomes:

camTarget_T_focalRefFrame=camTarget_T_localizer*localizer_T_focalRefFrame

These N solutions may be averaged using matrix averaging as described elsewhere in this document to determine a final value for camTarget_T_focalRefFrame.

For a more complete calibration, this process may be repeated at step 2120 at a number of zoom and working distance settings across the operating range of each such parameter. A curve may be fit for each relevant output parameter set as a function of input parameters. This process may be referred to as parameterization. The output parameter set may be the focal point pose relative to the representative navigated target on the digital surgical microscope.

The input parameters may include zoom and working distance settings from the camera control module.

Using the previously described camTarget_T_camEye and camTarget_T_focalRefFrame functions, the focal point reference frame pose relative to each respective camera eye of the stereoscopic digital surgical microscope can be determined by:

camEye_T_focalRefFrame=camEye_T_camTarget*camTarget_T_localizer*localizer_T_calTarget*calTarget_T_calCoordSys*calCoordSys_T_focalRefFrame, where calTarget_T_calCoordSys can allow for a transformation between the navigated target of the calibration object and an arbitrary coordinate system, and calCoordSys_T_focalRefFrame can allow for a transformation between that coordinate system and the focal reference frame. Both of these matrices may be identity matrices by design. The equation can thus be simplified as:

camEye_T_focalRefFrame=camEye_T_camTarget*camTarget_T_localizer*localizer_T_focalRefFrame.

XII. Robot Alignment of the Microscope Optical Axis to a Given Vector

In some embodiments, the digital surgical microscope head 110 can be mounted on a robotic arm 120. The robotic arm 120 may be controlled by a robot control module 820 in the microscope processing unit 420. The physical characteristics of the robot joints required to calculate robot end effector pose relative to the robot base (such as joint angles) may be known for all or most robot joints by design and/or calibration and/or real-time measurement during runtime. The further physical properties for calculating robot end effector pose relative to the robot base (such as nominal length and flexure under load and under pose change of the links connecting the joints) may be known by design and/or by calibration and/or by real-time measurement. Thus, the pose of the robot end effector (the most distal active joint or link of the robot itself) may be known relative to the robot base continually in real time and may be denoted as:

robotBase_T_robotEEff

The physical properties of all extensions such as coupler 140 and force-torque sensor 150 are also known by design and/or calibration, and/or measurement such that the pose of the distal end "control point" of e.g. 150 is known relative to the robot end effector and is denoted by:

EEff_T_controlPt

Further, the pose of the representative navigated target 210 on the digital surgical microscope head is known by design and/or measurement relative to a mounting datum 152 on the reference frame of which mounting datum is designed to mate coincidentally with the reference frame of the most distal reference frame such as 150 on the robot assembly before the camera head. Further improvements to the knowledge of said pose may be optionally made by measurement.

Thus the pose of the representative navigated target 210 on the digital surgical microscope relative to the control point 150 may be known and may be denoted by:

controlPt_T_camTarget

With these and prior transformations previous described, the pose of each respective camera eye relative to the robot base may be calculated as follows:

robotBase_T_camEye=robotBase_T_robotEEff*robotEEff_T_controlPoint*controlPt_T_camTarget*camTarget_T_camEye The robotEEff_T_camEye relationship may be sometimes referred to as the "hand-eye" pose relationship. Also or alternatively this hand-eye pose relationship can be discovered using known calibration techniques such as OpenCV's cv::calibrateHandEye method, and the math above may be reworked as:

robotBase_T_camEye=robotBase_T_robotEEff*robotEEff_T_camEye

The pose of the focal reference frame relative to the robot base is found using the previously described camEye_T_focalRefFrame function:

robotBase_T_focalRefFrame=robotBase_T_camEye*camEye_T_focalRefFrame     Eq 8:

The pose of the robot base in localizer space

The pose of the robot base in localizer space can be found using the following function:

localizer_T_robotBase=localizer_T_camTarget*camTarget_T_controlPoint*controlPoint_T_robotEEff*robotEEff_T_robotBase During planning phase 1060, useful features may be added to the patient data space to aid the surgeon in the execution of the surgical procedure. These features include but are not limited to surgical opening "cut by numbers" patterns, approach vectors (e.g., trajectory plans), and approach waypoints at which the digital surgical microscope can be posed repeatably to establish and evaluate progress.

A surgical opening in cranial surgery may be referred to as a craniotomy. During planning phase 1060 the user optionally can specify the outline of the desired opening. Critically, in traditional surgery such an approach is specified on the live user's skin using a surgical marking pen and is thus destroyed when the first layer of skin is removed (which is among the first steps in the procedure.)

The presently described integrated system enables the user to virtually draw such an opening plan in the patient data. This opening plan can then be displayed under user control for the entirety of the opening phase, e.g., beyond skin removal. Furthermore, the opening plan can address the three-dimensional nature of opening a patient. For example, instead of a simple line drawing, the plan can be multi-layer and/or three-dimensional to show the surgeon how to cut into the three-dimensional surface.

Figure 8:
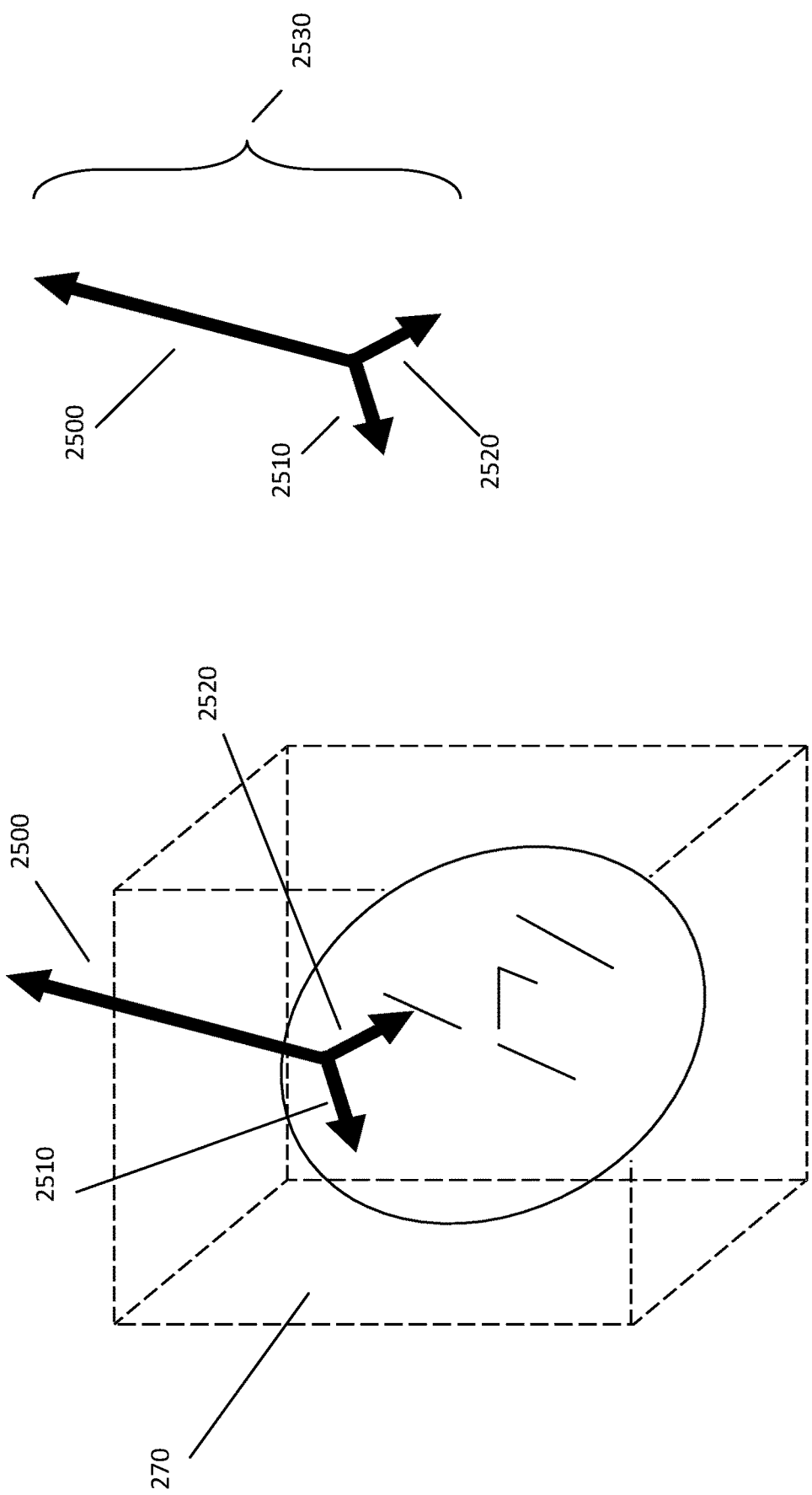
FIG. 8 is a diagram showing an example trajectory plan applicable to the integrated surgical navigation and visualization system, according to an example embodiment of the present disclosure.

FIG. 8 is a diagram showing an example trajectory plan applicable to the integrated surgical navigation and visualization system, according to an example embodiment of the present disclosure. A trajectory plan can be optionally added in a patient data space 270. The trajectory may comprise a path in patient data space along which the user desires the procedure to proceed. For example, a cranial neurosurgeon might plan a trajectory toward an aneurysm that avoids critical parts of the brain and favors more readily traversed regions. If the trajectory is complex, it may be split into separate smaller trajectories which are more readily represented and achieved (e.g., for piecewise linearly). Also or alternatively, waypoints may be added by the user in the patient data space showing desired camera poses relative to the patient. With the connection of robot space, camera space, and patient space allowed in systems and methods described herein, such waypoints can be visited at any time during the procedure. Furthermore, such opening, trajectory and waypoint planning can be updated and/or augmented at any time during the procedure.

An advantage of the presently described integrated system is that it provides the user the option to adjust visualization such that it is focused along the trajectory and optionally focused upon the "next step" in the trajectory. This adjusted visualization shows the surgeon the path where to proceed and indeed poses the microscope to be looking right at the place to do so. At least one example for providing this capability is described as follows.

The trajectory plan may be represented as a transformation in the patient data space: patientData_T_trajPlan (2.9)

The trajectory plan may primarily represent a vector 2500 along which the trajectory may proceed at the "next" step in the surgical procedure. It may be expedient (but optional) to represent the trajectory as a full reference frame such that an orientation about the primary vector 2500 is also specified. This orientation may be represented as two other axes 2510 and 2520. This enables the user to incorporate patient, surgeon and microscope positioning into the trajectory planning. Without such specification, the control algorithm merely needs to make a "best guess" at a sensible orientation for solved movements. For example, to ensure the correct orientation of the microscope head relative to the trajectory plan, a convention may be chosen such that a patient geometry keep-out is favored. Additional constraints may be added such as minimal movement, robot joint limits, and "outside looking in" orientation.

The preceding description may allow the robot control module 820 to pose the digital surgical microscope head such that it is looking along the trajectory planning path and further that it is focused on the "next step" of proceeding along that path. First the trajectory plan in the localizer space is determined as follows:

localizer_T_trajPlan=localizer_T_patientTarget*patientTarget_T_patientData*patientData_T_trajPlan, where each matrix on the right side are as described previously. Then the pose of the trajectory plan relative to the robot base can be found as:

robotBase_T_trajPlan=robotBase_T_localizer*localizer_T_trajPlan

Further, the trajectory plan can be replaced by other means of defining a pose in the patient data space, and the robot commanded to match or track said pose. Since various embodiments described herein provide connection of the camera space, the localizer space, and the robot space, such pose definition can be achievable by multiple means, including but not limited to: posing a navigated tool such as tool 252; the axis to which the alignment is performed can be defined arbitrarily within the navigated target space of such a tool; or the pose of a user's head, thereby enabling head tracking when a navigated target is connected directly or indirectly to the user's head for example to the 3D glasses 192. Such pose control of the camera can be relative to some starting position of the user's head (for example initialized upon some activation action such a pushbutton being pressed or a voice command saying, "Head tracking on".

Furthermore, the pose of a computer-vision trackable pattern mounted for example on a surgical tool may also be used to achieve pose definition. Similar to the head tracking just described, with some user activation function, the pose of the camera head is controlled by changing the pose of the trackable pattern, with the change in pose of the camera calculated from some starting pose measured at time of user activation. Depending on the activation function, this can provide hands-free control of microscope pose. Also, or alternatively, the pose of a navigation camera-trackable target mounted to a local part of the patient's anatomy such as a single vertebra during spine surgery. By tracking the movement of the vertebra the system provides a consistent view to the surgeon relative to the vertebra. This is especially useful when performing steps in the procedure that cause significant movement to the anatomy in question. For example as the vertebra moves, the camera pose may be updated to always be imaging the same place and in the same orientation where the surgeon is performing a laminectomy.

The pose of other navigated tools may also be used to achieve pose definition. For example, the camera may be posed continually to provide a clear view of the surgical site to the user showing for example the distal end of a primary tool and/or avoiding imaging the shafts of said tools which would normally block the visualization.

The focal reference frame may be matched to the trajectory plan reference frame. To drive the robot such that the optical axis of the digital surgical microscope is looking along the trajectory plan primary axis and optionally focused upon the trajectory plan origin, the pose of the trajectory plan in the space of the robot base can be set to be equal to the pose of the digital surgical microscope's focal reference space relative to the robot base as:

robotBase_T_focalRefFrame=robotBase_T_trajPlan which is found in an alternative manner using:

robotBase_T_trajPlan=robotBase_T_focalRefFrame=robotBaseT_robotEEff*robotEEff_T_controlPoint*controlPoint_T_camTarget*camTarget_T_camEye*camEye_T_focalRefFrame From the above equations, the robot pose robotBase_T_robotEEff may be required to match the trajectory plan is calculated using standard matrix math to isolate the robotBase_T_robotEEff function on the left hand side of the equation, as follows:

robotBase_T_robotEEff=robotBase_T_trajPlan*trajPlan_T_camEye*camEye_T_camTarget**camTarget_T_controlPoint*controlPoint_T_robotEEff Further, since the focal reference frame is desired to be matched to the trajectory plan, e.g., robotBase_T_trajPlan=robotBase_T_focalRefFrame one gets:

robotBase_T_robotEEff=robotBase_T_focalRefFrame*focalRefFrame_T_camEye*camEye_T_camTarget*camTarget_T_controlPoint*controlPoint_T_robotEEff The above recited equation can provide the pose of the robot to match the trajectory plan given the trajectory plan and the current poses of the digital surgical microscope and the patient reference frame.

An inverse kinematics routine is performed to determine a set of joint poses that satisfy the above equations and said set of joint poses may be sent to robot control module 820, which may then proceed in a stepwise manner toward said set of poses.

Since some parameters may change during the robot movement toward the desired set of poses required to move the focal reference frame toward being coincidental with the trajectory plan reference frame, a periodic update of the calculation of robotBase_T_robotEEff and its underlying enabling equations may be calculated and the movement "goal" of the robot control module.

Such update may provide, for example, a dynamic tracking of an arbitrary reference frame such as a navigation target attached to a surgical tool or other trackable tool. For example a spinal dilator such as Medtronic MetRx might have a navigated target mounted to it and the robot could track the center of the shaft of the MetRx toolset, thereby providing the microscope to continually image "down the tube" without any direct input needed from the user.

Since a trajectory is at its core a path, trajectory planning can represent many things such as: a desired surgical approach; a shunt installation path; a desired pedicle screw orientation, and/or an installation path for spine surgery.

The various embodiments described herein allow the trajectory to be drawn onscreen under user control, appearing due to the system's careful calibration processes in the correct location, orientation, size and perspective relative to the live surgical view.

For example, a trajectory can be corrected using this technology. The patient may be marked with real and virtual marks at the time of "best patient registration." Future movements of the patient relative to the patient navigation target (thereby degrading the registration accuracy) may be corrected by visually re-aligning the real and virtual marks. The correction thus applied can also be applied to the trajectory plan(s), thereby correcting said plan(s).

A trajectory can also be corrected using this technology, for example, when the patient's brain shifts due to pressure changes and gravity. A correction may be applied to the plan either manually by the user or under an automated brainshift correction algorithm. The correction can then be used by the system as described for trajectory plans in general.

XIII. Registration Correct Embodiment

FIG. 9 is a diagram of a surgical marking pen 3002 and a marking pen registration plate 3004 that may be used with the surgical navigation and visualization system 101 described in conjunction with FIGS. 1A to 8, according to an example embodiment of the present disclosure. As described herein, the surgical marking pen 3002 enables the surgical navigation and visualization system 101 to correct registration between patient volume scan data or other surgical templates and a live stereoscopic surgical view of a patient. The registration correction is provided in real-time during a surgical procedure.

The surgical marking pen 3002 is configured to generate a physical mark on a patient. The marking pen 3002 includes a first trackable target 3006. The marking pen registration plate 3004 includes a second trackable target 3008 and an indicator 3010.

The marking pen registration plate 3004 is configured to enable the surgical navigation and visualization system 101 to determine a transformation between the first trackable target 3006 and a pen tip 3012. This transformation enables the surgical navigation and visualization system 101 to determine a location of the pen tip 3012 based on a trackable location of the first trackable target 3004.

The first trackable target 3006 enables the surgical navigation and visualization system 101 to determine a position and/or orientation (e.g., a pose) of the surgical marking pen 3002. The second trackable target 3008 enables the surgical navigation and visualization system 101 to determine a position and/or orientation (e.g., a pose) of the marking pen registration plate 3004. The surgical navigation and visualization system 101 uses known poses to determine a position and/or transformation between the surgical marking pen 3002 and the marking pen registration plate 3004.

The indicator 3010 on the marking pen registration plate 3004 specifies a location to place the tip 3012 of the surgical marking pen 3002. The indicator 3010 may include a fiducial containing a feature able to specify a location for placement of the tip 3012 or otherwise accept the tip of the surgical marking pen 3002 in a consistent position (and optionally orientation.) The location (and optionally orientation) of the feature is known to within some accuracy relative to a reference frame of the second trackable target 3008. In other words, the indicator 3010 is located in a same plane and located at a known distance from the second trackable target 3008. The surgical navigation and visualization system 101 uses this known information between the indicator 3010 and the second trackable target 3008 in conjunction with the pose difference between the second trackable target 3008 and the first trackable target 3006 to determine a transformation between the first trackable target 3006 and a tip of the surgical marking pen 3002.

The use of the marking pen registration plate 3004 accordingly enables the surgical navigation and visualization system 101 to register a location of the pen tip 3012 to the first trackable target 3006. During a marking process, the surgical marking pen 3002 is removed from the marking pen registration plate 3004 and moved to an area of a patient to receive marks. The the surgical navigation and visualization system 101 uses the known transformation between the pen tip 3012 and first trackable target 3006 to virtually identify a location where the pen tip 3012 leaves a mark on a patient. This virtual location is stored in conjunction with patient volume scan data and/or surgical templates for subsequent registration correction.

After the marks have been created, the surgical navigation and visualization system 101 compares the virtual marks to locations of the physical marks shown within the live (stereoscopic) images. If the live marks move a threshold distance away from the virtual marks, the surgical navigation and visualization system 101 moves the patient volume scan data or surgical template such that the virtual and physical marks are aligned.

Figure 10:
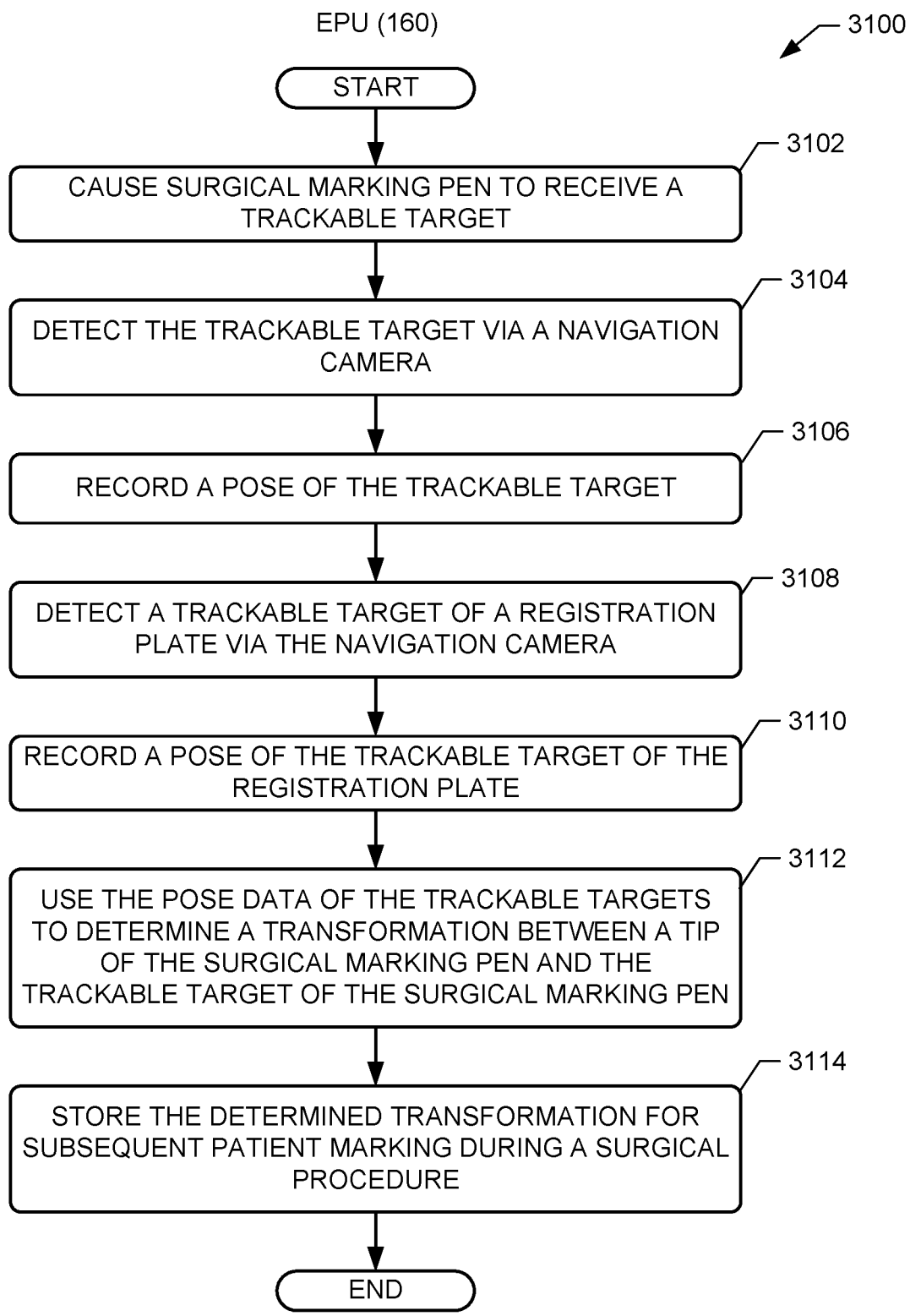
FIG. 10 is a flow diagram showing an example procedure for determining a relative pose between a tip of a surgical marking pen and a first trackable target, according to an example embodiment of the present disclosure.

FIG. 10 is a flow diagram showing an example procedure 3100 for determining a relative pose between a tip 3012 of the surgical marking pen 3002 and the first trackable target 3006, according to an example embodiment of the present disclosure. Although the procedure 3100 is described with reference to the flow diagram illustrated in FIG. 10, it should be appreciated that many other methods of performing the steps associated with the procedure 3100 may be used. For example, the order of many of the blocks may be changed, certain blocks may be combined with other blocks, and many of the blocks described are optional. Further, the actions described in procedure 3100 may be performed among multiple devices including, for example the embedded processing unit (EPU) 160, the navigation camera 200, robotic arm 120, and/or the DSM head 110.

The procedure 3100 begins when the first trackable target 3006 is affixed to the surgical marking pen 3002 at some time before an operator or the system 101 commences a marking pen registration procedure (block 3102). The marking pen registration procedure 3100 commences either via user direction or under automated system control (for example by a workflow control algorithm that dictates the ordering of events.) This marking pen registration procedure 3100 occurs at some time before the use of the pen to make marks.

The trackable target 3004 on the marking pen 3002 is caused to be made visible to the navigation camera 200 (block 3104). The EPU 160 is configured to detect, track, and record a pose of the trackable target 3004 (block 3106). The EPU 160 may detect and track the trackable target 3004 at a continual sample rate (for example 20 times per second).

Next, the second trackable target 3008 on the marking pen registration plate 3004 is caused to be made visible to at least the navigation camera 200 of the system 101 (block 3108). The EPU 160 detects and tracks at a continual sample rate (for example 20 times per second) the trackable target 3008 on the registration plate 3004, recording its pose in space at each sample time in a storage buffer of some non-zero size N (for example, the current sample and 20 prior samples are saved with older samples being overwritten by newer samples when the buffer is full) (block 3110).

The EPU 160 then calculates a markerTarget_T_markerTip transformation, which is a pose of the marker tip 3012 relative to the marker trackable target 3004 (block 3112). The EPU 160 may use Equation 1 below to determine this transformation. markerTarget_T_regPlateTarget is a relative transformation between the two trackable targets 3006 and 3008, as calculated from the navigation camera-provided poses of each trackable target 3006 and 3008 relative to the navigation camera 200. Additionally, regPlateTarget_T_fiducial is a relative transformation between the fiducial or indicator 3010 and the target 3008 on the registration plate 3004, and fiducial_T_markerTip is an identity matrix since the marker tip 3012 is presumed to be located exactly at the fiducial location. The regPlateTarget_T_fiducial is known by design and/or prior measurement. Note that markerTarget_T_regPlateTarget is calculated from the navigation camera space according to Equation 2 below, in which markerTarget_T_navCamera=navCamera_T_markerTarget.inverse( ).

markerTarget_T_markerTip=markerTarget_T_regPlateTarget*regPlateTarget_T_fiducial*fiducial_T_markerTip          Equation 1.

markerTarget_T_regPlateTarget=markerTarget_T_navCamera*navCamera_T_regPlateTarget          Equation 2.

The markerTarget_T_markerTip is calculated for each pair of incoming matrices navCamera_T_markerTarget and navCamera_T_regPlateTarget. In one embodiment, an operator indicates to the system 101 when the tip 3012 of the marker 3002 is placed in the fiducial 3010, and markerTarget_T_markerTip is stored for use throughout the remainder of the current marking process (block 3112). In another embodiment, referred to herein as the "positional delta method", the operator holds the registration plate 3004 and navigated marking pen 3002 (e.g., in their hands) and the system 101 detects user intent to store the target pose pair as discussed below.

A "delta" is calculated between the current calculated markerTarget_T_markerTip and its prior calculated value. A simple Euclidean distance between the translational parts of each of the matrices is used to assess the position difference. In this case, there is only interest in the positional distance delta. The orientation can be known optionally by using a rotational difference scheme based on quaternions, as described in the section about indicating and/or detecting when to record a virtual mark.

The positional delta is compared to a threshold, for example, of one millimeter. If the positional delta is below the threshold (or optionally "at or below the threshold") a Boolean logical flag named, for example, "belowThreshold" associated with each set of target transformation matrices stored in the storage buffer (described below) is set to true. Otherwise it is set to false. All such stored Boolean flags in the storage buffer are evaluated. If all are true, this indicates to the EPU 160 that the marker tip 3012 has been held in a constant position relative to the fiducial 3010 (to within the threshold tolerance and other tolerances including the navigation camera accuracy and precision) for the amount of time corresponding to how long it takes to fill the buffer. For example if the navigation camera 200 provides 20 samples per second of each target transformation matrix, and the buffer is 20 items deep, and the buffer is filled sequentially in order with one sample set per buffer entry, then determining that all the flags are true means that the marker tip 3012 has been held in a constant position relative to the fiducial 3010 for the one second threshold. This amount can be varied optionally by varying the sample rate or the buffer size or both, according to workflow requirements and preferences. When it is determined that the marker tip 3012 has been held in a constant position relative to the fiducial 3010 for an acceptable amount of time, markerTarget_T_markerTip is stored for use throughout the remainder of the current marking process or surgical procedure. To determine a final output for the transformation in some instances, an average of the many matrices gathered in the buffer may be calculated. The 'position' portion is averaged by the EPU 160 in a Euclidean space (x's averaged, y's averaged, z's averaged). Orientation may be averaged according methods described in a white paper titled "Averaging Quaternions", which is incorporated herein by reference (http://www.acsu.buffalo.edu/~johnc/ave_quat07.pdf).

In at least some aspects, if the marker tip 3012 is not placed on the fiducial 3010, then the matrix fiducial_T_markerTip will not be the identity matrix. In practice, such aspects will result in markerTarget_T_markerTip varying beyond some low threshold of movement since the operator is holding one or both of the marking pen 3002 and the marking pen registration plate 3004 in their hands in free space, and thus are moving one or both of them to some extent. The algorithm performed by the EPU 160 can be "tricked" to give a wrong result for markerTarget_T_markerTip, for example, by resting the marking pen registration plate 3004 on a table and putting the marker 3002 in a fixture with the tip 3012 in any random pose relative to the fiducial (e.g. 25 mm away from it.) The workflow of the application instructs the operator to hold the marker 3002 and the marking pen registration plate 3004 in their hands in free space to avoid such trickery. The example procedure 3100 then ends.

In an alternative embodiment, the registration plate 3004 may be omitted. Instead, the system 101 (e.g., the EPU 160) receives the pose transformation (markerTarget_T_markerTip) as a known transformation between the marker tip 3012 and the trackable target 3006 on the pen. In some instances, the pose transformation could be determined using computer vision techniques. In these instances, a computer vision-friendly pattern may be placed on a body or shaft of the pen 3002 to enable a computer vision algorithm performed by the EPU 160 to determine a pose transformation between the marker tip 3012 and the trackable target 3006 on the pen. In other instances, machine learning (e.g., deep learning including convolutional neural networks) may be used to identify the pen shaft for determining a pose transformation between the marker tip 3012 and the trackable target 3006 on the pen.

In at least some aspects, after a successful patient registration and before any subsequent activity which could alter the integrity of the patient registration, the operator either chooses to or is prompted by the system 101 to "lock in" the registration at this stage of the surgical procedure using the provided surgical marking pen 3002. In some aspects, the operator optionally poses the DSM head 110 such that its field of view is centered on and/or largely containing a portion of the surgical site of interest. Such posing enables viewing of the surgical site as well as concurrent overlay of some rendering of the patient volume data using the DSM head 110, thus enabling concurrent viewing and verification of placement integrity of real marks on the live patient anatomy and virtual marks in the patient volume space.

Such a surgical site location is found, for example, by using the surgical navigation and the just-recently-performed best-practice patient registration, optionally with a separate navigated probe pointer or instead using the navigated DSM head 110 as such a probe to explore the patient volume data as it is registered to the live patient anatomy. The patient pathology is made visible in the patient volume data and the corresponding parts (or those nearest or of optimal location relatively speaking) of the live patient anatomy easily located.

It is not strictly necessary for the DSM head 110 to view the surgical site region of interest at the time of marking. Such marking can happen in a dissociated manner with the real, physical marks visible to the operator's eyes, for example, but not by the DSM head 110, while the virtual marks are still recorded in the proper location in the patient volume data. In such a case, a separate visualization is provided to show the operator the recorded locations of the virtual marks in the patient volume data.

Figure 11A:
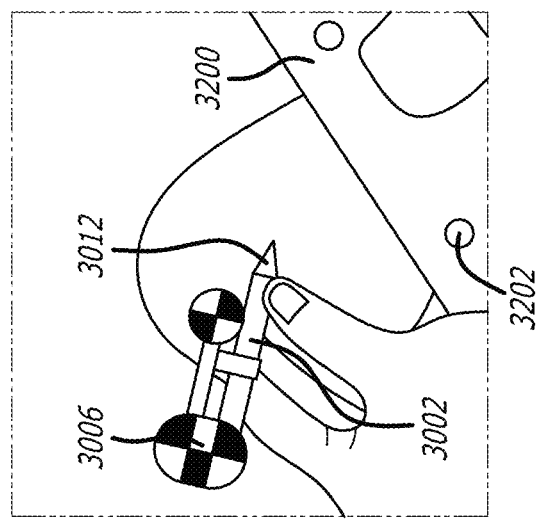
FIGS. 11A to 11C illustrate a typical marking session regardless of the activation mechanism utilized, according to an example embodiment of the present disclosure.
Figure 11B:
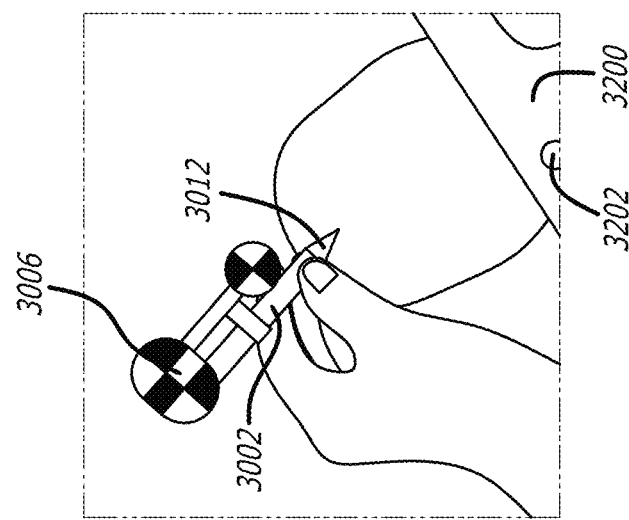
Figure 11C:
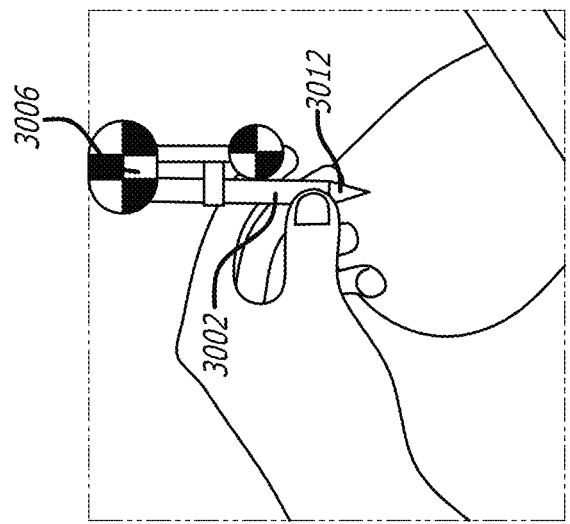

During the time of marking, the patient anatomy is presumed fixed in its securing device 240. The respective navigation targets on the patient reference frame and on the DSM head 110 are also presumed fixed during this time. In various aspects, the recording of a virtual mark may be activated by a variety of activation mechanism, which are detailed below and include, for example, a "Press and swivel" method, electronic communications, electro-optic communications, voice control, and a footswitch or other hardware-based method. Patient safety, workflow preferences, user convenience, and appropriateness to the surgical procedure, among other factors, may dictate which activation mechanism is or are used to perform such activation. FIGS. 11A to 11C illustrate a typical marking session regardless of the activation mechanism utilized.

The patient anatomy here is secured in a rigid securing device, such as a Mayfield clamp 3200, with a trackable navigation target affixed 3202. The reference frame of said target is referred to as the patient reference frame. Often this term is interchanged with the physical rigid securing device.

In this example, the best-practice patient registration method has been performed resulting in knowledge of the transformation (i.e., the "relative pose") between the trackable navigation target 3202 on the rigid securing device 3200 in which the patient is secured and features such as localized surface shape extracted from the live patient anatomy during the registration. A further step matches features extracted from live patient anatomy during the registration to features detected in the patient volume data, thus resulting in knowledge of the relative pose between the trackable target 3202 and the patient volume data, enabling the determination of the marker tip 3012 location in the patient volume data. This transformation matrix is referred to herein as patientData_T_patientRefFrame.

In one embodiment called herein the "press and swivel" method, a variation on the "positional delta threshold" method (described herein) is used to detect when the operator intends to record a virtual mark. The difference is that in this mode, the EPU 160 calculates the positional delta (as well as an extra orientational movement heuristic to be described) calculates between the navigated surgical marking pen tip 3012 and the patient reference frame. An optional "swivel" (i.e. angular movement of the marking pen body about its tip while the tip is held in place at the desired marking position) is detected by adding a "rotational delta threshold" to the "positional delta threshold" method. In this manner, the system 101 is configured to determine when the operator places and holds for some predetermined amount of time the tip 3012 of the navigated surgical marking pen 3002 onto some surface, which surface is presumed to be located on the patient anatomy. The optional "swivel" detection adds a further level of confidence in determining operator intent to place a mark. The "press and swivel" method is discussed below.

For the "press and swivel" method, the system 101 is placed into a marking mode, either under user control or under some automated system workflow control algorithm. The EPU 160 receives continually determines a pose of the first trackable target 3006 that is affixed to the surgical marking pen 3002. The EPU 160 determines the pose using data received from the navigation camera 200 including images, infrared feedback, etc. The EPU 160 may also determine a pose of patient anatomy using a navigation target that is affixed to a patient anatomy securing device 240. The EPU 160 may further determine a pose of the DSM head 110 using at least one trackable target connected to the DSM head 110. In this mode, a buffer of the EPU 160 stores the most recent N samples of each transformation matrix of interest, in this case navCamera_T_markerTarget and navCamera_T_patientRefFrameTarget and optionally navCamera_T_microscopeTarget. Also in this mode, the "positional delta" between the tip 3012 of the navigated surgical marking pen is calculated between successive samples of the navigated targets, as in the method described for the marking pen registration plate 3004.

When it is determined (via the same process used in the marking pen registration plate registration process 3004) that the marking pen tip 3012 has remained in the same position in the patient volume data space (equivalently: the marking pen tip 3012 has remained in the same position in the patient reference frame space), to within the related tolerances for a prescribed amount of time (e.g., one second), the EPU 160 creates a virtual mark. The EPU 160 may create the virtual mark in the patient volume data space according to Equations 3 to 5 below. Equation 5 is a homogeneous, three-dimensional point at the origin. Equation 3 gives the location of the marker tip 3012 in the patient data space.

Point_in_patientData=patientData_T_markerTip*Point_at_markerTip     Equation 3.

patientData_T_markerTip=patientData_T_patientRefFrameTarget*patientRefFrameTarget_T_navCamera*navCamera_T_markerTarget*markerTarget_T_markerTip     Equation 4.

Point_at_markerTip=$[0\ 0\ 0\ 1]^T$     Equation 5.

As an optional additional means of discerning user intent to make a mark, the orientation part of the pose of the marking pen 3002 in the patient volume data space (equivalently: the pose of the marking pen 3002 in the patient reference frame space) is evaluated while the tip 3012 is determined to be fixed in position in the space of interest. While the tip 3012 is determined to be stationary (to within some tolerance) in the space of interest, the orientation delta is evaluated (using some orientation delta heuristic such as quaternion delta.) The EPU 160 requires orientation variation above some threshold (as opposed to translational delta below some threshold) while the tip 3012 is considered stationary, for some amount of time (e.g., 1 second) in order to classify the navigated surgical marking pen tip location as a valid user input to become a virtual marking point.

Stated differently, the user presses the tip 3012 of the navigated surgical marking pen 3002 onto the desired location on the real, physical patient anatomy thus making a real mark, and holds the tip 3012 stationary (or nearly so) while swiveling the shaft that is by varying the pen shaft orientation relative to the patient anatomy (equivalently relative to the patient reference frame) above some threshold so that the system can discern user intent to place a virtual mark at the calculated position in patient volume space. This adds an additional level of confidence in determining the user intent for placing real and virtual marks. An advantage of the "press and swivel" method is that the user can express intent to place a mark using just the navigated surgical marking pen 3002 and of course the navigation system. Accordingly, the "press and swivel" method provided by the navigated surgical marking pen 3002 means that no additional means are required to record a virtual mark. For example, no user GUI interaction is required, no additional electronic hardware is needed, and no other software algorithm such as voice interpretation is required to interpret user intent to place a virtual mark.

Figure 12:
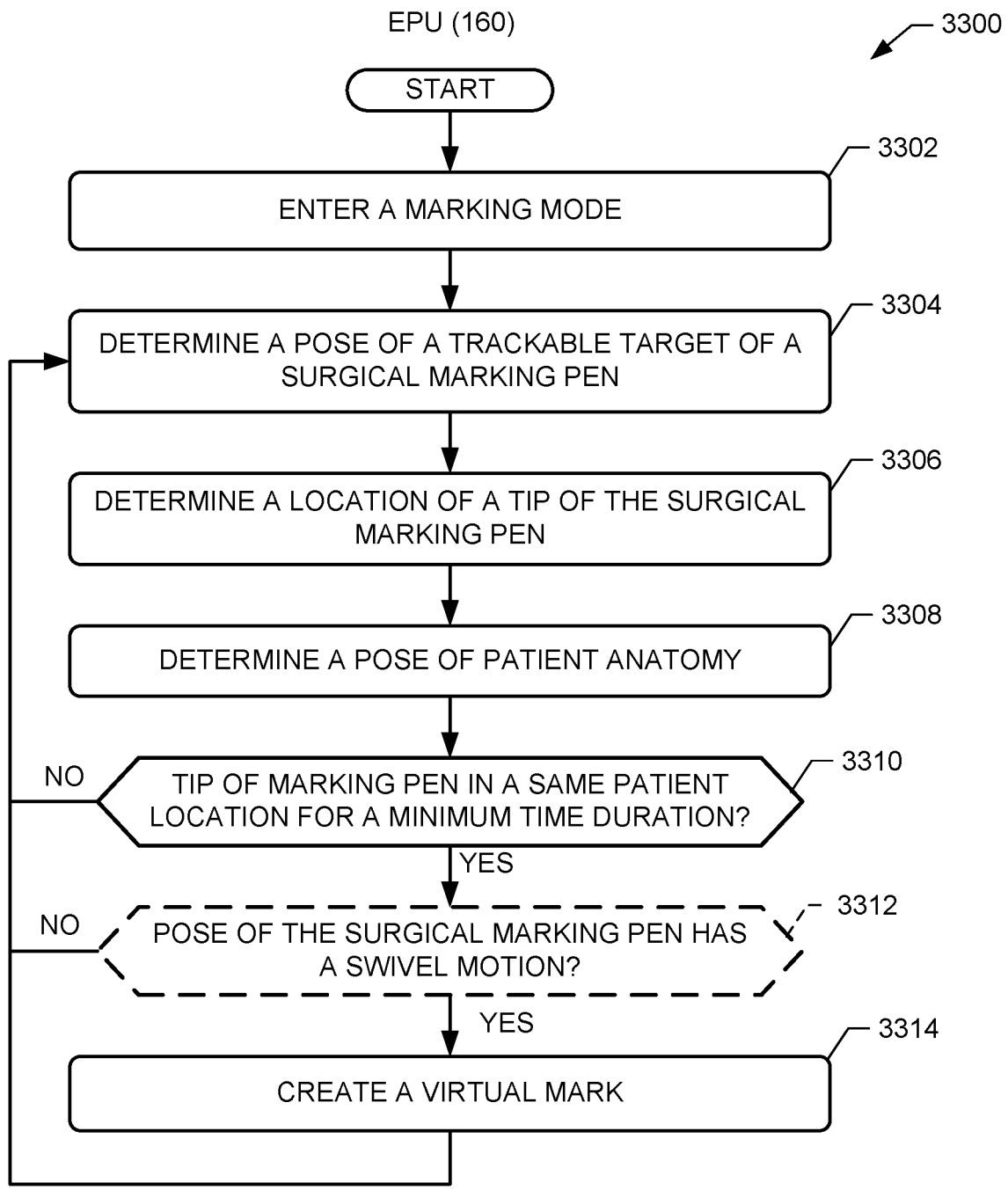
FIG. 12 is a flow diagram showing an example procedure for creating a virtual mark using a surgical marking pen, according to an example embodiment of the present disclosure.

FIG. 12 is a flow diagram showing an example procedure 3300 for creating a virtual mark using a surgical marking pen 3002, according to an example embodiment of the present disclosure. Although the procedure 3300 is described with reference to the flow diagram illustrated in FIG. 12, it should be appreciated that many other methods of performing the steps associated with the procedure 3300 may be used. For example, the order of many of the blocks may be changed, certain blocks may be combined with other blocks, and many of the blocks described are optional. Further, the actions described in procedure 3300 may be performed among multiple devices including, for example the embedded processing unit (EPU) 160, the navigation camera 200, robotic arm 120, and/or the DSM head 110.

The procedure 3300 begins when the ECU 160 enters a marking mode (block 3302). As described above, the ECU 160 is placed into a marking mode via operator control or via an automated system workflow control algorithm. The ECU 160 then begins analyzing data from the navigation camera 200 to determine pose information regarding the first trackable target 3006 of the surgical marking pen 3002 (block 3304). The ECU 160 uses the pose information of the first trackable target 3306 in conjunction with the previously stored transformation (e.g., the pen registration described in connection with FIG. 10) between the first trackable target 3306 and the tip 3012 of the surgical marking pen 3002 to determine a location of the tip 3012 (block 3306). EPU 160 may also determine a pose of patient anatomy using a navigation target that is affixed to a patient anatomy securing device 240 (block 3308). The EPU 160 may further determine a pose of the DSM head 110 using at least one trackable target connected to the DSM head 110.

The ECU 160 stores a location of the marking pen tip 3012 and/or a pose of the surgical marking pen 3002 to a buffer. The ECU 160 analyzes the data in the buffer to determine if the marking pen tip 3012 has remained in the same position in the patient volume data space (equivalently: the marking pen tip 3012 has remained in the same position in the patient reference frame space), to within the related tolerances for a prescribed amount of time (e.g., one second) (block 3310). If the pen tip 3012 has moved a distance than permitted by the tolerance within the prescribed amount of time, the procedure 3300 returns to block 3304 to determine a current pose of the surgical marking pen 3002.

If the pen tip 3012 has not moved (or moved within an allowed tolerance) within the prescribed amount of time, the ECU 160 determines if the pose of the surgical marking pen 3002 within the buffer has changed overtime and corresponds to a swivel motion (block 3312). This step may be omitted if the "press and swivel" method is not activated or implemented. If the ECU 160 determines the pose of the surgical marking pen 3002 within the buffer has changed overtime and corresponds to a swivel motion (e.g., an orientation of the first trackable target 3006 shows rotation around an axis), the ECU creates a virtual mark (block 3314). As described above, creation of the virtual mark may include storing a location of a virtual mark within a calculated position in a patient volume space. The ECU 160 may additionally or alternatively place the virtual mark within patient volume scan data and/or surgical templates. The ECU 160 may also display the virtual mark overlaid on the live images recorded by the DCM head 110. In other instances, the virtual mark is not displayed. The example procedure 3300 of FIG. 12 returns to block 3304 to enable the operator to create another virtual mark. The procedure 3300 ends when an indication is received to terminate the marking mode.

In some aspects of the present disclosure, the provided surgical marking pen 3002 may include an electronic communication activation mechanism to provide an input to enter a marking mode or make a virtual mark. A means to communicate the operator's intent to place a mark may be positioned at some location on or near the shaft of the navigated surgical marking pen 3002. In one embodiment, an electronic pushbutton switch is added to the marking pen 3002, or to a carrier into which the marking pen fits, such that the operator can readily activate said switch each time the operator desires to record a virtual mark. The switch may be in communication with a communications module, which may be in communication with the EPU 160. The communications module may communicate the state of the switch to the EPU 160. The possible states include "OPEN" and "CLOSED" (more easily understood as "PRESSED" and "NOT PRESSED".)

The physical means of communication in one embodiment is through a standard wired USB, and in another embodiment includes wireless Bluetooth®. Other embodiments are possible using any of many widely available means of communicating data to a processor. When a "PRESSED" state is communicated, the EPU 160 initiates the "STORE VIRTUAL MARK" subroutine. An example for such a switch exists on current surgical tools such as the Wallach™ handswitch operated push button cautery pencil provided by Cooper Surgical™.

In some aspects of the present disclosure, an electro-optic communications activation mechanism may signal a user's intent to mark. A user's intent to mark may be communicated by placing a light, such as a light emitting diode, somewhere on the marking pen 3002 shaft (or on or in a carrier into which the marking pen fits) with a power source and a switch enabling an operator to turn on the light momentarily to indicate that a virtual mark should be stored. In such aspects, a computer vision algorithm of the EPU 160 may be initiated to detect the presence in the visual field of a light being ON or from changing from the OFF state to the ON state and optionally back to OFF again. In some aspects, a color light is used that color correlates well to an image sensor being used, which may help simplify the detection algorithm. For example, a green LED may be used with a spectral bandwidth that falls well within the spectral range of the green filter of the image sensor's Bayer color filter array of the DSm head 110. Then, only the green channel is used in the detection algorithm. Alternatively, in some aspects, to facilitate the computer vision algorithm, instead of the light being changed between OFF and ON states, the light (such as a multicolor LED) changes between two colors such as red and green. An advantage of the electro-optic method is that it is computer vision based, and so therefore is not connected to the EPU 160 electrically or via wireless communications in any way.

In some aspects of the present disclosure, voice activation may enable an operator to use their voice to tell the EPU 160 when to record a virtual mark. This method has the advantage of hands-free operation, with no electronics getting near the patient. In some aspects of the present disclosure, a footswitch or other hardware-based method to enable an operator to indicate to the EPU 160 that a virtual mark is to be recorded. This method has the advantage of hands-free operation, with no electronics getting near the patient.

The present disclosure enables an operator to correct a misalignment in patient registration by storing a set of virtual marks in the same space as the patient data, in which virtual marks correspond to real physical marks made on the patient, and where each virtual mark is rendered in the same apparent respective position to the real marks. In order to be able to re-align a pattern of virtual marks to a pattern of real physical marks on the patient anatomy, the pattern must contain three or more points and it must be generally asymmetric. In some instances, the pattern can be distributed about the three-dimensional volume visible in the field of view of the DSP head 110 or navigation camera 200 as much as possible, which may help further reduce ambiguity when performing misalignment correction. In such instances, because this is not possible with just three points, more than three real marks and their respective virtual mark pairs may be used. Additionally, as the marking pen medium typically diffuses on the patient anatomy over time, having more marks can make it easier to perform misalignment correction in a "center of mass" type way.

In some aspects, to ensure a robust pattern of virtual marks, the EPU 160 may be configured to generate a suggested pattern, which is displayed on the mast-mounted touchscreen 171. All of the marks may be shown at one or provided one at a time in succession as virtual marks are made. In the latter case, the EPU 160 displays one suggested location for a mark, waits until the operator places a mark at or near that location, and then displays the next suggested location and so on. In some aspects, using the DSM head 110, the location in some 3D space of points on the surgical site visible to the camera can be determined via triangulation in regions with sufficient texture to allow unambiguous location of a given point in both "eyes" of the stereoscopic camera. Such aspects help facilitate the generation of a suggested pattern of marks to cover a sufficient 3D space.

In at least some aspects, marks are best made on rigid, natural patient anatomy features such as bony structures. The EPU 160 is configured to provide a registered overlay of the patient volume data over the live view. A planning phase built into the navigation software of the EPU 160 provides options to segment anatomical features such as bone from the rest of the patient data. In some aspects, using such a bone segmentation, as well as surface detection as described elsewhere herein, the EPU 160 may detect when bone is visible images recorded by the EPU 160 and a suggested pattern generation algorithm of the EPU 160 may use this information to show suggested mark locations on bony features. Such a feature might be useful at later stages in the surgical procedure, when bone is exposed. However, "tight" skin regions (skin near bone with little fatty tissue and/or muscle in between) are also identifiable in the patient data and may also be used optionally in the generation of suggested mark patterns on skin, which may be useful earlier in the procedure.

In some instances, drawing dots as the marks has some risk in that one dot looks much like any other dot. This risk is may be at least partially mitigated by the pattern requirements (e.g., asymmetric, many points etc.). A further mitigation is optionally taken by the EPU 160 to enable the operator to draw complex marks, such as letters of the alphabet. This gives individual identification to each mark. For example, such a technique is best for use with "user-activated" marking methods—such as electronic communications (e.g. switch control), voice control or footswitch—as opposed to "system detection" marking methods—such as "press and swivel"—because "press and swivel" is best at detecting single points whereas the other methods can activate mark recording over a time period. However, complex shapes can be approximated by using a plurality of dots in a closely-set complex pattern, thus making this method usable by all of the marking methods. In some instances, "spots"/dots may help minimize skin/anatomy movement.

In some aspects, the EPU 160 is configured to instruct the operator to place in each marking set one checkmark (V) or X or other pattern different from spots/dots, and to use this as a reference for rough posing the marking set during alignment correction. The EPU 160 then instructs the operator to use the remaining spots/dots as the true alignment verification. Such aspects may help balance the tradeoffs between simple dots and more complex marks.

In instances of drawing complex marks such as a line in the form of a checkmark (V), the line is effectively sampled in time based on a navigation sample rate and stored as a series of distinct (but closely positioned) points, and rendered to the overlay as such. In other embodiments the intent of drawing a line versus a point is discerned from marker tip 3012 movement and the resultant feature stored in various forms such as a series of points or one or more equations describing the line(s). The line(s) is/are then rendered to the overlay in a manner that more closely represents the related real physical mark.

When the indication is made or detected that the operator intends to store a virtual mark, the marker tip location in patient data space is calculated from Equation 3, which uses Equation 4. Equation 4 gives the 4×4 transformation matrix of the tip in the patient data space, and strictly speaking is a position plus an orientation. In one example, only the position is used for a given mark, but in other examples the orientation of the marker is used as well, for example, as a means of estimating the surface normal at that point.

In some instances, each position is stored in a storage buffer of the EPU 160 for later use. In some examples, the storage buffer is kept separate from the patient volume data and rendered to the overlay as a separate pass distinct from the patient data. In another embodiment the virtual marks are added to the patient volume data and rendered to the overlay as part of the patient volume data rendering pass.

In some aspects, each position and/or pattern is rendered as a small dot in a color that is distinct over the surgical background (for example bright green). Such aspects have the advantage of being highly accurate in the coordinate system of the patient volume data space. It is also easier to turn on and off separate from the rendering of the patient volume data.

In other aspects, the position data is blended with the patient data for example by modifying a single bit in the patient volume data that is in the form of a voxel cloud such as CT and MRI data. Such other aspects are accurate to the voxel accuracy of the data, which is typically less than what is possible with rendering each position and/or pattern as a small dot in a color distinct from the surgical background. However, it has the advantage of being able to complete the overlay rendering in one pass instead of two when, as is common, a volume renderer is used to visualize the data, which provides a time savings.

The overlay is updated with the new information at a rate not exceeding that of the display refresh and at a rate not exceeding the update rate of the navigation system. The virtual marks can be turned off and on at the operator's discretion. The rendering of the patient data can also be turned off and on at the operator's discretion, separate from the virtual marks. However, in some aspects, during the placement of the marks, the marks are always shown.

In some aspects, as the virtual marks are placed, they are immediately shown to the user in the overlay, which may be forced to be displayed when the EPU 160 is in "marking mode." This enables the operator to verify visually that the virtual marks are located "on top of" the respective real mark just made. To facilitate such verification, the marks may be optionally "blinked" on and off at a slow enough rate (e.g., on for one second, off for one second) to enable the operator to view the live patient anatomy "behind" the virtual mark and verify that indeed the real mark, corresponding to a given virtual mark, exists on the patient anatomy. When the operator indicates (or the EPU 160 prescribes) that marking mode is complete, a final verification step is initiated. This is where the EPU 160 provides the operator an option to view the whole marker pattern just made, judge its alignment to the real marks, and confirm the virtual marks are correct.

At this point, in at least some aspects, the best-practice patient registration may be "locked in" via the virtual mark and real mark pair set. Certain types of misalignment such as movement of the patient anatomy in its securing device 240 or movement of the navigation target 230 on the securing device 240 can now be detected by the EPU 160 using the current virtual mark set and comparing it to the real marks in the live view. Such misalignment can now be corrected by adjusting the overlay as will be described. Note that misalignment correction is optimized for this stage of the surgical procedure. As the procedure progresses and real marks altered, removed or destroyed, the ability to correct misalignment degrades for this mark set. The operator is advised continually throughout the case to initiate the generation of a new mark set to account for mark degradation.

In some aspects, for a given mark set, the DSM head 110 is intended to be fixed at one set of position values and optical settings (zoom and focus levels). The robotic arm 120 can be moved at will because the navigation system of the EPU 160 updates the overlay correctly over the live view (to within the accuracy of the registration and the system 101 at large) as the robotic arm 120, and hence the camera pose moves relative to the patient anatomy. In some aspects, the system 101 may be used at one robot position, which may produce desirable results since movement of any part of the system 101 can cause the probability of registration degradation to increase.

In some aspects, to enable automated return to the marking view, the robot position (in the form of joint angles) and the camera optical properties (zoom, focus, orientation, coupler settings) may be stored as part of (or associated with) the virtual mark set. This is referred to herein as the "robot camera waypoint" method. In some aspects, when a new mark set is made, the robot and camera settings at that time are stored with that set. This enables the EPU 160 to cause the robotic arm 120 and/or the DSM head 110 return to the same (or similar enough) conditions to enable misalignment detection and correction.

In some aspects, the position of the navigation target on the DSM head 110 relative to the navigation target on the patient reference frame is used as a "waypoint" for the robotic arm 120 and the DSM head 110. In various instances, the cart 154 on which the DSM head 110 is mounted might move at any time relative to the rigid patient anatomy securing device 240. In such instances, the "robot camera waypoint" method would be in error by that amount of movement. Thus, in some aspects, "waypoint" information is the pose of the navigation target 210 on the DSM head 110 relative to the navigation target 230 on the patient reference frame 240. A new matrix may be calculated and stored as part of the waypoint information according to Equation 6 below, in which $$\text{patientRefFrameTarget\_T\_navCamera} = \text{navCamera\_T\_patientRefFrameTarget.inverse( )}$$

$$\text{patientRefFrameTarget\_T\_microscopeTarget} = \text{patientRefFrameTarget\_T\_navCamera} * \text{navCamera\_T\_microscopeTarget} \quad \text{Equation 6.}$$

To return to the more true waypoint, a robot movement algorithm may be used by the EPU 160 in one embodiment using navigation system measurements of navCamera_T_patientRefFrameTarget and navcamera_T_microscopeTarget, and the matrix described by Equation 6 is calculated. The robotic arm 120 may be moved in such a way as to drive the error to below some threshold between the just-calculated matrix and the stored matrix. Positional error is calculated in a Euclidean sense and rotational error is calculated using a quaternion metric.

In some aspects, no return is made to the "true" relative pose patientRefFrameTarget_T_microscopeTarget recorded at the time of marking as, described by Equation 6, when evaluating the alignment of the current virtual mark set to the live, real physical marks. In such aspects, it may be sufficient to merely be able to view a plurality of real marks such that the pattern satisfies the "unambiguousness" qualities outlined elsewhere in the present disclosure. This is because the apparent respective poses of the virtual marks as rendered to the overlay are continually updated as new matrix values arrive from the navigation system of the EPU 160 for navCamera_T_patientRefFrameTarget and navCamera_T_microscopeTarget, and therefore said rendering appears to remain registered over the real live physical marks as long as no cause for misalignment occurs.

Even when such a cause does occur, in many cases the "slippage" is small enough such that the virtual mark set is still near enough (for example still at least partly visible onscreen) to the real mark set (for example also still at least partly visible onscreen) to allow misalignment correction to occur as described below. If it is not, the operator can "drive" the robotic arm 120 around (and in extreme cases move the cart 154, if the robotic arm cannot extend far enough) to cause the virtual mark set to become visible in the view near the real mark set. In some aspects, the operator is also offered means to adjust the overlay pose itself, as will be described.

In some aspects, in addition to storing the robotic arm and DSM head settings per virtual mark set, at the end of the marking session the operator is advised to remove the marking pen 3002 from the scene and a visual snapshot is taken either under user control or automatically by the EPU 160. In some instances, the visual snapshot help enable reregistration verification redundant to visual marks. For example, the visual snapshot image may serve as a secondary means of verifying registration. The visual snapshot shows the real marks, and by using this image as the overlay, for example with 50% opacity, this image is viewed over the live patient anatomy and the alignment of the real marks can be judged by the operator without any navigation system input required.

In at least some instances, this can be thought of as a low-cost simplified navigation system. The robot movement informs the camera optical axis and robot cart movement relative to the patient securing device is correctable using the real and virtual mark misalignment correction method(s) described herein.

In at least some aspects, this method includes that DSM head 110 optical settings and the pose of the robotic arm 120 relative to the patient anatomy be the same to within some tolerance as those when the image was taken. If either or both of the robot cart and patient reference frame have moved relative to each other, the alignment will appear incorrect. The operator is advised that indeed the visual image is merely a secondary form of verification and that the primary form (the virtual mark set alignment over the real mark set) takes priority.

In various instances during a surgical procedure, marks may get obscured, degraded, or removed from a patient through normal surgical activities and occurrences. In such instances, under EPU 160 prompt or user initiative, a new marking procedure may be undertaken by the operator and the resultant marking set used by the EPU 160 as the current marking set. The old set can be refreshed if possible, and new marks added for example in newly exposed areas of anatomy. Marks remaining from the previous marking set can be used to verify registration validity, and a misalignment correction preferably performed before the new marking session is begun.

In some aspects, the new set is made different enough from the previous set so that marks left over from the previous set and not used in the new set do not interfere with the new set. In some aspects, the new set is made with enough of the prior set of real marks still visible (and still aligned with virtual marks from the old set). Those prior marks can be used in the new set. To enable this, the prior set may be drawn in its original color and the new set is drawn in a new color, where the new color also is distinct from the surgical site background (for example the new set drawn in bright blue with a yellow border as compared with the old set being drawn in bright green.) The operator is advised to make marks over as many remaining useful real marks as possible (thereby "doubling" up those marks virtually). In some instances, the "blink" method (toggling the visibility of virtual marks at some rate for example one second on, one second off) is used optionally to make it easier for the user to determine whether virtual marks are indeed located in the same place as their real mark counterpart.

In various aspects, as the surgical procedure progresses the EPU 160 prompts the operator to occasionally verify the registration. When the operator accepts the prompt, the current virtual mark set is drawn as part of the overlay and the overlay shown over the live view. In some aspects, the operator is queried as to whether overlay correction is desired. If it is, a set of overlay correction tools are presented to the user. Often an assistant performs the overlay correction such that the operator (typically the surgeon) can remain in position to maintain workflow integrity such as keeping the surgical tools in the surgeon's hands and in the surgical site. Additionally or alternatively, advanced microscope controls enable the surgeon to control the overlay adjustment process while maintaining workflow integrity.

In some aspects, image processing techniques of the EPU 160 enable automatic detection of the real marks in the image stream of the DSM head 110. In one embodiment, a color or a plurality of colors that contrast with the surgical scene, for example, gentian purple are used for the real marks, thus facilitating automated detection of real mark areas. The term "areas" is used because some marking agents diffuse over time and thus do not present as the single spot or dot that was applied originally. In an alternate embodiment, the surgical marking pen 3002 deposits a biocompatible fluorescing agent as part or whole of its marking medium. Such material is made to "stand out" from its surroundings using an excitation light in conjunction with emission filtering (either physical in the light path, or in the image processing chain) such that the real marks are more readily located automatically by the EPU 160.

The poses in patient volume data space of the respective virtual marks are already known from the marking procedure. In some aspects, the respective poses of real and virtual marks are compared continually and an error metric generated (for example mean squared Euclidian distance difference among all points in each set). In some aspects, a pre-processing algorithm determines the most likely matching between real and virtual marks. Alternatively, a global minimization routine may be run on the whole set of real and virtual marks to determine the most likely pairing of real to virtual marks. The error metric may be compared to a threshold and a warning presented to the operator that the registration had degraded beyond the threshold when the threshold is exceeded.

In some aspects, when a misalignment is detected the operator is advised to pause the procedure at their discretion at an appropriate moment to perform a misalignment correction. It is possible that the operator opts to not correct the misalignment, based on surgical conditions or other reasons. It is typical that the operator prefers to judge the integrity of the alignment near critical times in the procedure, for example, when about to make an incision, when needing to disambiguate a current location, and when nearing the end of an approach with the objective still out of sight. In some aspects, the EPU 160 may enter a "misalignment correction" mode either under user manual control or via automated workflow.

In some instances, when selecting a marking set to use for misalignment correction, multiple marking sets may be selected, such as one each at various points in the surgical procedure. In such instances, the EPU 160 needs to know which marking set to use during misalignment correction. In some aspects, the operator optionally selects the set, but typically for simplicity only one set is made active at a time such that no explicit determination needs to be made as to which set to use for misalignment correction.

In some aspects, the EPU 160, either under user manual control or via automated workflow, returns the system 101 to the robotic arm 120 and DSM 110 waypoint settings stored with the marking set. As discussed previously, this could optionally include an attempt to drive the robotic arm 120, and hence the DSM head 110 and hence the navigation target 210 mounted on the DSM head 110 to or close to the pose it was in relative to the navigation target 230 on the patient reference frame 240 (thus attempting to match the calculated and stored as patientRefFrameTarget_T_microscopeTarget given in Equation 6).

As noted, the actual poses of the system 101 need not be reproduced exactly as misalignment of the pose of the virtual mark set relative to the real marks can be detected from many such poses. However, a significantly bad misalignment may require manual movement of robotic arm 120 to get physical marking set "in range." In some instances, the operator is asked to move the overlay to a pose "close" to the optimal registration of the virtual marks over the real marks, and any of the algorithms described previously are then run by the EPU 160 to complete the optimization.

In some aspects, a simplification option is presented to the operator in the case that the misalignment correction cannot proceed, for example, if the overlay is very far away from its intended pose. In that case the operator can specify to the EPU 160 that the overlay be "reset" and brought to the center of the display (or some other place visible to the operator) from wherever it currently is located. This is a somewhat extreme option, as it implies that the original registration information is badly incorrect and is essentially being discarded. But it offers the fastest way for the operator to "find" the overlay and get it back to where it is needed.

The EPU 160 may display virtual marks in such a manner as to enable misalignment correction. In various aspects, the EPU 160 either under user manual control or via automated workflow shows one or more of, sequentially or concurrently: virtual marks only, patient data overlay modified with virtual marks, and/or a visual snapshot from the time of marking, typically with some transparency (e.g. opacity at 50%) such that the real marks in the snapshot and the real marks on the patient are visible simultaneously.

In some aspects of the present disclosure, a visual-only method is used without a traditional device, and in some instances, without tracking the provided surgical marking pen 3002. In such aspects, initial patient registration is achieved by photogrammetry plus robot movement. Registration is "locked in" by making real marks in a given robot plus camera waypoint setting and taking a visual snapshot. An operator is able to correct continually (manually) robot/cart movement relative to patient and/or patient reference frame. In at least some aspects, a calibrated DSM head 110 is used. In such aspects, stereoscopic 3D images may be more accurate than 2D images and non-calibrated. In other aspects, stereoscopic 2D images and/or non-calibrated images may be used. In some aspects, two calibrated monoscopic cameras may be used. In other aspects, 3D surface features (e.g., natural patient marks) extracted via a multi-view (for example stereoscopic) camera of the DSM head 110 may be used in conjunction with or in place of real marks. For instance, multi-views or a stereoscopic view may be used to determine three-dimensional surface features of a patient's anatomy, such as skin protrusions, bone protrusions, muscle patterns, etc. for providing patient registration.

In various aspects of the visual-only method, a pro-active marking indication method may be used (for example, electronic switch or voice command; the "press and swivel" method is better suited for tracked marker). A tracked marker is enabled in an alternative embodiment by using trackable target(s) that fit into the reduced field of view of the DSM head 110 (as compared to a traditional navigation camera). The tracking algorithm of the EPU 160 in such an embodiment operates on the image stream from the DSM head 110. In various aspects, the visual-only method may help provide a low-cost navigation solution for the developing world. In various instances, patient registration verification may be needed by a surgeon whenever navigation needed/used.

In some instances, the virtual marking set might not be visible in the scene (e.g., as is the case with extreme misalignment, a rare case). In such instances, to ease the rough alignment of the virtual mark set to the real mark set in the case of misalignment, an option is made available to the operator to have the EPU 160 center the virtual mark set in the view. In some instances, this can move the virtual mark set far away from where it originated. To help mitigate this, in some instances, the original pose is stored for possible later restoration.

In some aspects, the pose of the overlay may be adjusted over the live scene until a virtual mark pattern matches a real mark pattern. In some instances, the adjustment may be manual by a user. In various aspects, the manual adjustment may be to adjust the DSM head pose relative to the patient anatomy or to adjust the overlay pose relative to the navigation target on the DSM head 110.

When adjusting the DSM head pose relative to the patient anatomy, the calculated result of the virtual mark pose relative to the navigation target 210 on the DSM head 110 is held constant and the DSM head 110 is moved until the misalignment is corrected. This has the advantage of using movements familiar to the operator. When adjusting the overlay pose relative to the navigation target 210 on the DSM head 110, the pose of the overlay is adjusted without moving anything else, as described below. This is nominally equivalent to adjusting the overlay pose relative to the navigation target 230 on the patient reference frame 240 since the robot cart 154 and DSM head 110 are presumed to remain largely fixed in place during this part of the misalignment correction process. In some aspects, there may be three degrees of freedom. Such aspects enable an operator to re-pose an overlay in x-y directions in screen space (screen space is display space of the mast-mounted touchscreen 171) and to rotate overlay about viewing axis. In other aspects, there may be more than three degrees of freedom for re-posing the overlay. For example, there may be the z-direction (e.g., into and out of a display screen), or a rotation about the other two axes (e.g., x and y axes). Note that, in some instances, for simplicity adjustments are constrained to the six degrees of freedom mentioned. For example, in some instances, no scale adjustment is allowed, nor are adjustments to any of the camera parameters such as zoom, focus or intrinsic or extrinsic parameters in this mode.

Figure 13A:
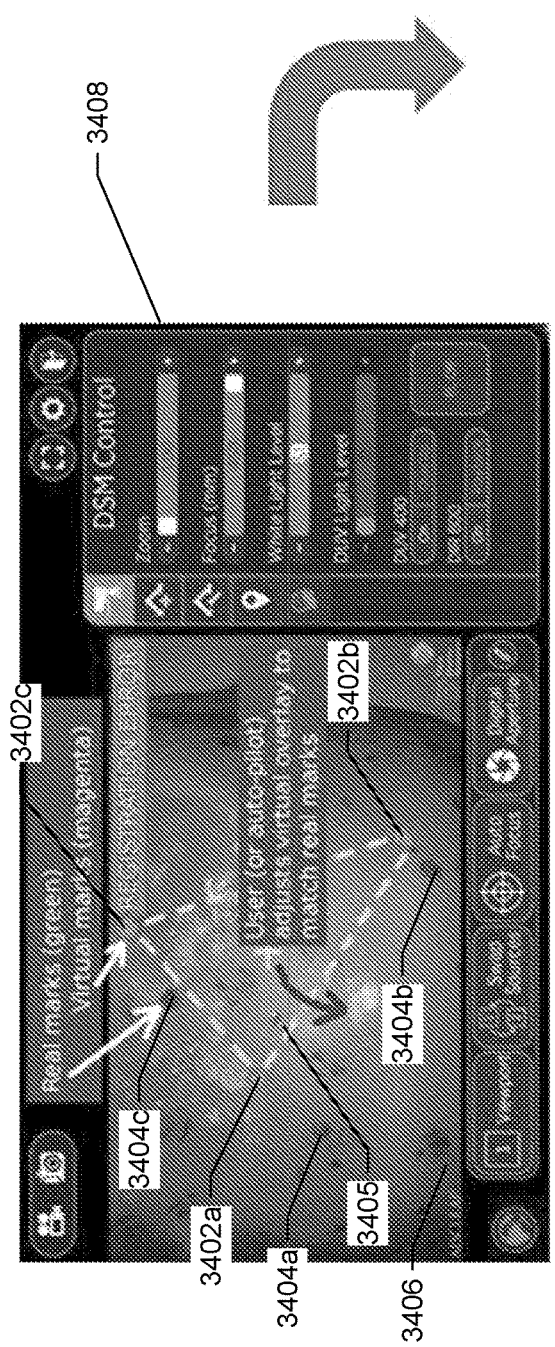
FIGS. 13A and 13B are diagrams a misalignment correction process, according to an example embodiment of the present disclosure.
Figure 13B:
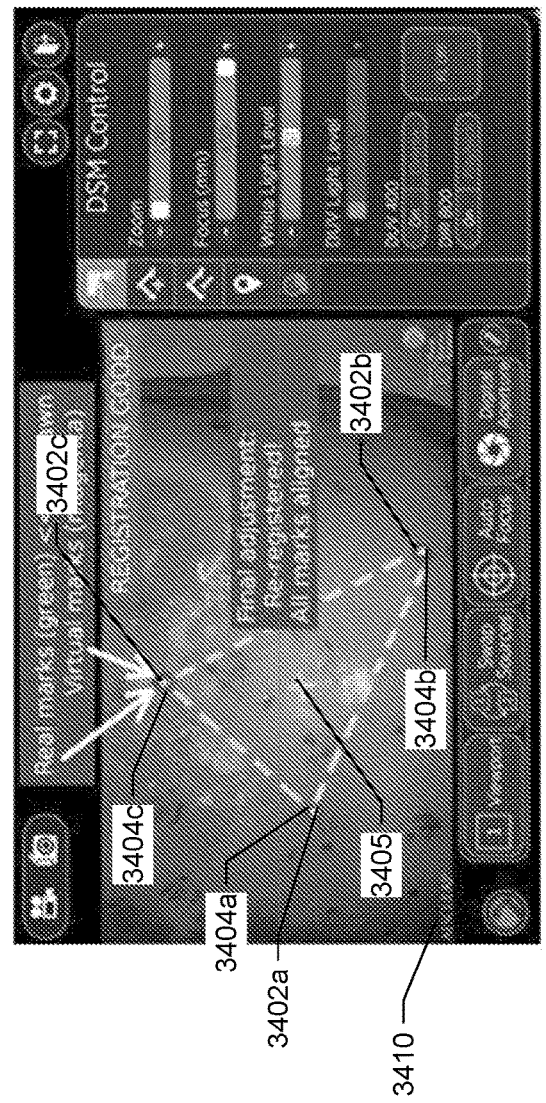

In other instances, the adjustment of the pose of the overlay over the live scene may be automatically performed by way of one or more algorithms of the EPU 160 that calculate the pose adjustment needed to correct the misalignment. FIGS. 13A and 13B illustrate a misalignment correction regardless of the method used. In some instances, such as the illustrated one, an asymmetric shape may be described by the marks.

FIG. 13A shows a registration error or misalignment between locations of virtual marks 3402a, 3402b, and 3402c and respective locations of physical marks 3404a, 3404b, and 3404c. As shown the virtual marks 3402a, 3402b, and 3402c are displayed in conjunction with patient space data 3405, which is a triangle with a crosshair. The virtual marks 3402a, 3402b, and 3402c and the patient space data 3405 are overlaid by the EPU 160 on live image data 3406 recorded by the DSM head 110. The physical marks 3404a, 3404b, and 3404c are shown in the line image data 3406. FIG. 13A also shows a control interface 3408 for changing a zoom, focus, and light level of the DSM head 110.

FIG. 13B shows a diagram after the EPU 160 causes the robotic arm 120 and/or the DSM head 110 to move in a specified manner such that the locations of the virtual marks 3402a, 3402b, and 3402c and are aligned with the respective locations of physical marks 3404a, 3404b, and 3404c. Such movement may include causing the DSM head 110 to move laterally along an x-axis, a y-axis, and/or a z-axis and/or rotate around a yaw, pitch, and/or roll axis. In some embodiments, the EPU 160 iteratively causes the robotic arm 120 to move a specified distance and then subsequent images 3410 are analyzed to determine a new distance difference between each of the locations of the virtual marks 3402a, 3402b, and 3402c and the respective locations of physical marks 3404a, 3404b, and 3404c.

Figure 14:
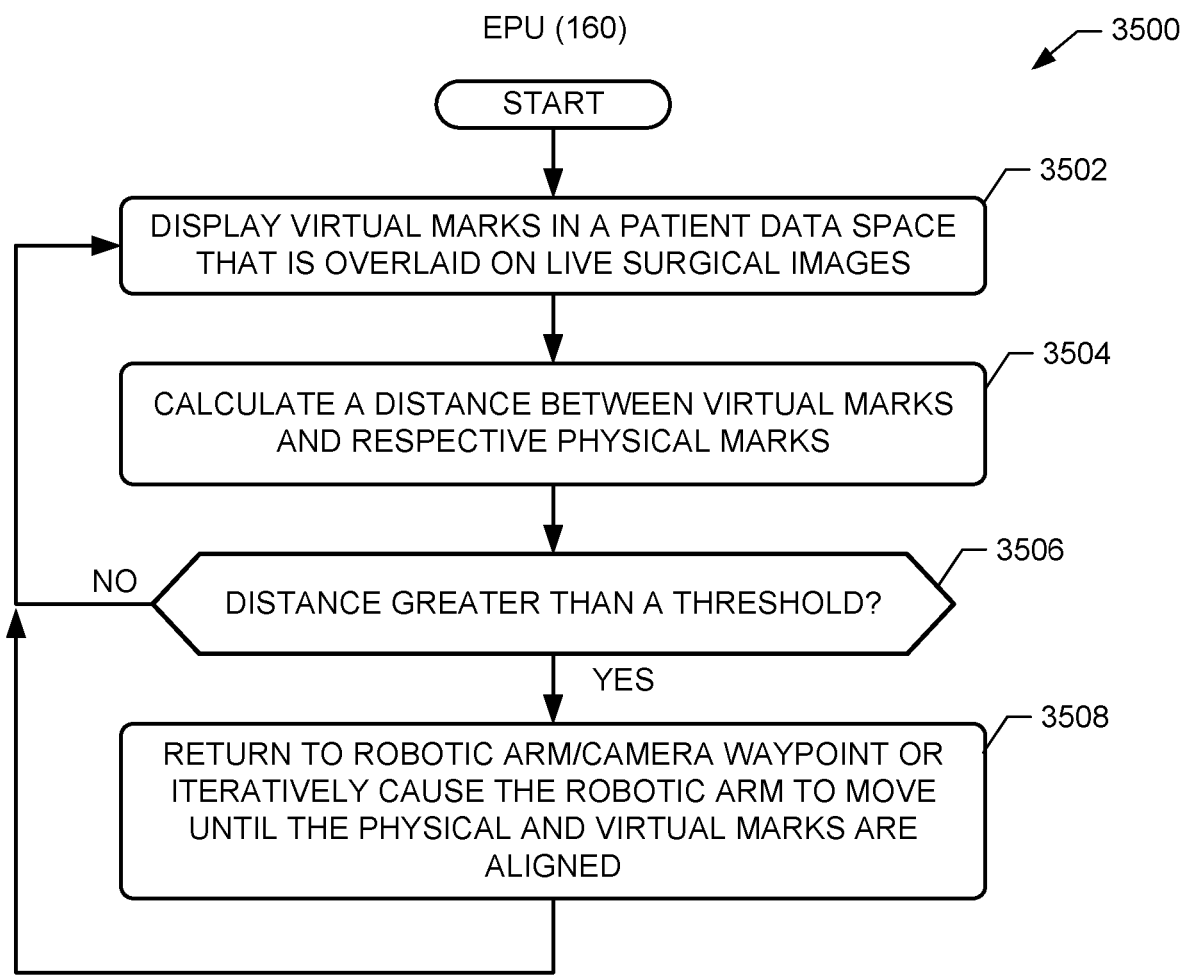
FIG. 14 is a flow diagram showing an example procedure for correcting an alignment or registration error between virtual marks and physical marks on a patient, according to an example embodiment of the present disclosure.

FIG. 14 is a flow diagram showing an example procedure 3500 for correcting an alignment error between virtual marks and physical marks on a patient, according to an example embodiment of the present disclosure. Although the procedure 3500 is described with reference to the flow diagram illustrated in FIG. 14, it should be appreciated that many other methods of performing the steps associated with the procedure 3400 may be used. For example, the order of many of the blocks may be changed, certain blocks may be combined with other blocks, and many of the blocks described are optional. Further, the actions described in procedure 3500 may be performed among multiple devices including, for example the embedded processing unit (EPU) 160, the navigation camera 200, robotic arm 120, and/or the DSM head 110.

The procedure 3500 begins when the EPU 160 displays one or more virtual marks in a patient data space that is overlaid on live surgical images showing corresponding physical marks(s) (block 3502). The EPU 160 next calculates a distance between the one or more virtual marks and the respective physical marks (block 3504). The EPU 160 may calculate an Euclidean distance between "closest" pairs of respective virtual and physical marks. The EPU 160 next compares the distances to a threshold (block 3506). The distance and threshold may be specified in pixels or lengths based on a number of pixel and known pixel size. The EPU may compare the distance for each virtual and physical mark pair to the threshold or average the distances of the pairs and compare the average to the threshold. The threshold may be 0.1 mm, 0.2 mm, 0.5 mm, 1.0 mm, 2 mm, 5 mm, 1 cm, etc. In some instances, the threshold may be adjusted based on a known magnification level of the DSM head 110. For example, a threshold of 1 mm may be adjusted to 0.5 mm is the magnification level is increased by 2×.

If the threshold is not met, the EPU 160 is configured to determine that the virtual marks have not drifted or become misaligned sufficient enough to warrant adjustment. The EPU 160 returns to block 3502 for the next surgical image. However, if the threshold is met, the EPU 160 is configured to return the robotic arm 120 and/or the DSM head 110 to a waypoint that corresponds to the virtual marks (block 3508). Alternatively, the EPU 160 is configured to use the calculated distances to determine pose adjustments to the robotic arm and/or the DSM head 110 to cause the virtual and physical marks to align. The EPU 160 then transmits instructions to the joint motors of the robotic arm 120 to move to the specified position/orientation and/or instructions to the DSM head 110 to proceed to certain optical properties, such as a zoom level or focal depth. In some embodiments, the EPU 160 moves the robotic arm 120 and/or adjusts the DSM head 110 iteratively. In these embodiments, the EPU 160 uses subsequent images to calculate new distances between the physical and virtual marks, and uses these new distances to determine further pose adjustments. The example procedure 3500 then returns to block 3502 for subsequent surgical images from the DSM head 110.

In some aspects, real, physical marks may be detected by the EPU 160 using computer vision. The real marks (e.g., the marks 3404a, 3404b, and 3404c of FIG. 13) are typically made using a media that contrasts well with the surgical site. This facilitates detection and localization by image processing techniques. Diffusion of the medium over the passage of time since the original mark was made is handled by taking a center of mass of the detected area or volume as the location of the real mark. As mentioned, in some aspects, a fluorescent marker medium may be used either in conjunction with the usual marker medium or by itself to facilitate computer vision detection, with an appropriate excitation light and emission filtering put in place during the detection. As mentioned, in some aspects, the color of the marker is adjusted to facilitate computer vision detection.

In some aspects, a pose of the detected real mark(s) in the patient data space may be calculated by the EPU 160. In such aspects, the pose in the patient data 3D space of the detected real mark(s) may be calculated using the calibrated stereoscopic camera of the DSM head 110 and the detected positions in each of the two eyes of said stereoscopic camera using triangulation. The pose of the camera space is known from prior calibration relative to the navigation target 230 on the DSM head 110, and thus the pose of a given detected real mark in patient data space is given by Equation 7 below, in which patientData_T_cameraEyePoint is given by Equation 8 below.

$$\text{realMarkPose}_{inPatientDataSpace} = \text{patientData\_T\_cameraEyePoint} \ast \text{realMarkPose}_{inCameraEyePointSpace} \qquad \text{Equation 7.}$$

$$\text{patientData\_T\_cameraEyePoint} = \text{patientData\_T\_patientRefFrameTarget} \ast \text{patientRefFrameTarget\_T\_navCamera} \ast \text{navCamera\_T\_microscopeTarget} \ast \text{microscopeTarget\_T\_cameraEyePoint} \qquad \text{Equation 8.}$$

In some instances, after detection of the location of the real marks in the patient data 3D space, an optimal transformation may be calculated by the EPU 160 using an optimization routine that minimizes an error metric between the pose of the real mark set and the pose of the virtual mark set by calculating Euclidean distances between "closest" pairs of respective real and virtual marks and minimizing that distance by varying the relative pose (also known as the relative transformation) between the two sets. Each virtual mark is located in the patient volume data space using Equation 3. Thus, the virtual marks are located in the patient data space. The location of the camera eye point of the DSM head 110 in the patient data space is given by Equation 8.

In some aspects, for simplicity as well as to address a typical source of significant misalignment, it may be assumed that patientData_T_patientRefFrameTarget is the source of misalignment. In other embodiments, other transformations are made correctable in a manner similar to that described here for patientData_T_patientRefFrameTarget.

In some aspects, a transformation that is being solved is effectively a correction to patientData_T_patientRefFrameTarget, where the correction is referred to here as patientData_T_patientRefFrameTargetCORRECTION and is combined with the original matrix to form a corrected matrix provided by Equation 9 below. Equation 8 may be updated to Equation 10 below to denote the correct math.

$$\text{patientData\_T\_patientRefFrameTargetCORRECTED} = \text{patientData\_T\_patientRefFrameTargetCORRECTION} \ast \text{patientData\_T\_patientRefFrameTargetWRONG} \qquad \text{Equation 9.}$$

where "patientData_T_patientRefFrameTargetWRONG" is actually the original patientData_T_patientRefFrameTarget matrix.

$$\text{patientData\_T\_cameraEyePointCORRECTED} = \text{patientData\_T\_patientRefFrameTargetCORRECTED} \ast \text{patientRefFrameTarget\_T\_navCamera} \ast \text{navCamera\_T\_microscopeTarget} \ast \text{microscopeTarget\_T\_cameraEyePoint} \qquad \text{Equation 10.}$$

When the registration degradation is corrected manually by a surgeon using camera moves via the robot (or is corrected automatically), the correction patientData_T_patientRefFrameTargetCORRECTED is found directly as follows, with no interim CORRECTION term. The general equation for determining the view of the patient data onscreen is:

$$\text{patientData\_T\_cameraEyePoint} = \text{patientData\_T\_patientRefFrameTarget} * \text{patientRefFrameTarget\_T\_navCamera} * \text{navCamera\_T\_microscopeTarget} * \text{microscopeTarget\_T\_cameraEyePoint} \quad \text{Equation 10a}$$

Solve for patientData_T_patientRefFrameTarget:

$$\text{patientData\_T\_patientRefFrameTarget} = \text{patientData\_T\_cameraEyePoint} * \text{microscopeTarget\_T\_cameraEyePoint.inverse} * \text{navCamera\_T\_microscopeTarget.inverse} * \text{patientRefFrameTarget\_T\_navCamera.inverse} \quad \text{Equation 10b}$$

Add "ORIG" suffix to denote the starting point: patientData_T_cameraEyePointORIG is incorrect and needs to be corrected; it is presumed that the bulk of the error lies in patientData_T_patientRefFrameTarget:

$$\text{patientData\_T\_cameraEyePointORIG} = \text{patientData\_T\_patientRefFrameTargetORIG} * \text{patientRefFrameTarget\_T\_navCameraORIG} * \text{navCamera\_T\_microscopeTargetORIG} * \text{microscopeTarget\_T\_cameraEyePointORIG} \quad \text{Equation 10c}$$

Start the correction phase:
The system holds the overlay in place onscreen. This is equivalent to holding all terms constant in the above equations.
The system disables zoom and focus adjustments.
The system instructs the user to move the camera until the overlay is registered to the live marks.
The system records the new navCamera_T_microscopeTarget as navCamera_T_microscopeTargetNEW.
The system calculates the correction as follows; while keeping the original patientData_T_patientRefFrameTarget. Also, microscopeTarget_T_cameraEyePoint is a constant here. A new value is read for navCamera_T_microscopeTarget. Finally, a new value is read for patientRefFrameTarget_T_navCamera in case the navigation camera gets bumped or otherwise moved:

$$\text{patientData\_T\_patientRefFrameTargetCORRECTED} = \text{patientData\_T\_cameraEyePointORIG} * \text{microscopeTarget\_T\_cameraEyePoint.inverse} * \text{navCamera\_T\_microscopeTargetNEW.inverse} * \text{patientRefFrameTarget\_T\_navCameraNEW.inverse} \quad \text{Equation 10d}$$

Finally solve for the corrected patientData_T_cameraEyePoint:

$$\text{patientData\_T\_cameraEyePointCORRECTED} = \text{patientData\_T\_patientRefFrameTargetCORRECTED} * \text{patientRefFrameTarget\_T\_navCamera} * \text{navCamera\_T\_microscopeTarget} * \text{microscopeTarget\_T\_cameraEyePoint} \quad \text{Equation 10e}$$

Equation 10e is used going forward. It should be noted that this method can be used at any time during the procedure to correct the registration of the overlay to the live scene, even without adding physical marks and without prior recognition of patient anatomical features, as long as there are features recognizable and matchable between the live view and the overlay. Further, the above procedure may be performed iteratively so that a sequence of pose data is determined during movement of the camera and/or robotic arm. A final registration correction transformation is calculated as a pose delta between a first pose and a final pose of the subsequent poses.

In other embodiments, where corrections to other transformations in the equation are made available to the operator, the given matrix correction is constructed in a similar manner by the EPU 160. Some real marks might be missed or not visible to the detection scheme of the EPU 160, and/or there might be extra, incorrectly detected real marks. In at least some instances, only a relevant portion of physical marks need be visible for alignment correction. Some can be hidden or removed or destroyed as long as the requirements for a relevant unique pattern are still met. The optimization routine performed by the ECU 160 considers "outliers" and scrubs the real mark data of these using an algorithm such as RANSAC. Missing marks may also be handled by the algorithm of the ECU 160 and by the pattern requirements automatically, for instance, the minimal error metric is still met because missing marks contribute zero to the overall error.

In some aspects, in-clamp misalignment correction may be performed. In such aspects, marks must be located on patient anatomy. In an example, at least a relevant portion of natural, physical marks must be visible to DSM head 110 after a robot and camera waypoint is restored to enable alignment correction for that waypoint/mark set.

In an example, the provided method may include using physical targets mounted on patient anatomy. Physical targets such as a miniaturized April tag may be mounted to, for example, a skin adhesive or a bone screw, and the target is mounted to the patient. Then, the target is registered to the system by the EPU 160 using an operator activated method while the target is visible to the target-viewing DSM head 110 or navigation camera 200. This becomes a real-virtual mark pair. Since such targets are two-dimensional and rotationally invariant, a single target may be sufficient to serve as a complete mark set.

In another example, the provided method may include generating a bone-mountable mini-pattern. After a good registration (and/or in conjunction in one embodiment with structured-light scanner-based registration) an operator may inject a plurality of bone-mountable mini-patterns into portions of exposed bone (for example a vertebra in a spinal case). A computer-vision-trackable pattern and/or color may be formed by the EPU 160 onto an exposed surface of a bone-mountable mounting post, which exposed surface is made to remain visible to the stereoscopic DSM head 110 as a "real mark." The trackable pattern and/or color may be recognized by a computer vision algorithm of the EPU 160 after placement (which placement is indicated in various embodiment by the operator through one of a subset of the methods used to indicate positioning of the real and virtual surgical marking pen). A virtual mark is recorded for said the post upon such indication.

In another embodiment of such an example, the pattern is kept hidden by the placement tool until after placement, and the activation of storing a virtual mark is made upon first detection of the trackable pattern and/or color in a new position. Alternatively, each post is festooned with a different pattern and/or color, to simplify the detection of newly placed posts.

In yet another embodiment, the EPU 160 may operate in conjunction with a non-navigated pen. In this example, the navigation camera 200, the DSM head 110, or another device is configured to project crosshairs or another indicator into a portion of a patient. An operator uses a pen to place a mark at a spot of the crosshairs or indicator. The operator provides an input that a virtual mark should be created, or the EPU 160 automatically detects that a virtual mark should be generated after detecting the physical mark. In either instance, the EPU 160 has a known correlation of the crosshairs or indicator to the patient data space since from calibration and navigation it is always known where a focal point of the camera 200 or DSM head 110 is located in the patient space. The input causes the EPU 160 to designate a virtual mark at this known location. The operator may then cause the crosshairs or indicator to move to a new location using the robotic arm 120 to generate another virtual mark.

CONCLUSION

As used herein, "about," "approximately" and "substantially" are understood to refer to numbers in a range of numerals, for example the range of −10% to +10% of the referenced number, preferably −5% to +5% of the referenced number, more preferably −1% to +1% of the referenced number, most preferably −0.1% to +0.1% of the referenced number.

Furthermore, all numerical ranges herein should be understood to include all integers, whole or fractions, within the range. Moreover, these numerical ranges should be construed as providing support for a claim directed to any number or subset of numbers in that range. For example, a disclosure of from 1 to 10 should be construed as supporting a range of from 1 to 8, from 3 to 7, from 1 to 9, from 3.6 to 4.6, from 3.5 to 9.9, and so forth.

It will be appreciated that all of the disclosed methods and procedures described herein can be implemented using one or more computer programs or components. These components may be provided as a series of computer instructions on any conventional computer readable medium or machine-readable medium, including volatile or non-volatile memory, such as RAM, ROM, flash memory, magnetic or optical disks, optical memory, or other storage media. The instructions may be provided as software or firmware, and/or may be implemented in whole or in part in hardware components such as ASICs, FPGAs, DSPs or any other similar devices. The instructions may be configured to be executed by one or more processors, which when executing the series of computer instructions, performs or facilitates the performance of all or part of the disclosed methods and procedures.

It should be understood that various changes and modifications to the example embodiments described herein will be apparent to those skilled in the art. Such changes and modifications can be made without departing from the spirit and scope of the present subject matter and without diminishing its intended advantages. It is therefore intended that such changes and modifications be covered by the appended claims.

What is claimed is:

1. A system comprising:
a surgical marking pen including a first trackable target, the surgical marking pen configured to generate a physical mark on a patient;
a marking pen registration plate including a second trackable target and an indicator specifying a location to place a tip of the surgical marking pen;
a navigation camera, wherein the first and second trackable targets are posed at least some of the time such that they are visible to the navigation camera;
a memory storing machine-readable instructions; and
a processor in communication with the memory, wherein execution of the machine-readable instructions causes the processor to:
perform an initial patient registration that registers a patient volume space of virtual positional data points to physical positional points of at least a portion of a patient,
perform a pen registration that determines a transformation between a tip of the surgical marking pen and the first trackable target by determining relative poses between the first trackable target and the second trackable target when the tip of the surgical marking pen is placed on the indicator and the first and second trackable targets are viewable by the camera,
record a virtual mark in the patient volume space in response to an activation action performed by the surgical marking pen using the pen registration, the virtual mark being a virtual positional data point that corresponds to the physical positional point of a physical mark generated on the patient by the tip of the surgical marking pen, and
cause the patient volume space of the virtual positional data points and the recorded virtual mark to be displayed in an overlaid manner over live image data recorded by a surgical camera on one or more displays.

2. The system of claim 1, wherein the activation action is one of a press and swivel action, an electronic communication activation mechanism, an electro-optic communications activation mechanism, voice activation, or a footswitch or other hardware-based method.

3. The system of claim 1, wherein the activation action includes maintaining a positioning of the surgical marking pen relative to a patient for a predetermined amount of time.

4. The system of claim 1, wherein the patient volume space includes patient volume scan data from magnetic resonance imaging ("MRI") images, diffusion tensor imaging ("DTI") images, or computed tomography ("CT") images or a surgical template.

5. The system of claim 1, wherein execution of the machine-readable instructions further causes the processor to display recommended locations for virtual marks.

6. The system of claim 5, wherein the recommended locations include three or more points provides in an asymmetric shape.

7. The system of claim 1, wherein the virtual mark includes at least one of a dot, a line, a symbol, or a character.

8. The system of claim 7, wherein execution of the machine-readable instructions further causes the processor to sample in time portions of the at least one line, symbol, or character as distinct points or one or more equations describing a line segment formed by joining at least some of the distinct points.

9. The system of claim 1, wherein the indicator of the marking pen registration plate includes at least one of a fiducial containing a feature able to accept the tip of the surgical marking pen or a two-dimensional crosshair graphical indication.

10. The system of claim 1, further comprising the surgical camera as a stereoscopic or visualization camera.

11. The system of claim 1, wherein execution of the machine-readable instructions further causes the processor to obtain the virtual positional data points that are related to the physical positional points of at least the portion of the patient by recording one or more images of physical positional points of at least the portion of the patient at different poses.

12. The system of claim 1, wherein execution of the machine-readable instructions further causes the processor to record the virtual mark before draping of the patient.

13. The system of claim 1, wherein execution of the machine-readable instructions further causes the processor to:
compare locations of the virtual mark to the physical mark generated on the patient as shown in the live image data;
determine when a distance between the location of the virtual mark and the location of the physical mark exceeds a threshold; and
cause a misalignment alert to be displayed on the single display.

14. The system of claim 13, wherein execution of the machine-readable instructions further causes the processor to:
enter a correction phase when a request is received from an operator or the distance between the location of the virtual mark and the location of the physical mark exceeds the threshold;
record or determine a first pose of the surgical camera and a robotic arm supporting the surgical camera;
cause at least one of the surgical camera or the robotic arm to move such that the virtual mark is aligned with the physical mark;
record or determine a second pose of the surgical camera and the robotic arm; and
calculate a registration correction transformation as a pose delta between the second pose and the first pose of the surgical camera and the robotic arm.

15. The system of claim 14, wherein execution of the machine-readable instructions further causes the processor to:
(i) receive an input from an operator to move the at least one of the surgical camera or the robotic arm by a specified distance or degree of rotation; and
(ii) cause the at least one of the surgical camera or the robotic arm to move by the specified distance while keeping the virtual mark stationary with respect to a camera space of the surgical camera.

16. The system of claim 15, wherein (i) and (ii) are repeated until the at least one of the surgical camera or the robotic arm is moved until the virtual mark is aligned with the physical mark,
wherein subsequent poses of the surgical camera and the robotic arm are recorded or determined as (i) and (ii) are repeated, and
wherein a final registration correction transformation is calculated as the pose delta between the first pose and a final pose of the subsequent poses.

17. The system of claim 14, wherein the patient volume space of the virtual positional data points and the recorded virtual mark are held fixed relative to the surgical camera when the at least one of the surgical camera or the robotic arm is moved to align the virtual mark with the physical mark.

18. The system of claim 13, wherein execution of the machine-readable instructions further causes the processor to:
enter a correction phase when a request is received from an operator or the distance between the location of the virtual mark and the location of the physical mark exceeds the threshold; and
cause the patient volume space of the virtual positional data points and the recorded virtual mark to move within the live image data recorded by the surgical camera such that the virtual mark becomes aligned with the physical mark,
wherein the surgical camera and a robotic arm supporting the surgical camera are held in a fixed pose during movement of the patient volume space of the virtual positional data points and the recorded virtual mark.

19. The system of claim 13, wherein the surgical camera is connected to a robotic arm, and wherein execution of the machine-readable instructions further causes the processor to:
at a time the virtual mark is created, associatively store with the virtual mark a waypoint including at least one of a robot pose of the robotic arm in the form of joint angles or camera optical properties including at least one of zoom, focus, orientation, or coupler settings; and
cause at least one of the robotic arm or the surgical camera to return to the waypoint to enable an operator to begin a process of correcting the misalignment between the location of the virtual mark and the location of the physical mark.

20. The system of claim 13, wherein the surgical camera is connected to a robotic arm, and wherein execution of the machine-readable instructions further causes the processor to iteratively move the robotic arm and use the live image data to determine a new distance between the location of the virtual mark and the location of the physical mark until the location of the virtual mark is aligned with the location of the physical mark.

21. A system comprising:
a surgical marking pen including a tip and a trackable target, the surgical marking pen configured to generate a physical mark on a patient;
a navigation camera, wherein the trackable target and the tip of the surgical marking pen are posed at least some of the time such that they are visible to the camera;
a memory storing machine-readable instructions; and
a processor in communication with the memory, wherein execution of the machine-readable instructions causes the processor to:
perform an initial patient registration that generates a patient volume space of virtual positional data points that corresponds to physical positional points of at least a portion of a patient,
receive or determine a pose transformation between the trackable target and the surgical pen tip,
record a virtual mark in the patient volume space in response to an activation action performed by the surgical marking pen using the pose transformation, the virtual mark being a virtual positional data point that corresponds to the physical positional point of a physical mark generated on the patient by the tip of the surgical marking pen, and
cause the patient volume space of virtual positional data points and the recorded virtual mark to be displayed in an overlaid manner over live image data recorded by a surgical camera on a single display.

22. A system comprising:
a navigation camera;
surgical visualization camera;
a memory storing machine-readable instructions; and
a processor in communication with the memory, wherein execution of the machine-readable instructions causes the processor to:

perform an initial patient registration using the navigation camera that generates a patient volume space of virtual positional data points that corresponds to physical positional points of at least a portion of a patient, perform calibration of the surgical visualization camera to determine a location of crosshairs or other indicator in a space of the navigation camera and within the patient volume space, use a display of the surgical visualization camera or a separate projection device to display the crosshairs or other indicator on a portion of the patient, adjust a location of the crosshairs or other indicator based on received input from an operator, record a virtual mark in the patient volume space in response to an activation action at the adjusted location of the crosshairs or other indicator, the virtual mark being a virtual positional data point that corresponds to the physical positional point of a physical mark generated on the patient a marking pen, and cause the patient volume space of virtual positional data points and the recorded virtual mark to be displayed in an overlaid manner over live image data recorded by a surgical camera on a single display.

* * * * *